(12) United States Patent
Mader et al.

(10) Patent No.: US 9,751,937 B2
(45) Date of Patent: *Sep. 5, 2017

(54) ANTAGONIST ANTIBODIES AGAINST GDF-8 AND USES THEREFOR

(71) Applicant: PFIZER INC., New York, NY (US)

(72) Inventors: Michelle M. Mader, Clayton, NC (US); James R. Apgar, Somerville, MA (US); Kevin D. Parris, Groton, CT (US)

(73) Assignee: PFIZER INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/626,321

(22) Filed: Feb. 19, 2015

(65) Prior Publication Data

US 2015/0337032 A1 Nov. 26, 2015

Related U.S. Application Data

(63) Continuation of application No. 13/916,379, filed on Jun. 12, 2013, now Pat. No. 8,992,913.

(60) Provisional application No. 61/660,232, filed on Jun. 15, 2012.

(51) Int. Cl.
| | |
|---|---|
| A61K 39/00 | (2006.01) |
| A61K 39/395 | (2006.01) |
| C07K 16/22 | (2006.01) |
| A61K 45/06 | (2006.01) |
| C07K 16/00 | (2006.01) |

(52) U.S. Cl.
CPC ............ *C07K 16/22* (2013.01); *A61K 39/395* (2013.01); *A61K 39/3955* (2013.01); *A61K 45/06* (2013.01); *C07K 16/00* (2013.01); *A61K 2039/505* (2013.01); *A61K 2039/622* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,740,461 A | 4/1988 | Kaufman | |
| 4,912,040 A | 3/1990 | Kaufman et al. | |
| 4,959,455 A | 9/1990 | Clark et al. | |
| 5,624,821 A | 4/1997 | Winter et al. | |
| 5,648,260 A | 7/1997 | Winter et al. | |
| 5,741,957 A | 4/1998 | Deboer et al. | |
| 5,750,172 A | 5/1998 | Meade et al. | |
| 5,756,687 A | 5/1998 | Denman | |
| 5,827,690 A | 10/1998 | Meade et al. | |
| 5,951,974 A | 9/1999 | Gilbert et al. | |
| 5,959,177 A | 9/1999 | Hein et al. | |
| 6,012,454 A | 1/2000 | Hodson et al. | |
| 6,030,613 A | 2/2000 | Blumberg et al. | |
| 6,046,037 A | 4/2000 | Hiatt et al. | |
| 6,096,506 A | 8/2000 | Lee et al. | |
| 6,102,035 A | 8/2000 | Asking et al. | |
| 6,372,454 B2 | 4/2002 | Duan et al. | |
| 6,407,213 B1 | 6/2002 | Carter et al. | |
| 6,417,429 B1 | 7/2002 | Hein et al. | |
| 6,465,239 B1 | 10/2002 | Lee et al. | |
| 6,607,884 B1 | 8/2003 | Lee et al. | |
| 6,673,534 B1 | 1/2004 | Lee et al. | |
| 6,891,082 B2 | 5/2005 | Lee et al. | |
| 7,192,717 B2 | 3/2007 | Hill et al. | |
| 7,261,893 B2 | 8/2007 | Veldman et al. | |
| 7,320,789 B2 | 1/2008 | Aghajanian et al. | |
| 7,381,528 B2 | 6/2008 | Lee et al. | |
| 7,393,682 B1 | 7/2008 | Lee et al. | |
| 7,888,486 B2 | 2/2011 | Walsh et al. | |
| 7,910,107 B2 | 3/2011 | Walsh et al. | |
| 8,349,327 B2 | 1/2013 | Walsh et al. | |
| 8,372,625 B2 | 2/2013 | Walsh et al. | |
| 8,496,934 B2 | 7/2013 | Walsh et al. | |
| 8,956,608 B2 | 2/2015 | Walsh et al. | |
| 8,992,913 B2 * | 3/2015 | Mader .................. | C07K 16/22 424/130.1 |
| 2002/0127234 A1 | 9/2002 | El Halawani et al. | |
| 2002/0157125 A1 | 10/2002 | Lee et al. | |
| 2003/0074680 A1 | 4/2003 | Lee et al. | |
| 2003/0118592 A1 | 6/2003 | Ledbetter et al. | |
| 2003/0133939 A1 | 7/2003 | Ledbetter et al. | |
| 2003/0138422 A1 | 7/2003 | Aghajanian et al. | |

(Continued)

FOREIGN PATENT DOCUMENTS

| | | |
|---|---|---|
| EP | 1 411 064 | 4/2004 |
| EP | 1 915 397 | 4/2008 |

(Continued)

OTHER PUBLICATIONS

Murphy et al., 2010, Am. J. Pathol. 176:2425-2434.*
Dschietzig, 2014, Clinica Chimica Acta 433:216-224.*
Kim et al., 2007, Poultry Science 86:1196-1205.*
Vajdos et al., "Comprehensive functional maps of the antigen-binding site of an anti-ErbB2 antibody obtained with shotgun scanning mutagenesis", J. Mol. Biol., 320(2):415-28 (2002).
Van den Beucken et al., "Building Novel Binding Ligands to B7.1 and B7.2 Based on Human Antibody Single Variable Light Chain Domains", J. Mol. Biol., 310:591-601 (2001).
Verkman, "Drug discovery in academia", Am. J. Physiol. Cell Physiol., 286:465-74 (2004).

(Continued)

*Primary Examiner* — Elizabeth C Kemmerer

(57) ABSTRACT

The disclosure provides improved neutralizing anti-GDF-8 antibodies capable of substantially higher levels of expression in host cells compared to previous anti-GDF-8 antibodies. Also provided are methods of using compositions comprising such antibodies to increase muscle mass or strength, and to treat or prevent muscular disorders, neuromuscular disorders, metabolic disorders, adipose tissue disorders or bone disorders.

20 Claims, 19 Drawing Sheets

(56) References Cited

U.S. PATENT DOCUMENTS

| | | |
|---|---|---|
| 2004/0055027 A1 | 3/2004 | Lee et al. |
| 2004/0058445 A1 | 3/2004 | Ledbetter et al. |
| 2004/0142382 A1 | 7/2004 | Veldman et al. |
| 2005/0014733 A1 | 1/2005 | Whittemore et al. |
| 2005/0136049 A1 | 6/2005 | Ledbetter et al. |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2005/0257278 A1 | 11/2005 | Lee et al. |
| 2006/0240487 A1 | 10/2006 | Nowak et al. |
| 2006/0240488 A1 | 10/2006 | Nowak et al. |
| 2008/0178310 A1 | 7/2008 | Lee et al. |
| 2008/0213426 A1 | 9/2008 | Lee et al. |
| 2012/0003212 A1 | 1/2012 | Walsh et al. |
| 2012/0016106 A1 | 1/2012 | Walsh et al. |
| 2014/0086920 A1 | 3/2014 | Walsh et al. |
| 2015/0152176 A1 | 6/2015 | Walsh et al. |

FOREIGN PATENT DOCUMENTS

| | | |
|---|---|---|
| WO | 94/21681 | 9/1994 |
| WO | 96/33735 | 10/1996 |
| WO | 96/34015 | 10/1996 |
| WO | 96/34096 | 10/1996 |
| WO | 97/10847 | 3/1997 |
| WO | 98/33887 | 8/1998 |
| WO | 99/02667 | 2/1999 |
| WO | 99/06559 | 2/1999 |
| WO | 99/24618 | 5/1999 |
| WO | 99/40181 | 8/1999 |
| WO | 9956768 | 11/1999 |
| WO | 00/09560 | 2/2000 |
| WO | 00/43781 | 7/2000 |
| WO | 01/05820 | 1/2001 |
| WO | 03/072714 | 9/2003 |
| WO | 03/072715 | 9/2003 |
| WO | 2004/037861 | 5/2004 |
| WO | 2004/039948 | 5/2004 |
| WO | 2004/108157 | 12/2004 |
| WO | 2006/102574 | 9/2006 |
| WO | 2006/107611 | 10/2006 |
| WO | 2007/024535 | 1/2007 |
| WO | 2009/058346 | 5/2009 |

OTHER PUBLICATIONS

Vukicevic et al., "Induction of nephrogenic mesenchyme by osteogenic protein 1 (bone morphogenetic protein 7)", Proc. Natl. Acad. Sci. U.S.A., 93:9021-9026 (1996).
Wagner et al., "Loss of Myostatin Attenuates Severity of Muscular Dystrophy in mdx Mice", Ann. Neurol., 52:832-36 (2002).
Wakefield, et al., (1988) J. Biol. Chem. 263:7646-54.
Wang et al., "Neuroprotective Effects of Glial Cell Line-Derived Neurotrophic Factor Mediated by an Adeno-Associated Virus Vector in a Transgenic Animal Model of Amyotrophic Lateral Sclerosis", J. Neurosci., 22:6920-28 (2002).
Ward et al., "Binding activities of a repertoire of single immunoglobulin variable domains secreted from *Escherichia coli*", Nature, 341:544-46 (1989).
Whittemore et al., "Inhibition of myostatin in adult mice increases skeletal muscle mass and strength", Biochem. Biophys. Res. Commun., 300:965-71 (2003).
Wilkes et al., "Loss-of-function mutation in myostatin reduces tumor necrosis factor alpha production and protects liver against obesity-induced insulin resistance", Diabetes, 58(5):1133-43 (2009).
Wooley et al., "Gait analysis detects early changes in transgenic SOD1 (G93A) mice", Muscle Nerve, 32:43-50 (2005).
Wu et al., "Humanization of a murine monoclonal antibody by simultaneous optimization of framework and CDR residues", J. Mol. Biol., 294(1):151-62 (1999).
Zimmers et al., "Induction of Cachexia in Mice by Systemically Administered Myostatin", Science, 296:1486-88 (2002).
U.S. Appl. No. 11/503,062 (U.S. Pat. No. 7,888,486)—Preliminary Amendment (Nov. 11, 2007.
U.S. Appl. No. 11/503,062 (U.S. Pat. No. 7,888,486)—Office Action—Non-Final Rejection (Dec. 12, 2007).
U.S. Appl. No. 11/503,062 (U.S. Pat. No. 7,888,486)—Office Action—Final Rejection (Sep. 3, 2008).
U.S. Appl. No. 11/503,062 (U.S. Pat. No. 7,888,486)—Office Action—Adivsory Action (Jan. 26, 2009).
U.S. Appl. No. 11/503,062 (U.S. Pat. No. 7,888,486)—Office Action—Non-Final Rejection—Notice to Comply (Jul. 10, 2009).
U.S. Appl. No. 11/503,062 (U.S. Pat. No. 7,888,486)—Office Action—Non-Final Rejection (Apr. 14, 2010).
U.S. Appl. No. 11/503,062 (U.S. Pat. No. 7,888,486)—Notice of Allowability and examiner's amendment (Sep. 30, 2010).
U.S. Appl. No. 11/503,062 (U.S. Pat. No. 7,888,486)—Amendment—(Apr. 10, 2008).
U.S. Appl. No. 11/503,062 (U.S. Pat. No. 7,888,486)—Amendment—(Jan. 6, 2009).
U.S. Appl. No. 11/503,062 (U.S. Pat. No. 7,888,486)—Amendment (Mar. 3, 2009).
U.S. Appl. No. 11/503,062 (U.S. Pat. No. 7,888,486)—Amendment (Jan. 8, 2010).
U.S. Appl. No. 11/503,062 (U.S. Pat. No. 7,888,486)—Amendment (Jul. 14, 2010).
U.S. Appl. No. 12/508,618 (U.S. Pat. No. 7,910,107)—Preliminary Amendment (Jul. 24, 2009).
U.S. Appl. No. 12/508,618 (U.S. Pat. No. 7,910,107)—Amendment (Sep. 3, 2010).
U.S. Appl. No. 12/508,618 (U.S. Pat. No. 7,910,107)—Office Action—Non-Final Rejection (Apr. 6, 2010).
U.S. Appl. No. 12/508,618 (U.S. Pat. No. 7,910,107)—Notice of Allowability and Examiner's Amendment (Dec. 1, 2010).
U.S. Appl. No. 13/030,978 (U.S. Pat. No. 8,349,327)—Preliminary Amendment (Sep. 14, 2011).
U.S. Appl. No. 13/030,978 (U.S. Pat. No. 8,349,327)—Office Action—Non-Final Rejection (Dec. 16, 2011).
U.S. Appl. No. 13/030,978 (U.S. Pat. No. 8,349,327)—Amendment (May 16, 2012).
U.S. Appl. No. 13/030,978 (U.S. Pat. No. 8,349,327)—Notice of Allowability (Jun. 15, 2012).
U.S. Appl. No. 13/030,978 (U.S. Pat. No. 8,349,327)—Notice of Allowability (Sep. 7, 2012).
U.S. Appl. No. 13/038,954 (U.S. Pat. No. 8,372,625)—Notice of Allowability (Oct. 15, 2012).
U.S. Appl. No. 13/038,954 (U.S. Pat. No. 8,372,625)—Notice of Allowability (Jun. 14, 2012).
U.S. Appl. No. 13/693,995 (U.S. Pat. No. 8,496,934)—Notice of Allowability (Mar. 26, 2013).
U.S. Appl. No. 13/693,995 (U.S. Pat. No. 8,496,934)—Preliminary Amendment (Dec. 4, 2012).
Abbas, A.K., Lichtman, A.H. and Pillai, S., 2010, Cellular and Molecular Immunology, 6th Ed., Chapter 8, Saunders, Philadelphia, PA.
Al-Lazikani et al., "Standard Conformations for the Canonical Structures of Immunoglobulins", J. Mol. Bioi., 273:927-48 (1997).
Akpan et al., "The effects of a soluble activin type IIB receptor on obesity and insulin sensitivity", Int. J. Obes. (Lond)., 33(11):1265-73 (2009).
Alfarano et al., "The Biomolecular Interaction Network Database and related tools 2005 update", Nuc. Acids Res. Database, Issue 33:D418-24 (2005).
Ashmore et al. (1974) Growth 38:501-06.
Attwood, "Genomics: The Babel of Bioinformatics", Science, 290:471-473 (2000).
Azzouz et al., "VEGF delivery with retrogradely transported lentivector prolongs survival in a mouse ALS model", Nature, 429:413-17 (2004).

(56) References Cited

OTHER PUBLICATIONS

Bellinge et al., "Myostatin and Its Implications on animal breeding: a review", Animal Genetics, 36:1-6 (2005).
Bending, "Humanization of Rodent Monoclonal Antibodies by CDR Grafting", Methods: A Companion to Methods in Enzymology, 8:83-93 (1995).
Bogdanovich et al., "Functional improvement of dystrophic muscle by myostatin blockade", Nature, 420:418-21 (2002).
Brown et al., "Physicochemical Activation of Recombinant Latent Transforming Growth Factor-beta's 1, 2, and 3", Growth Factors, 3:35-43 (1999).
Bruijn et al., "Unraveling the Mechanisms Involved in Motor Neuron Degeneration in ALS", Annu. Rev. Neurosci., 27:723-49 (2004).
Casas et al., "Association of the Muscle Hypertrophy Locus with Carcass Traits in Beef Cattle", J. Anim. Sci., 76:468-473 (1998).
Casset et al., "A peptide mimetic of an anti-CD4 monoclonal antibody by rational design", Biochem. Biophys. Res. Commun., 307(1):198-205 (2003).
Chao, "Retrograde Transport Redux", Neuron, 39:1-2 (2003).
Chen et al., "Selection and analysis of an optimized anti-VEGF antibody: crystal structure of an affinity-matured Fab in complex with antigen", J. Mol. Biol., 293(4):865-81 (1999).
Clement et al., "Wild-Type Nonneuronal Cells Extend Survival of SOD1 Mutant Motor Neurons in ALS Mice", Science, 302:113-17 (2003).
Davis et al., "Crystal structure of prostate-specific membrane antigen, a tumor marker and peptidase", Proc. Natl. Acad. Sci. U.S.A., 102:5981-86 (2005).
Dennler et al., "Direct binding of Smad3 and Smad4 to critical TGFβ-inducible elements in the promoter of human plasminogen activator inhibitor-type 1 gene", EMBO J., 17:3091-3100 (1998).
Derynck, et al. "Human transforming growth factor-complementary DNA sequence and expression in normal and transformed cells", Nature (1985) Nature 316:701-05.
Dickman, S., "Gene Mutation Provides More Meat on the Hoof", Science, 277:1922-1923 (1997).
Dobrowolny et al., "Muscle expression of a localIgf-1 isoform protects motor neurons in an ALS mouse model", J. Cell Biol., 168(2):193-99 (2005).
Downer, J., (2002) "New, Better Rat Model Reveals Astrocyte Role in ALS", UniSci (3 pgs.) Jan. 30, 2002 httQ://www.unisci.com/stories/20021/0130021.htm printed Nov. 19, 2007.
Dunlop et al., "Impaired Spinal Cord Glutamate Transport Capacity and Reduced Sensitivity to Riluzole in a Transgenic Superoxide Dismutase Mutant Rat Model of Amyotrophic Lateral Sclerosis", J. Neurosci., 23:1688-96 (2003).
Dupuis et al., "Evidence for defective energy homeostasis in amyotrophic lateral sclerosis: Benefit of a high-energy diet in a transgenic mouse model", Proc. Natl. Acad. Sci. U.S.A., 101:11159-64 (2004).
Emsley, P. & Cowtan, K. (2004) Coot: model-building tools for molecular graphics. Acta Crystallogr., Sect. D: Biol. Crystallogr. 60, 2126-2132.
Fischer et al., "Amyotrophic lateral sclerosis is a distal axonopathy: evidence in mice and man", Exp. Neurol., 185:232-40 (2004).
Frey et al., "Early and Selective Loss of Neuromuscular Synapse Subtypes with Low Sprouting Competence in Motoneuron Diseases", J. Neurosci., 20:2534-42 (2000).
Garner et al., "A Novel BMP Expressed in Developing Mouse Limb, Spinal Cord, and Tail Bud is a Potent Mesoderm Inducer in Xenopus Embryos", Dev. Bioi., 208:222-32 (1999).
Gardlik et al., "Vectors and delivery systems in gene therapy", Med. Sci. Monit., 11:RA110-21 (2005).
Gentry et al. (1990) Biochemistry 29:6851-57.
Gonzalez-Cadavid et al., "Organization of the human myostatin gene and expression in healthy men and HIV-infected men with muscle wasting", Proc. Natl. Acad. Sci. U.S.A., 95:14938-43 (1998).

Grobet et al., "A Deletion in the Bovine Myostatin Gene Causes the Double-Muscled Phenotype in Cattle", Nature Genetics, 17:71-74 (1997).
Guo et al., "Increased expression of the glial glutamate transporter EAA T2 modulates excitotoxicity and delays the onset but not the outcome of ALS in mice", Hum. Mol. Genet., 12:2519-32 (2003).
Guo et al., "Myostatin inhibition in muscle, but not adipose tissue, decreases fat mass and improves insulin sensitivity", PLoS One, 4(3):e4937 (2009).
Gumey et al. (1994) Science 264:1772-75.
Halpin and Harbury, "DNA Display II Genetic Manipulation of Combinatorial Chemistry Libraries for Small-Molecule Evolution", PLoS Biology, 2:1 022-30 (2004).
Hamrick et al., "Femoral Morphology and Cross-sectional Geometry of Adult Myostatin-Deficient Mice", Bone, 27:343-49 (2000).
Hamrick et al., "Bone architecture and disc degeneration in the lumbar spine of mice lacking GDF-8 (myostatin)", J. Orthop. Res., 21(6):1025-32 (2003).
Hamrick et al., "Bone mineral content and density in the humerus of adult myostatin-deficient mice", Calcif. Tissue Int., 71(1):63-8 (2002).
Hamrick et al., "Recombinant myostatin (GDF-8) propeptide enhances the repair and regeneration of both muscle and bone in a model of deep penetrant musculoskeletal injury", J. Trauma, 69(3):579-83 (2010).
Hamrick M.W. "Increased bone mineral density in the femora of GDF8 knockout mice", Anat. Rec. A Discov. Mol. Cell. Evol. Biol., 272(1):388-91 (2003).
Holzbaur et al., "Myostatin inhibition slows muscle atrophy in rodent models of amyotrophic lateral sclerosis", Neurobiol. Dis., 23:697-707 (2006).
Holzbaur, "Motor neurons rely on motor proteins", Trends Cell Biol., 14:233-40 (2004).
Hoodless and Wrana, "Mechanism and Function of Signaling by the TGFβ Superfamily", Curr. Top. Microbial. Immunol., 228:235-72 (1998).
Howland et al., "Focal loss of the glutamate transporter EAA T2 in a transgenic rat model of SOD1 mutant-mediated amyotrophic lateral sclerosis (ALS)", Proc. Natl. Acad. Sci. U.S.A., 99:1604-09 (2002).
Kambadur et al., "Mutations in myostatin (GDF8) in Double-Muscled Belgian Blue and Piedmontese Cattle", Genome Res., 7:910-15 (1997).
Karp, "An ontology for biological function based on molecular interactions", Bioinformatics, 16:269-85 (2000).
Kaspar et al., "Retrograde Viral Delivery of IGF-1 Prolongs Survival in a Mouse ALS Model", Science, 301:839-42 (2003).
Kellum et al., "Myostatin (GDF-8) deficiency increases fracture callus size, Sox-5 expression, and callus bone volume", Bone, 44(1):17-23 (2009).
Kieran et al., "Treatment with arimoclomol, a coinducer of heat shock proteins, delays disease progression in ALS mice", Nat. Med., 10:402-05 (2004).
Kim et al., "Inhibition of Preadipocyte Differentiation by Myostatin Treatment in 3T3-L 1 Cultures", Biochem. Biophys. Res. Commun., 281:902-06 (2001).
Kingsley, et al., (1994) Genes Dev., 8:133-46.
Lee and McPherron, "Myostatin and the control of skeletal muscle mass", Curr. Opin. Genet. Dev., 9:604-07 (1999).
Ligon et al., "Mutant superoxide dismutase disrupts cytoplasmic dynein in motor neurons," Neuro Report, 16:533-36 (2005).
Lamminmaki et al., "Crystal structure of a recombinant anti-estradiol Fab fragment in complex with 17beta-estradiol", J. Biol. Chem., 276(39):36687-94 (2001).
LaMonte et al., "Disruption of Dyneini/Dynactin Inhibits Axonal Transport in Motor Neurons Causing Late-Onset Progressive Degeneration", Neuron, 34:715-27 (2002).
Langley et al., "Myostatin Inhibits Myoblast Differentiation by Down-Regulating MyoD Expression", J. Biol. Chem., 277:49831-40 (2002).
Lechtzin et al., "Amyotrophic lateral sclerosis: evaluation and treatment of respiratory impairment", Amyotroph. Lateral Seler Other Motor Neuron Disord., 3:5-13 (2002).

(56) References Cited

OTHER PUBLICATIONS

PCT/IB2013/054810, International Search Report and Written Opinion of the Int'l Search Authority, Mailed: Sep. 19, 2013, 11 pages.
PCT/US2006/031651 (WO 07/024535), International Search Report; Mailed Feb. 15, 2007, 8 pages.
MacCallum et al., "Antibody-antigen interactions: contact analysis and binding site topography", J. Mol. Biol., 262 (5):732-45 (1996).
J. Massague, "The Transforming Growth Factor-beta Family." Ann. Rev. Cell. and Dev. Biol. 6:597-641. (1990).
McCroskery et al., "Improved muscle healing through enhanced regeneration and reduced fibrosis in myostatin-null mice", J. Cell. Sci., 118:3531-41 (2005).
McCroskery et al., "Myostatin negatively regulates satellite cell activation and self-renewal", J. Cell Biol., 162 (6):1135-47 (2003).
McKnight, Steven L, "Gatekeepers of Organ Growth", Proc. Natl. Acad. Sci. U.S.A., 94:12249-12250 (1997).
McPherron and Lee, "Double muscling in cattle due to mutations in the myostatin gene", Proc. Natl. Acad. Sci. U.S.A., 94:12457-61 (1997).
McPherron and Lee, "Suppression of body fat accumulation in myostatin-deficient mice", J. Clin. Invest., 109 (5):595-601 (2002).
McPherron et al., "Regulation of skeletal muscle mass in mice by a new TGF-13 superfamily member", Nature, 387:83-90 (1997).
McPherron et al., "Soluble activin receptor type IIB treatment does not cause fat loss in mice with diet-induced obesity", Diabetes Obes. Metab., Mar. 2012;14(3):279-82. Epub Nov. 21, 2011.
Mennissier, F., "Present State of Knowledge About the Genetic Determination of Muscular Hypertrophy or the Double Muscled Trait in Cattle", Muscle Hypertrophy of Genetic Origin and Its Uses to Improve Beef Production: A Seminar in CEC Programme of Coordinated Research on Beef Production, pp. 387-428 (1982).
Mitchell and Wall, "In vivo evaluation of changes in body composition of transgenic mice expressing the myostatin pro domain using dual energy X-ray absorptiometry", Growth Dev. Aging., 70(1):25-37 (2007).
Miyazono, et al., "Latent high molecular weight complex of transforming growth factor beta 1. Purification from human platelets and structural characterization." J. Biol. Chem. 263(13):6407-15. (1988).
Molina et al., "Improved Performances of Spot Multiple Peptide Synthesis", Peptide Res., 9:151-55 (1996).
Morgan et al., "The N-terminal end of the CH2 domain of chimeric human IgG1 and anti-HLA-DR is necessary for C1q, FcγR1 and FcγRIII binding", Immunology, 86:319-24 (1995).
Muyldermans et al., "Recognition of antigens by single-domain antibody fragments: the superfluous luxury of paired domains", Trends Biochem. Sci., 26:230-35 (2001).
Muyldermans, "Single domain camel antibodies: current status", Rev. Mol. Biotechnol., 74:277-302 (2001).
Nakatani et al., "Follistatin-derived peptide expression in muscle decreases adipose tissue mass and prevents hepatic steatosis", Am. J. Physiol. Endocrinol. Metab., 300(3):E543-53 (2011). Epub Jan. 4, 2011.
Navaz, J. (2001). Implementation of molecular replacement in AMoRe. Acta Crystallogr., Sect. D: Biol. Crystallogr. 57, 1367-1372.
Y. Ofran, et al., Automated identification of complementarity determining regions (CDRs) reveals peculiar characteristics of CDRs and B cell epitopes, J Immunol. Nov. 1, 2008:181(9):6230-5.
Z. Otwinowski and W. Minor, "Processing of X-ray Diffraction Data Collected in Oscillation Mode", Methods in Enzymology, vol. 276: Macromolecular Crystallography, Part A, p. 307-326, 1997, C.W. Carter, Jr. & R.M. Sweet, Eds., Academic Press (New York)).
Padlan et al., "Structure of an antibody-antigen complex: crystal structure of the HyHEL-10 Fab-lysozyme complex", Proc. Natl. Acad. Sci. U.S.A., 86:5938-5942 (1989).

Parkington, Bialek, Watner et al., "Mice treated with a myostatin/GDF-8 decoy receptor, ActRIIB-Fc, exhibit a tremendous increase in bone mass", Abstracts / Bone, 42:S17-S110, abstract No. 66 (2008).
Pascalis et al., "Grafting of "abbreviated" complementarity-determining regions containing specificity-determining residues essential for ligand contact to engineer a less immunogenic humanized monoclonal antibody", J. Immunol., 169(6)3076-84 (2002).
Philip, et al., Regulation of GDF-8 signaling by the p38 MAPK, Cellular Signalling (2005) 17:365-375.
Reaume et al., "Motor neurons in Cu/Zn superoxide dismutase-deficient mice develop normally but exhibit enhanced cell death after axonal injury", Nat. Genet, 13:43-47 (1996).
Rudikoff et al. "Single amino acid substitution altering antigen-binding specificity", Proc. Natl. Acad. Sci. U.S.A., 79 (6):1979-83 (1982).
Schier et al., "Isolation of Picomolar Affinity Anti-c-erbB-2 Single-chain Fv by Molecular Evolution of the Complementarity Determining Regions in the Center of the Antibody Binding Site", J. Mol. Biol., 263:551-67 (1996).
Schmitz and Hof, "Design-based stereology in neuroscience", Neuroscience, 130:813-31 (2005).
Schmitz and Hof, "Recommendations for straightforward and rigorous methods of counting neurons based on a computer simulation approach", J. Chem. Neuroanat., 20:93-114 (2000).
Schutz et al., "The Oral Antidiabetic Pioglitazone Protects from Neurodegeneration and Amyotrophic Lateral Sclerosis-Like Symptoms in Superoxide Dismutase-G93A Transgenic Mice", J. Neurosci., 25:7805-12 (2005).
Sharp, "The effect of peripheral nerve injury on disease progression in the SOD1(G93A) mouse model of amyotrophic lateral sclerosis", Neuroscience, 130:897-910 (2005).
Shields et al., "High Resolution Mapping of the Binding Site on Human IgG1 for FcγRl, FcγRll, FcγRIII, and FcRn and Design of IgG1 Variants with Improved Binding to the FcγR", J. Biol. Chem. 276:6591-604 (2001).
Skolnick et al., "From genes to protein structure and function: novel applications of computational approaches in the genomic era", Trends in Biotechnol., 18:34-39 (2000).
Swatland, et al, (1974) J. Anim. Sci., 38:752-57.
PCT/US2006/031651 (WO 07/024535), Int'l Preliminary Report on Patentability, Feb. 20, 2008.
PCT/US2006/031651 (WO 07/024535), Written Opinion of the Int'l Search Authority, Feb. 19, 2008.
Thies et al., "GDF-8 Propeptide Binds to GDF-8 and Antagonizes Biological Activity by Inhibiting GDF-8 Receptor Binding", Growth Factors, 18:251-59 (2001).
Thomas et al., "Myostatin, a Negative Regulator of Muscle Growth, Functions by Inhibiting Myoblast Proliferation", J. Biol. Chem., 275:40235-43 (2000).
Tobin and Celeste, "Myostatin, a negative regulator of muscle mass: implications for muscle degenerative diseases", Curr. Opin. Pharmacol., 5:328-32 (2005).
Murphy, KT, et al. Antibody-directed myostatin inhibition improves diaphragm pathology in young but not adult dystrophic mdx mice. Am. J. Pathol. 176(5):2425-34 (2010).
Murphy, KT, et al. Antibody-directed myostatin inhibition in 21-mo-old mice reveals novel roles for myostatin signaling in skeletal muscle structure and function. FASEB J. 24(11):4433-42 (2010).
Murphy, KT, et al. Acute antibody-directed myostatin inhibition attenuates disuse muscle atrophy and weakness in mice. J. Appl. Physiol. 110:1065-72 (2011).
Murphy, KT, et al. Antibody-directed myostatin inhibition enhances muscle mass and function in tumor-bearing mice. Am. J. Physiol. 301:R716-R726 (2011).

* cited by examiner

FIG. 1A

Anti-GDF-8 antibody variable heavy (VH) region amino acid alignments

```
Murine VH      1  EVQLVESGGGLVKPGGSLKLSCAASGFTFSSYAMSWVRQT     40  (SEQ ID NO:3)
DP-47          1  EVQLLESGGGLVQPGGSLRLSCAASGFTFSSYAMSWVRQA     40  (SEQ ID NO:33)
Humanized VH0  1  EVQLLESGGGLVQPGGSLRLSCAASGFTFSSYAMSWVRQA     40  (SEQ ID NO:44)
Humanized VH1  1  EVQLLESGGGLVQPGGSLRLSCAASGFTFSSYAMSWVRQA     40  (SEQ ID NO:7)
Humanized VH2  1  EVQLLESGGGLVQPGGSLRLSCAASGFTFSSYAMSWVRQA     40  (SEQ ID NO:66)
Humanized VH3  1  EVQLLESGGGLVQPGGSLRLSCAASGFTFSSYAMSWVRQA     40  (SEQ ID NO:68)
Humanized VH4  1  EVQLLESGGGLVQPGGSLRLSCAASGFTFSSYAMSWVRQA     40  (SEQ ID NO:70)
Humanized VH5  1  EVQLLESGGGLVQPGGSLRLSCAASGFTFSSYAMSWVRQA     40  (SEQ ID NO:72)

Murine VH     41  PEKRLEWVATISSGGSYTSYPDSVKGRFTISRDNAKNTLY     80  (SEQ ID NO:3)
DP-47         41  PGKGLEWVSAISGSGGSTYYADSVKGRFTISRDNSKNTLY     80  (SEQ ID NO:33)
Humanized VH0 41  PGKGLEWVSTISSGGSYTSYPDSVKGRFTISRDNSKNTLY     80  (SEQ ID NO:44)
Humanized VH1 41  PGKGLEWVSAISGSGGSTYYADSVKGRFTISRDNSKNTLY     80  (SEQ ID NO:7)
Humanized VH2 41  PGKGLEWVSAISSSGGYTYYADSVKGRFTISRDNSKNTLY     80  (SEQ ID NO:66)
Humanized VH3 41  PGKGLEWVSTISSGGSYTSYPDSVKGRFTISRDNSKNTLY     80  (SEQ ID NO:68)
Humanized VH4 41  PGKGLEWVSTISSGGSYTSYPDSVKGRFTISRDNSKNTLY     80  (SEQ ID NO:70)
Humanized VH5 41  PGKGLEWVSTISSGGSYTSYPDSVKGRFTISRDNSKNTLY     80  (SEQ ID NO:72)
                                         *
Murine VH     81  LQMSSLRSEDTAMYYCARQDYAMNYWGQGTSVTVSS       116 (SEQ ID NO:3)
DP-47         81  LQMNSLRAEDTAVYYCAK                          98  (SEQ ID NO:33)
Humanized VH0 81  LQMNSLRAEDTAVYYCAKQDYAMNYWGQGTLVTVSS       116 (SEQ ID NO:44)
Humanized VH1 81  LQMNSLRAEDTAVYYCAKQDYAMNYWGQGTLVTVSS       116 (SEQ ID NO:7)
Humanized VH2 81  LQMNSLRAEDTAVYYCAKQDYAMNYWGQGTMVTVSS       116 (SEQ ID NO:66)
Humanized VH3 81  LQMNSLRAEDTAVYYCAKQDYAMNYWGQGTLVTVSS       116 (SEQ ID NO:68)
Humanized VH4 81  LQMNSLRAEDTAVYYCAKQDYAFDYWGQGTLVTVSS       116 (SEQ ID NO:70)
Humanized VH5 81  LQMNSLRAEDTAVYYCAKQDYAMNYWGQGTLVTVSS       116 (SEQ ID NO:72)
```

FIG. 1B

Antibody variable light (VL) region amino acid alignments

```
Murine VL       1  DIEMTQSHKFMSTSVGDRVSITCKASQDVSTAVAWYQQKP  40  (SEQ ID NO:5)
DPK-9           1  DIQMTQSPSSLSASVGDRVTITCRASQSISSYLNWYQQKP  40  (SEQ ID NO:32)
Humanized VL0   1  DIQMTQSPSSLSASVGDRVTITCKASQDVSTAVAWYQQKP  40  (SEQ ID NO:46)
Humanized VL1   1  DIQMTQSPSSLSASVGDRVTITCKASQDVSTAVAWYQQKP  40  (SEQ ID NO:9)
Humanized VL2   1  DIQMTQSPSSLSASVGDRVTITCKASQDVSTAVAWYQQKP  40  (SEQ ID NO:67)
Humanized VL3   1  DIQMTQSPSSLSASVGDRVTITCRASQSISTALNWYQQKP  40  (SEQ ID NO:69)
Humanized VL4   1  DIQMTQSPSSLSASVGDRVTITCRASQSISTALNWYQQKP  40  (SEQ ID NO:71)
Humanized VL5   1  DIQMTQSPSSLSASVGDRVTITCRASQSISTALNWYQQKP  40  (SEQ ID NO:73)

Murine VL      41  GQSPKLLIYSASYRYTGVPDRFTGSGSGTDFTFTISSVQA  80  (SEQ ID NO:5)
DPK-9          41  GKAPKLLIYAASSLQSGVPSRFSGSGSGTDFTLTISSLQP  80  (SEQ ID NO:32)
Humanized VL0  41  GKAPKLLIYSASYRYTGVPSRFSGSGSGTDFTLTISSLQP  80  (SEQ ID NO:46)
Humanized VL1  41  GKAPKLLIYSASYRYTGVPSRFSGSGSGTDFTLTISSLQP  80  (SEQ ID NO:9)
Humanized VL2  41  GKAPKLLIYAASSLQSGVPSRFSGSGSGTDFTLTISSLQP  80  (SEQ ID NO:67)
Humanized VL3  41  GKAPKLLIYSASSLQSGVPSRFSGSGSGTDFTLTISSLQP  80  (SEQ ID NO:69)
Humanized VL4  41  GKAPKLLIYAASSLQSGVPSRFSGSGSGTDFTLTISSLQP  80  (SEQ ID NO:71)
Humanized VL5  41  GKAPKLLIYSASSLQSGVPSRFSGSGSGTDFTLTISSLQP  80  (SEQ ID NO:73)
                                *

Murine VL      81  EDLAVYYCQQHYSTPWTFGGGTKLEIK            107  (SEQ ID NO:5)
DPK-9          81  EDFATYYCQQSYSTP                         95  (SEQ ID NO:32)
Humanized VL0  81  EDFATYYCQQHYSTPWTFGGGTKVEIK            107  (SEQ ID NO:46)
Humanized VL1  81  EDFATYYCQQHYSTPWTFGQGTKVEIK            107  (SEQ ID NO:9)
Humanized VL2  81  EDFATYYCQQHYSTPWTFGGGTKVEIK            107  (SEQ ID NO:67)
Humanized VL3  81  EDFATYYCQQSYSTPWTFGGGTKVEIK            107  (SEQ ID NO:69)
Humanized VL4  81  EDFATYYCQQSYSTPWTFGGGTKVEIK            107  (SEQ ID NO:71)
Humanized VL5  81  EDFATYYCQQSYSTPLTFGGGTKVEIK            107  (SEQ ID NO:73)
```

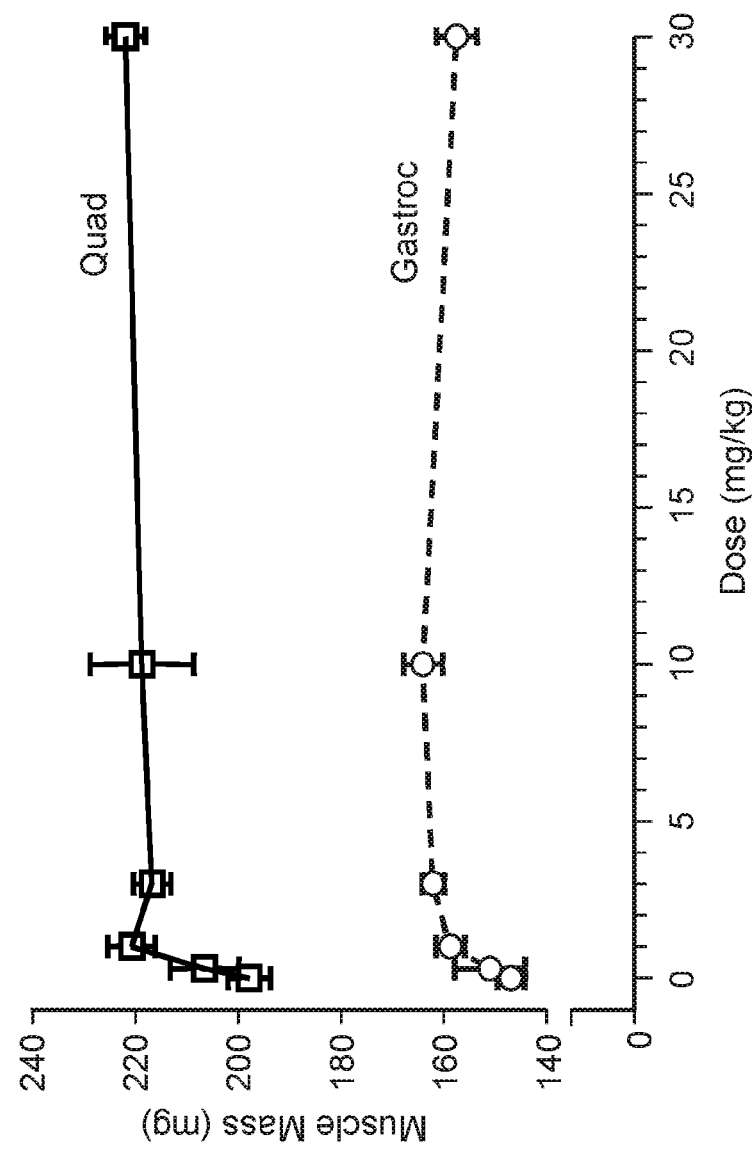

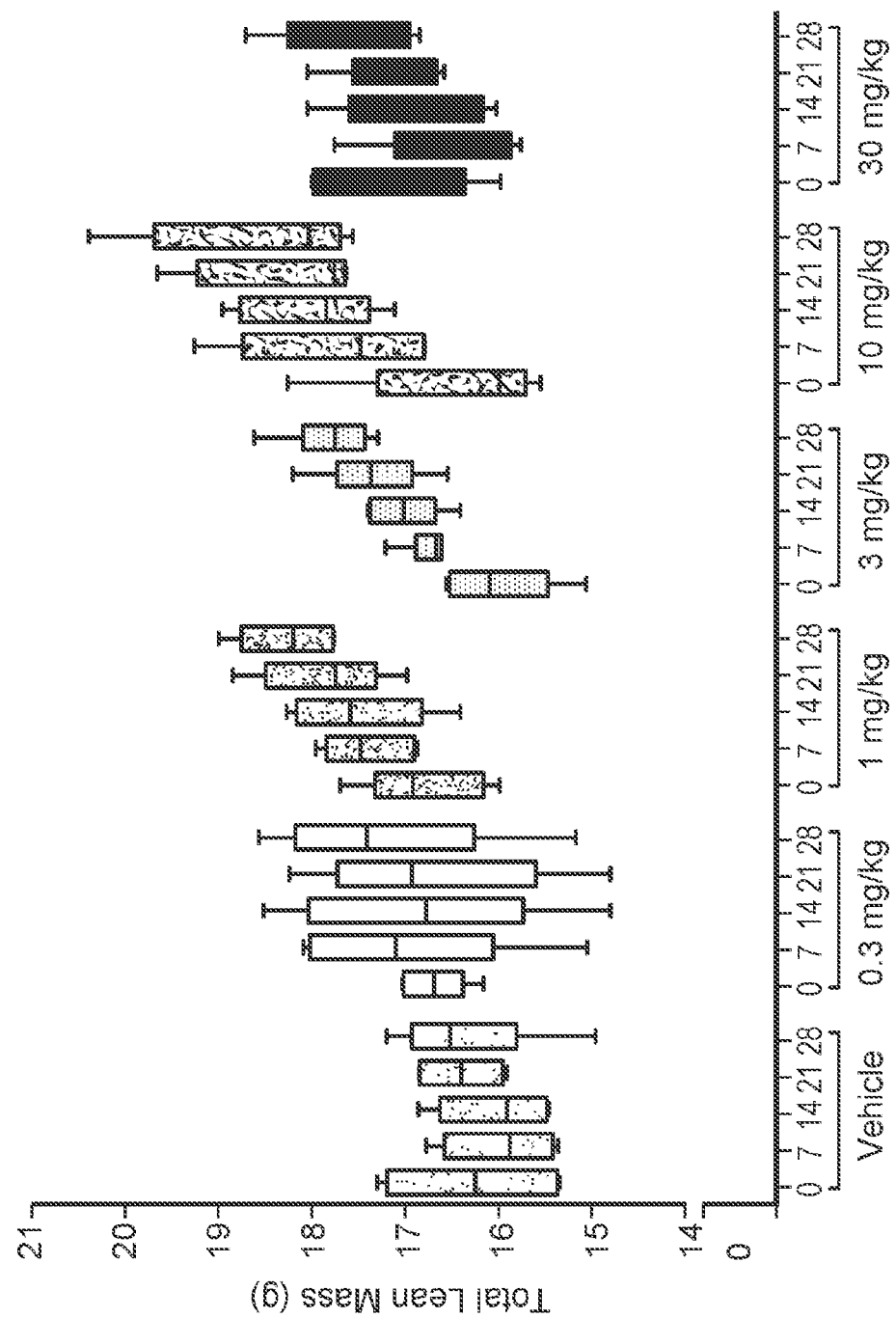

FIG. 12A

Anti-GDF-8 antibody OGD1.0.0 heavy chain (SEQ ID NO:58) containing VH0 VH region

```
EVQLLESGGG LVQPGGSLRL SCAASGFTFS SYAMSWVRQA PGKGLEWVST ISSGGSYTSY   60
PDSVKGRFTI SRDNSKNTLY LQMNSLRAED TAVYYCAKQD YAMNYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGAPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK
```

FIG. 12B

Anti-GDF-8 antibody OGD1.0.0 light chain (SEQ ID NO:59) containing VL0 VL region

```
DIQMTQSPSS LSASVGDRVT ITCKASQDVS TAVAWYQQKP GKAPKLLIYS ASYRYTGVPS   60
RFSGSGSGTD FTLTISSLQP EDFATYYCQQ HYSTPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC
```

ANTAGONIST ANTIBODIES AGAINST GDF-8 AND USES THEREFOR

CROSS-REFERENCE TO RELATED APPLICATION

This application is a continuation of U.S. patent application Ser. No. 13/916,379, filed Jun. 12, 2013, now U.S. Pat. No. 8,992,913, which claims priority to U.S. Provisional Patent Application No. 61/660,232, filed Jun. 15, 2012. The disclosure of each of the prior applications is considered part of and is incorporated herein by reference in their entirety in the disclosure of this application.

REFERENCE TO SEQUENCE LISTING

The instant application contains a Sequence Listing which was submitted in ASCII format in U.S. patent application Ser. No. 13/916,379, now U.S. Pat. No. 8,992,913, which was filed on Jun. 12, 2013, and is hereby incorporated by reference in its entirety. Said ASCII copy, created on Jun. 12, 2013, is named PC071914_SEQLIST_25.txt and is 73,208 bytes in size.

BIOLOGICAL DEPOSIT

Representative materials of the present disclosure were deposited in the American Type Culture Collection ("ATCC"), 10801 University Boulevard, Manassas, Va. 20110-2209, USA, on 14 Jun. 2012. Vector OGD1.0.0-HC having ATCC Accession No. PTA-12980 is a polynucleotide encoding the OGD1.0.0 heavy chain variable region, and vector OGD1.0.0-LC having ATCC Accession No. PTA-12981 is a polynucleotide encoding the OGD1.0.0 light chain variable region.

The deposits are made under the provisions of the Budapest Treaty on the International Recognition of the Deposit of Microorganisms for the Purpose of Patent Procedure and Regulations thereunder ("Budapest Treaty"). This assures maintenance of a viable culture of the deposit for 30 years from the date of deposit. The deposit will be made available by ATCC under the terms of the Budapest Treaty and subject to an agreement between Pfizer Inc. and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions the materials will be promptly replaced on notification with another of the same. Availability of the deposited material is not to be construed as a license to practice the invention in contravention of the rights granted under the authority of any government in accordance with its patent laws.

BACKGROUND OF THE INVENTION

Growth and differentiation factor-8 (GDF-8), also know as myostatin, is a secreted protein and member of the transforming growth factor-beta (TGF-β) superfamily of structurally related growth factors. Members of this superfamily possess growth-regulatory and morphogenetic properties (Kingsley et al. (1994) *Genes Dev.* 8:133-46; Hoodless et al. (1998) *Curr. Topics Microbiol. Immunol.* 228:235-72). Human GDF-8 is synthesized as a 375 amino acid precursor protein that forms a homodimer complex. During processing, the amino-terminal propeptide, known as the "latency-associated peptide" (LAP), is cleaved and may remain noncovalently bound to the homodimer, forming an inactive complex designated the "small latent complex" (Miyazono et al. (1988) *J. Biol. Chem.* 263:6407-15; Wakefield et al. (1988) *J. Biol. Chem.* 263:7646-54; Brown et al. (1999) *Growth Factors* 3:35-43; Thies et al. (2001) *Growth Factors* 18:251-59; Gentry et al. (1990) *Biochemistry* 29:6851-57; Derynck et al. (1995) *Nature* 316:701-05; Massague (1990) *Ann. Rev. Cell Biol.* 12:597-641). Proteins such as follistatin and its relatives also bind mature GDF-8 homodimers and inhibit GDF-8 biological activity (Gamer et al. (1999) *Dev. Biol.* 208:222-32).

An alignment of the deduced GDF-8 amino acid sequence from various species demonstrates that GDF-8 is highly conserved (McPherron et al. (1997) *Proc. Natl. Acad. Sci. U.S.A.* 94:12457-61). The sequences of human, mouse, rat, porcine, and chicken GDF-8 are 100% identical in the C-terminal region, while baboon, bovine, and ovine GDF-8 differ by a mere 3 amino acids at the C-terminus. The high degree of GDF-8 conservation across species suggests that GDF-8 has an essential physiological function.

GDF-8 has been shown to play a major role in the regulation of muscle development and homeostasis by inhibiting both proliferation and differentiation of myoblasts and satellite cells (Lee and McPherron (1999) *Curr. Opin. Genet. Dev.* 9:604-07; McCroskery et al. (2003) *J. Cell. Biol.* 162:1135-47). It is expressed early in developing skeletal muscle, and continues to be expressed in adult skeletal muscle, preferentially in fast twitch types. Additionally, GDF-8 overexpressed in adult mice results in significant muscle loss (Zimmers et al. (2002) *Science* 296:1486-88). Also, natural mutations that render the GDF-8 gene inactive have been shown to cause both hypertrophy and hyperplasia in both animals and humans (Lee and McPherron (1997) supra). For example, GDF-8 knockout transgenic mice are characterized by a marked hypertrophy and hyperplasia of the skeletal muscle and altered cortical bone structure (McPherron et al. (1997) *Nature* 387:83-90; Hamrick et al. (2000) *Bone* 27:343-49). Similar increases in skeletal muscle mass are evident in natural GDF-8 mutations in cattle (Ashmore et al. (1974) *Growth* 38:501-07; Swatland et al. (1994) *J. Anim. Sci.* 38:752-57; McPherron et al., supra; Kambadur et al. (1997) *Genome Res.* 7:910-15). In addition, various studies indicate that increased GDF-8 expression is associated with HIV-induced muscle wasting (Gonzalez-Cadavid et al. (1998) *Proc. Natl. Acad Sci. U.S.A.* 95:14938-43). GDF-8 has also been implicated in the production of muscle-specific enzymes (e.g., creatine kinase) and myoblast proliferation (WO 00/43781).

In addition to its growth-regulatory and morphogenetic properties, GDF-8 is believed to participate in numerous other physiological processes, including glucose homeostasis during type 2 diabetes development, impaired glucose tolerance, metabolic syndromes (i.e., a syndrome such as, e.g., syndrome X, involving the simultaneous occurrence of a group of health conditions, which may include insulin resistance, abdominal obesity, dyslipidemia, hypertension, chronic inflammation, a prothrombotic state, etc., that places a person at high risk for type 2 diabetes and/or heart disease), insulin resistance (e.g., resistance induced by trauma such as burns or nitrogen imbalance), and adipose tissue disorders (e.g., obesity, dyslipidemia, nonalcoholic fatty liver disease, etc.) (Kim et al. (2000) *Biochem. Biophys. Res. Comm.* 281:902-06).

A number of human and animal disorders are associated with functionally impaired muscle tissue, e.g., amyotrophic lateral sclerosis ("ALS"), muscular dystrophy ("MD"; including Duchenne's muscular dystrophy), muscle atrophy, organ atrophy, frailty, congestive obstructive pulmonary disease (COPD), sarcopenia, cachexia, and muscle wasting syndromes caused by other diseases and conditions. Currently, few reliable or effective therapies exist to treat these disorders. The pathology of these diseases indicates a potential role for GDF-8 signaling as a target in the treatment of these diseases.

ALS is a late onset and fatal neurodegenerative disease characterized by degeneration of the central nervous system and muscle atrophy. ALS typically initiates with abnormalities in gait and loss of dexterity, and then progresses to paralysis of limbs and diaphragm. While most cases of ALS are sporadic and are of unknown etiology, 5-10% of cases have been shown to result from dominant familial (FALS) inheritance. Approximately 10-20% of FALS cases are attributed to mutations in the Cu/Zn superoxide dismutase (SOD1) gene (reviewed in Bruijn et al. (2004) *Ann. Rev. Neurosci.* 27:723-49). SOD1 is a heterodimeric metalloprotein that catalyzes the reaction of superoxide into hydrogen peroxide and diatomic oxygen, and as loss of SOD1 does not result in motor neuron disease (Reaume et al. (1996) *Nat. Genet.* 13:43-47), it is believed to induce disease by toxic gain of function (reviewed in Bruijn et al., supra). The specific mechanisms of SOD1-induced neuronal cell death are unclear, and may involve alterations in axonal transport, cellular responses to misfolded protein, mitochondrial dysfunction, and excitotoxicity (Bruijn et al., supra).

The degeneration of motor neurons observed in ALS may occur via multiple mechanisms, including uptake or transport disruption of trophic factors by motor neurons (reviewed in Holzbaur (2004) *Trends Cell Biol.* 14:233-40). Thus, ALS might be treated by therapies that rejuvenate a degenerating neuron by providing an optimal survival environment. A nerve's environment includes nonneuronal cells such as glia and the muscle cells innervated by the motor neuron. This environment provides trophic and growth factors that are endocytosed by the neuron and transported via retrograde axonal transport to the cell body (Chao (2003) *Neuron* 39:1-2; Holzbaur, supra).

FALS has been modeled in both mouse and rat by the overexpression of mutant SOD1 (Howland et al. (2002) *Proc. Natl. Acad. Sci. U.S.A.* 99:1604-09). Transgenic mice overexpressing the G93A form of mutant SOD1 display muscle weakness and atrophy by 90 to 100 days of age, and typically die near 130 days of age (Gurney et al. (1994) *Science* 264:1772-75). However, the underlying SODG93A-induced pathology, which includes grip strength weakness and loss of neuromuscular junctions, is significant as early as 50 days of age (Frey et al. (2000) *J. Neurosci.* 20:2534-42; Fisher et al. (2004) *Exp. Neuro.* 185:232-40; Ligon et al. (2005) *NeuroReport* 16:533-36; Wooley et al. (2005) *Muscle Nerve* 32:43-50). Transgenic rats expressing the SODG93A mutation follow a similar time course of degeneration (Howland et al., supra). Recent work has suggested that the development of pathology is not cell autonomous, consistent with the hypothesis that the degeneration of motor neurons observed in ALS occurs via multiple mechanisms, including the disruption of uptake and transport of trophic factors by the motor neuron (see above). Clement and coworkers have used chimeric mice to show that wild type nonneuronal cells can extend survival of motor neurons expressing mutant SOD1 (Clement et al. (2003) *Science* 302:113-17). These observations have led to the investigation of therapies that might slow neuronal degeneration by providing an optimal microenvironment for survival. For example, treatment of the SODG93A mouse via direct intramuscular injection of virally expressed growth factors (including IGF-1, GDNF and VEGF) prolongs animal survival (Kaspar et al. (2003) *Science* 301:839-42; Azzouz et al. (2004) *Nature* 429:413-17; Wang et al. (2002) *J. Neurosci.* 22:6920-28). In addition, muscle-specific expression of a local IGF-1-specific isoform (mIGF-1) stabilizes neuromuscular junctions, enhances motor neuron survival and delays onset and progression of disease in the SODG93A transgenic mouse model, indicating that direct effects on muscle can impact disease onset and progression in transgenic SOD1 animals (Dobrowolny et al. (2005) *J. Cell Biol.* 168:193-99). Links between muscle hypermetabolism and motor neuron vulnerability have also been reported in ALS mice, supporting the hypothesis that defects in muscle may contribute to the disease etiology (Dupois et al. (2004) *Proc. Natl. Acad Sci. U.S.A.* 101:11159-64). Thus, enhancing muscle growth should provide improved local support for motor neurons, and therefore result in therapeutic benefits.

Inhibition of myostatin expression leads to both muscle hypertrophy and hyperplasia (Lee and McPherron, supra; McPherron et al., supra). Myostatin negatively regulates muscle regeneration after injury, and lack of myostatin in GDF-8 null mice results in accelerated muscle regeneration (McCroskery et al., (2005) *J. Cell. Sci.* 118:3531-41). Myostatin-neutralizing antibodies increase body weight, skeletal muscle mass, and muscle size and strength in the skeletal muscle of wild type mice (Whittemore et al. (2003) *Biochem. Biophys. Res. Commun.* 300:965-71) and the mdx mouse, a model for muscular dystrophy (Bogdanovich et al. (2002) *Nature* 420:418-21; Wagner et al. (2002) *Ann. Neurol.* 52:832-36). Furthermore, myostatin antibody in these mice decreased the damage to the diaphragm, a muscle that is also targeted during ALS pathogenesis. It has been hypothesized that the action of growth factors, such as HGF, on muscle may be due to inhibition of myostatin expression (McCroskery et al. (2005), supra), thereby helping to shift the "push and pull," or balance, between regeneration and degeneration in a positive direction. Thus, GDF-8 inhibition presents as a potential pharmacological target for the treatment of ALS, muscular dystrophy (MD), and other GDF-8-associated disorders, e.g., neuromuscular disorders for which it is desirable to increase muscle mass, strength, size, etc. With the availability of animal models (mouse and rat) of ALS, it is possible to test therapeutics in two different species, thus increasing the confidence of therapeutic effects in humans in vivo.

In addition to neuromuscular disorders in humans, there are also growth factor-related conditions associated with a loss of bone, such as osteoporosis and osteoarthritis, which predominantly affect the elderly and/or postmenopausal women. In addition, metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. Although many current therapies for these conditions function by inhibiting bone resorption, a therapy that promotes bone formation would be a useful alternative treatment. Because GDF-8 plays a role in bone development as well as muscular development, regulation of GDF-8 is also an excellent pharmacological target for the treatment of bone-degenerative disorders.

A murine monoclonal antibody that specifically antagonizes GDF-8 was previously described as increasing muscle mass and strength in a rodent model for ALS, among other biological effects. Holzbaur, E L, et al., Myostatin inhibition slows muscle atrophy in rodent models of amyotrophic lateral sclerosis, Neurobiology of Disease (2006) 23(3):697-707. The mouse antibody and its humanized counterpart are therefore expected to be effective in increasing muscle mass and strength in ALS patients, as well as in patients affected by other diseases and disorders characterized or mediated by excess quantities of GDF-8, such as those described above.

The humanized version of the mouse anti-GDF-8 antibody mentioned above, like many monoclonal antibodies and other protein-based therapeutics, is challenging and expensive to manufacture because doing so typically requires production in living mammalian cells. Improving the yield of this antibody, or others with similar specificity, would therefore permit the production of the same amount of active drug with fewer inputs. This would have the dual benefit of reducing the cost of manufacturing while at the same time freeing up limited manufacturing facilities for the production of other biological drugs. Both benefits would further the goals of increasing the availability to patients of therapeutic anti-GDF-8 antibodies as well as other biologics. Accordingly, there exists a need in the art for improved versions of anti-GDF-8 antibodies having higher production yields in mammalian cells.

SUMMARY OF THE INVENTION

The present disclosure provides humanized anti-GDF-8 antibodies, or antigen binding fragments thereof, that are capable of being expressed at higher levels in host cells compared to prior versions of such antibodies sharing the same complementarity determining regions (CDRs). Also provided are compositions comprising such antibodies for use in the methods of the present disclosure.

In certain embodiments, these antibodies have a variable heavy (VH) region in which CDR1 is defined by the amino acid sequence of SEQ ID NO:10 or SEQ ID NO:20, CDR2 is defined by the amino acid sequence of SEQ ID NO:11 or SEQ ID NO:21, CDR3 is defined by the amino acid sequence of SEQ ID NO:12, and in which the VH region is modified so that the amino acid at Kabat position 108 is leucine instead of methionine. In other embodiments, these antibodies have a VH region comprising the same CDRs and in which the fourth framework region of the VH region comprises amino acids 106-116 of SEQ ID NO:44. In yet other embodiments of these antibodies, the CDRs are grafted onto human germline VH gene segment DP-47 and then joined with the JH4 human heavy J segment gene. And in yet other embodiments, the VH region of these antibodies comprises the amino acid sequence of SEQ ID NO:44.

Antibodies of the present disclosure having a leucine at Kabat position 108, such as those exemplified above, are characterized by increased expression levels compared to versions in which methionine occurs at the same position. In certain embodiments, the former version is expressed at higher levels under similar conditions compared to the latter by an amount greater than about 50%, 100%, 150%, 200%, 250%, 300%, 400%, 500%, 600%, 700%, 800%, 900%, 1000%, 1200%, 1400%, 1600%, 1800% or even 2000%.

According to other embodiments of the antibodies of the disclosure, the VH regions described in the previous paragraph may be paired with variable light (VL) regions in which CDR1 is defined by the amino acid sequence of SEQ ID NO:13, CDR2 is defined by the amino acid sequence of SEQ ID NO:14 and CDR3 is defined by the amino acid sequence of SEQ ID NO:15, and in which the amino acid at Kabat position 100 of the VL region is either glycine or glutamine. In other embodiments, the VH region is paired with a VL region in which the light chain CDRs are grafted onto human germline VL gene segment DPK-9 and then joined with the JK4 human light J segment gene. According to some other embodiments of these antibodies, the previously described VH regions are paired with VL regions possessing the prior described VL region CDRs and in which the fourth framework region of the VL region comprises amino acids 98-107 of either SEQ ID NO:9 or SEQ ID NO:46. And in yet other embodiments, the previously described VH regions are paired with VL regions comprising the amino acid sequence of either SEQ ID NO:9 or SEQ ID NO:46.

In some other embodiments, the VH regions described above are joined to heavy chain constant regions from human antibody subtypes including IgA, IgG, IgD, IgE, or IgM. Where the heavy chain constant region is from IgG, in yet other embodiments, the antibody heavy chain constant regions are from the IgG subtypes of IgG1, IgG2, IgG3 or IgG4. Heavy chain constant regions can be modified to, for example, abrogate one or more Fc domain effector functions, as exemplified in SEQ ID NO:57. In other embodiments, the VL regions described above are joined to light chain constant regions, which may be of the lambda or kappa subtypes.

According to other embodiments, the VH region of SEQ ID NO:44 is joined with the modified heavy region of the amino acid sequence of SEQ ID NO:57 to create the full length antibody heavy chain of the amino acid sequence of SEQ ID NO:58. Conversely, in other embodiments, the VL region of SEQ ID NO:46 can be joined with the kappa constant light chain of the amino acid sequence of SEQ ID NO:17 to create the full length antibody light chain of the amino acid sequence of SEQ ID NO:59. In other embodiments, two each of the full length antibody heavy and light chains can then be combined to create an anti-GDF-8 antibody having two antigen binding sites. And in yet other embodiments, antibodies can comprise fragments or derivatives of such full size intact antibodies, including for example an Fab, an F(ab')$_2$, an scFv, an scFv-Fc, an scFv-CH, an scFab, an scFv-zipper, a diabody, a triabody, a tetrabody, a minibody, an Fv, and a bispecific antibody.

Antibodies of the disclosure can have a range of binding affinities for GDF-8, for example, about 5000 nM, or even higher, for example, at least about 4000 nM, 3000 nM, 2000 nM, 1000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM or 0.001 nM.

The disclosure also provides nucleic acids encoding the anti-GDF-8 antibodies, as well as expression vectors comprising such nucleic acid sequences, and host cells for expressing the antibodies.

The present disclosure also provides methods useful for treating or preventing in patients muscular disorders characterized by diminished muscle mass or strength. Such methods are carried out by administering to patients in need of treatment or prevention of such disorders a therapeutically or prophylactically effective amount of a composition comprising an antibody, or antigen binding fragment thereof, that specifically binds to GDF-8. Antibodies useful for these methods include those described above and throughout this disclosure.

According to certain embodiments, antibody compositions of the present disclosure can be administered in therapeutically or prophylactically effective amounts to a patient in need of treatment or prevention of a muscular disorder including those selected from among the group consisting of muscular dystrophy, muscle atrophy, sarcopenia, cachexia, muscle wasting syndrome, age-related loss of muscle mass or strength, and frailty. In other embodiments, the muscular disorder is cachexia caused by cancer. In yet other embodiments, the muscular disorder is Duchenne muscular dystrophy. And in certain of the latter embodiments, administration of the anti-GDF-8 antibodies is effective to improve the patient's performance in the 6 minute walk test.

In some embodiments, it is also useful to treat a patient suffering from muscular dystrophy, for example Duchenne muscular dystrophy, by administering a composition comprising an antibody of the present disclosure before, concurrently with or after another agent effective to treat muscular dystrophy. In certain embodiments, such an agent is a glucocorticoid, such as prednisone.

Methods are also provided for increasing the mass or strength of a muscle of a mammal by administering to a mammal a composition comprising an anti-GDF-8 antibody of the disclosure in an amount effective to increase the mass or strength of the mammal's muscle. In a number of embodiments, the muscle is a skeletal muscle, including one or more active in breathing, or cardiac muscle.

Methods are also provided for treating or preventing neuromuscular disorders by administering to a subject in need of treatment or prevention of a neuromuscular disorder a therapeutically or prophylactically effective amount of an anti-GDF-8 antibody of the present disclosure. In certain embodiments, the neuromuscular disorder to be treated or prevented is ALS.

Methods are also provided for treating or preventing metabolic disorders by administering to a subject in need of treatment or prevention of metabolic disorders a therapeutically or prophylactically effective amount of an anti-GDF-8 antibody of the present disclosure. In a number of embodiments, the metabolic disorders to be treated or prevented include type 2 diabetes mellitus, metabolic syndrome, syndrome X, insulin resistance, and impaired glucose tolerance.

Methods are also provided for treating or preventing adipose tissue disorders by administering to a subject in need of treatment or prevention of adipose tissue disorders a therapeutically or prophylactically effective amount of an anti-GDF-8 antibody of the present disclosure. In a number of embodiments, the adipose tissue disorders to be treated or prevented include obesity and abnormally high body mass index.

Methods are also provided for treating or preventing bone loss disorders by administering to a subject in need of treatment or prevention of bone loss disorders a therapeutically or prophylactically effective amount of an anti-GDF-8 antibody of the present disclosure. In a number of embodiments, the bone loss disorders to be treated or prevented include osteoporosis, osteopenia, osteoarthritis, and osteoporosis-related bone fractures.

In some other embodiments, anti-GDF-8 antibodies useful for the methods of the disclosure include antibodies conjugated to moieties that usefully alter their function or characteristics, for example, but not limited to, increasing serum half life. In yet other embodiments, amino acid changes can be effected for a similar purpose, or other purposes.

Antibody compositions for use in the methods of the disclosure can be prepared as different formulations, including, but not limited to, an aqueous suspension, for administration by a variety of routes, including, but not limited to, subcutaneous administration, intravenous administration, intramuscular administration, intraperitoneal administration, infusion administration, or bolus administration.

In some embodiments, an effective dose the anti-GDF-8 antibodies of the disclosure ranges from 0.001 mg/kg to about 250 mg/kg, which may be given in one administration, or over multiple, spaced administrations.

The disclosure also provides pharmaceutical kits for use by clinicians and others to facilitate administration of anti-GDF-8 antibody compositions to patients. In some embodiments, kits include an anti-GDF-8 antibody of the disclosure in either lyophilized form or as an aqueous solution, a diluent, such as pharmaceutical grade water or buffer, and a device for administering the anti-progastrin antibody, such as a syringe and needle. In other embodiments, kits may additionally include a second therapeutic agent.

BRIEF DESCRIPTION OF THE DRAWINGS

FIG. 1A provides an alignment of the amino acid sequences of the VH regions from certain anti-GDF-8 antibodies of the disclosure, including a murine antibody VH region and two humanized antibody VH regions created by grafting the murine heavy chain CDRs into the human germline VH region DP-47 (i.e., VH0 and VH1). Additionally provided is an alignment of the amino acid sequences of the further humanized VH regions VH2-VH5. The amino acid sequence of the heavy chain CDRs is highlighted using bold underlined font. The amino acid at Kabat position 108 is highlighted using bold font beneath an asterisk.

FIG. 1B provides an alignment of the amino acid sequences of the VL regions from certain anti-GDF-8 antibodies of the disclosure, including a murine antibody VL region and two humanized antibody VL regions created by grafting the murine light chain CDRs into the human germline VL region DPK-9 (i.e., VL0 and VL1). Additionally provided is an alignment of the amino acid sequences of the further humanized VL regions VL2-VL5. The amino acid sequence of the light chain CDRs is highlighted using bold underlined font. The amino acid at Kabat position 100 is highlighted using bold font beneath an asterisk.

FIG. 2B additionally shows the percentage increase in muscle mass of the extensor digitalis longus (EDL) from the same groups of antibody treated and control mice.

FIG. 4A provides a graph showing the dose responsive increase in mass of gastrocnemius (Gastroc) and quadriceps (Quad) muscles from C57Bl/6 mice treated weekly for four weeks with PBS vehicle, and 0.3, 1, 3, 10 and 30 mg/kg OGD1.0.0 antibody. Data represents the muscle mass measured at the end of four weeks.

FIG. 5A provides a graph showing the dose responsive increase in total body lean mass of C57Bl/6 mice treated weekly for four weeks with PBS vehicle, and 0.3, 1, 3, 10 and 30 mg/kg OGD1.0.0 antibody. Data represents lean mass measured at the end of each week over four weeks.

FIG. 12A provides the amino acid sequence of an exemplary anti-GDF-8 antibody heavy chain containing the variable heavy region referred to herein as VH0.

FIG. 12B provides the amino acid sequence of an exemplary anti-GDF-8 antibody light chain containing the variable light region referred to herein as VL0.

DETAILED DESCRIPTION

Figure 2A:
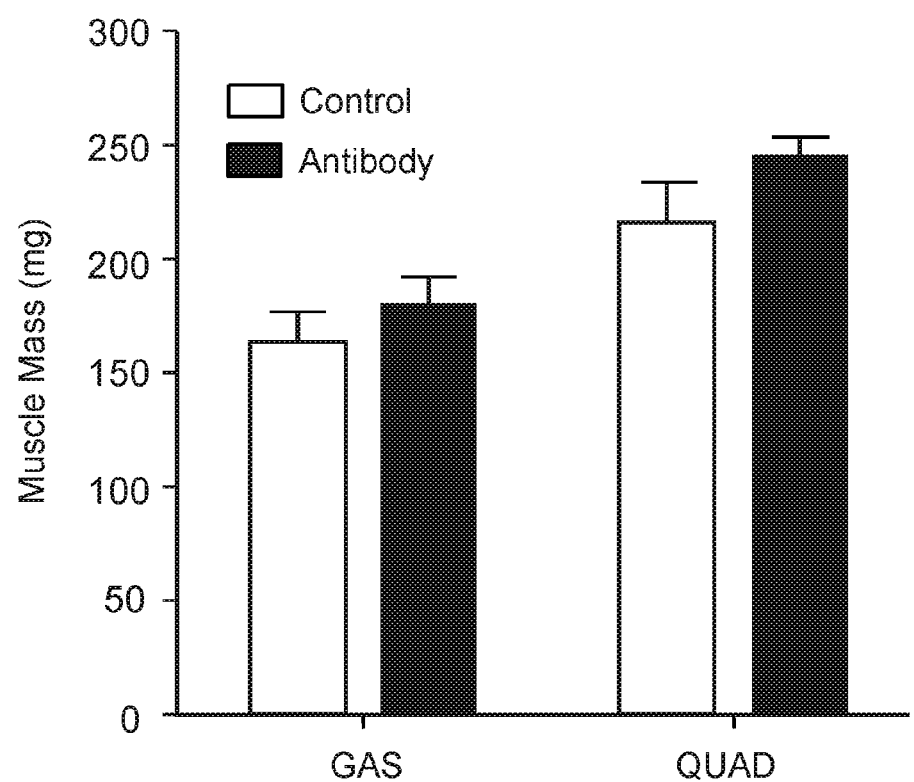
FIG. 2A provides a graph showing the increase in mass of the gastrocnemius (GAS) and quadriceps (QUAD) muscles from C57Bl/6 mice treated for two weeks with 10 mg/kg OGD1.0.0 antibody compared to vehicle control.

The present disclosure provides improved versions of a humanized anti-GDF-8 antibody capable of being expressed in cells at much higher levels compared to prior versions of the antibody. Accordingly, the improved versions of the anti-GDF-8 antibody described herein are expected to be able to be produced in greater quantities and for lower cost of goods given the same inputs compared to earlier versions. The present disclosure also describes various methods of treatment or prevention using the improved antibodies.

Thus, in certain exemplary non-limiting embodiments, the improved anti-GDF-8 antibodies can be used to treat muscular dystrophies, cachexia and other disorders where increasing a subject's muscle mass or strength is expected to confer therapeutic benefit.

Antibody Structure and Diversity

As used herein, the term antibody refers to an intact immunoglobulin (Ig) or any antigen binding fragment, part or portion thereof and encompasses, among other things, any polypeptide comprising a complete or partial antigen binding site retaining at least some antigen binding specificity. Antibody may also refer to a combination of antigen binding fragments, parts or portions derived from an intact antibody with another molecule, including a different antibody, protein from the Ig superfamily, or proteins or other types of molecules that do not originate in the immune system. Such antibody derivatives may include portions or moieties that are not proteinaceous.

Antigen refers to a substance, protein or otherwise, capable of being specifically bound by an antibody. An antigen may have more than one antigenic determinant or epitope, which is the portion of the antigen that is bound by an antibody.

Immunoglobulins (Ig) are heterotetrameric proteins comprising two heavy chains of approximately 50 kDa each, and two light chains of approximately 25 kDa each. Each chain comprises multiple Ig domains. Starting at the amino terminus the heavy chain contains a single variable region (VH) followed, depending on the Ig subtype, by three or four constant regions called CH1, CH2, CH3 and, when present, CH4. Similarly, in the light chain a single variable region (VL) is positioned at the amino terminus of the polypeptide followed by a single constant region (CL). Between the CH1 and CH2 regions is a hinge region of variable length, depending on isotype, which imparts flexibility to the molecule. The heavy chain carboxy-terminal of CH1, including the hinge, CH2, CH3 and, when present, CH4, constitutes the Fc region. Each variable or constant region comprises a single Ig domain.

Ig light chains bind to Ig heavy chains, and pairs of Ig heavy chains bind to each other, via disulfide bonds. Non-covalent interactions may also contribute to stabilizing inter-chain quarternary structure between heavy and light chains and between paired heavy chains. In intact Ig molecules, the VH and VL regions of paired heavy and light chains are positioned adjacent to each other and interact and cooperate to form the antigen binding site. Because intact Ig molecules contain two pairs of paired heavy and light chains, i.e., a total of two heavy and two light chains, Ig molecules contain two antigen binding sites. The presence of the hinge region confers flexibility between the antigen binding sites and remainder of the molecule.

Heavy and light chain constant regions do not directly participate in antigen recognition. However, the heavy chain, in particular the Fc region, contains sequences capable of interacting with effector molecules and cells of the immune system, thereby allowing the heavy constant regions to mediate important biological functions of the Ig molecules.

The variable regions of both heavy and light chains contain three spaced areas of heightened amino acid variability, called hypervariable regions or complementarity determining regions (CDR), which vary extensively across different Ig molecules compared to the more highly conserved framework regions (FR) which surround the CDRs. From the amino terminus of a variable region, the sequential order and numbering of FRs and CDRs is FR1, CDR1, FR2, CDR2, FR3, CDR3, and FR4. The framework regions are principally responsible for determining the tertiary structure of the variable region Ig domain. By contrast, the CDRs form loops extending outward from each variable region. The CDRs of adjacent VH and VL regions cooperate to form an antigen binding surface that is principally responsible for defining the antigen binding specificity of particular Ig molecules.

Researchers studying antibody structure and function have developed different schema for identifying the heavy and light chain CDRs existing within the amino acid sequence of any particular VH or VL region. Many of these schema identify CDRs according to invariant or nearly invariant patterns associated with the surrounding framework of variable heavy and light regions. The CDRs are then defined using number ranges corresponding to the position of their constituent residues within the context of the VH and VL regions. Because CDRs, in particular the third CDR, can vary in length, the schemes sometimes also use letters to define constituent residues. One of the first such schemes is known as the Kabat numbering system, which was based on aligning the then known VH and VL sequences to determine the position of variable CDR subsequences within the context of the more highly conserved framework regions. Other schema for defining CDRs include the AbM numbering system and the Chothia numbering system. Other schema are also possible. For example, a CDR may be defined as those variable region residues that contact antigen, even if such residues do not fall neatly into the more formalized definitions for CDR, such as the Kabat or Chothia numbering schemes. See, e.g., Y. Ofran, et al., Automated identification of complementarity determining regions (CDRs) reveals peculiar characteristics of CDRs and B cell epitopes, J Immunol. 2008 Nov. 1; 181(9):6230-5, which is incorporated by reference. The Kabat numbering scheme and certain other antibody numbering schemes are described in more detail in, for example, the Handbook of Therapeutic Antibodies (2007), ed. Stefan Dubel, Wiley-VCH Verlag GmbH & Co. KgaA, Weinheim, which is incorporated by reference.

Amino acids within CDRs of the variable heavy and light regions contact residues in the antigen and are principally responsible for defining the binding specificity of the antibody for the antigen. Depending on the antibody-antigen pair under study, all or fewer than all the CDR residues may directly contact the antigen. Furthermore, certain contacts may contribute more than others to defining specificity and/or affinity.

The identity of contact residues, both in the antibody and antigen, can be determined using x-ray crystallography or other methods known to those skilled in the art. Often, but not always, mutation of such contact residues will negatively affect antigen binding specificity and/or affinity. Conversely, it may be possible to mutate non-contacting CDR residues, as well as FR residues, without substantially impacting antigen binding specificity or affinity. Although it is expected that conservative amino acid changes are more likely to preserve antigen binding specificity and affinity, the actual effect of any particular CDR or framework mutation can be determined empirically using techniques familiar to those of ordinarily skill in the art.

Although the CDRs of VH and VL regions, supported by their respective framework regions, are typically responsible for establishing antigen binding specificity and affinity, there may be exceptions. For example, in certain Ig molecules, FR residues might also contribute to antigen binding, whereas in certain other Ig molecules, one or more of the CDRs may not directly contact antigen. Furthermore, in yet other Ig molecules, the CDRs of an isolated VH region VL region may possess substantial antigen binding specificity even in the absence of the corresponding variable region with which it would ordinarily be paired. The capability of certain isolated Ig molecule variable regions to specifically bind antigen is analogous to the antigen binding specificity of shark or camelid antibodies, which comprise paired heavy chains, but no light chains.

The Ig molecules of certain species can be classified according to different isotypes. For example, in humans, Ig isotypes include IgA, IgG, IgD, IgE, and IgM. Further the IgA and IgG isotypes can be classified into subtypes called, respectively, IgA1 and IgA2, and IgG1, IgG2, IgG3, and IgG4. Isotypes and subtypes are defined by differences in the amino acid sequences of the heavy chain constant regions. As a result, the different isotypes and subtypes are capable of interacting with different effector molecules on different immune cells thereby conferring different effector functions. For example, IgA molecules contribute to muscosal immunity, whereas IgE molecules contribute to immunity against certain parasites. The heavy chains of IgM and IgE contain four tandemly arranged CH Ig domains numbered, starting from the amino terminal CH region, CH1, CH2, CH3, and CH4. IgA, IgD and IgG, however, only contain three tandemly arranged CH regions. Light chain constant regions comprise two isotypes, called kappa and lambda, having no known biological effector functions. A naturally occurring Ig molecule will possess only a single light chain constant region isotype.

The genes expressing antibody heavy and light chains are constructed in vivo through multiple gene rearrangements known as V(D)J recombination. This process is responsible for generating a large repetoire of antigen binding proteins from a comparatively limited repetoire of gene sequences residing in the genome. More information about this process is described in Abbas, A. K., Lichtman, A. H. and Pillai, S., 2010, *Cellular and Molecular Immunology*, 6$^{th}$ Ed., Chapter 8, Saunders, Philadelphia, Pa., which is incorporated by reference in its entirety.

In human germline DNA, three separate gene loci encode the exons necessary to construct immunoglobulin heavy chains, kappa light chains and lambda light chains. The heavy chain locus resides on chromosome 14, the kappa chain locus resides on chromosome 2 and the lambda chain locus resides on chromosome 22. At the 5' end of each locus lie multiple variable (V) gene segments, each about 300 base pairs long, which encode the majority of amino acids constituting the variable region of antibody heavy and light chains, including both the first and second complementarity determining regions (CDR1 and CDR2). In humans, there are about 100 V genes in the heavy chain locus, about 35 V genes in the kappa chain locus and about 30 V genes in the lambda chain locus. The V gene segments are separated from each other by introns.

Situated downstream of the V segments and upstream of the constant (C) gene segments in the human heavy chain locus and kappa light chain locus are clusters of joining (J) segments, typically about 30-50 base pairs long and separated from each other and the neighboring V and C genes by non-coding sequence. The heavy chain locus contains a cluster of six functional J segments upstream from the nine functional C genes associated with the different Ig isotypes, and the kappa light chain locus contains a cluster of five J segments upstream of the single $C_\kappa$ gene. The human lambda light chain locus also contains four functional J segments, but each is located 5' of one of four corresponding functional $C_\lambda$ genes. The human heavy chain locus also contains a cluster of more than 20 diversity (D) gene segments located downstream of the V genes and upstream of the J segment cluster. Neither of the light chain loci contain D gene segments.

In a mature Ig light chain gene, the V region is encoded by the V and J segments, whereas in the Ig heavy chain, the V region is encoded by the V, J and D gene segments. CDR1 and CDR2 in both heavy and light chains are encoded by the V gene segment. Constructing the CDR3 is more complicated, however. For the heavy chain, CDR3 is encoded by the VDJ junction, including the D and J segments and junctional residues. Similarly, the CDR3 of the light chain is encoded by the VJ junction, including the J segment and junctional residues.

In immature B cells, all the V, D, and J gene segments lie separate in the germline and cannot be used to express functional Ig proteins. Instead, as B cells mature, the gene segments undergo a complex DNA rearrangement process known as V(D)J recombination which brings randomly chosen heavy chain V, D and J gene segments, or light chain V and J gene segments, into contiguity. During joining of the V, D and J gene segments, the molecules responsible for carrying out V(D)J recombination randomly add or remove nucleotides between the segments. In this way, complete variable region exons are generated in the genome of mature B cells which are then combined with other exons, including those encoding C regions, in mRNA encoding functional Ig heavy and light chain proteins.

The random combination of different V, D and J gene segments to construct V region exons, and the random addition or removal of nucleotides between the gene segments joining, are both important mechanisms through which the immune system generates the great diversity of antigen binding sites. These phenomenon are respectively called combinatorial diversity and junctional diversity. Because CDR3 is formed from sequences contributed by V, D and J segments in the case of heavy chains or V and J segments in the case of light chains, junctional diversity explains why CDR3 is the most variable of the three CDRs and typically makes the most extensive contact with an antigen.

Because the structure of Ig molecules is essentially modular, with different regions performing different functions, it is possible to prepare fragments or derivatives of anti-GDF-8 antibodies that retain GDF-8 binding capability. Such fragments or derivatives are encompassed by the term antibody as used herein. Non-limiting examples of antigen binding fragments or derivatives prepared from Ig molecules include Fab fragments, which are monovalent fragments comprising the VH, CH1, VL and CL regions; F(ab')2, a bivalent fragment comprising two Fabs joined to each other via the hinge region; an Fd fragment comprising VH and CH1 regions; an Fv fragment comprising VL and VH regions; a dAb fragment, comprising a VH or VL region. Another example is a single chain Fv region (scFv) which comprises a VH and VL region arranged tandemly in a single polypeptide chain and separated a polypeptide linker permitting the variable regions to associate and form a monovalent antigen binding site. Single chain Fv regions may be designed in which the VH region precedes the VL region, or alternatively in which the VL region precedes the VH region. A non-limiting example of a linker is a 15-residue (Gly$_4$Ser)$_3$ peptide (SEQ ID NO:34). Other linkers are also possible. Other fragments or derivatives include Fab', surrobodies, disulfide-stabilized Fv antibodies (dsFv), diabodies, triabodies, and single domain antibodies, such as shark antibody or a camelized antibody or nanobody. Other fragments or derivatives are also possible. Antigen binding fragments, parts or portions such as those described here may be produced recombinantly or by enzymatic or chemical cleavage of intact antibodies.

Exemplary Anti-GDF-8 Antibodies

GDF-8 refers to growth and differentiation factor-8, which is a member of the TGF-β superfamily. The amino acid sequence of mature human GDF-8 is set forth in SEQ ID NO:1.

Prior investigation identified a murine monoclonal antibody with the capability of specifically binding to GDF-8 and neutralizing its biological activity. This antibody was demonstrated to increase muscle mass and strength in mice, including in a mouse model of amyotrophic lateral sclerosis (ALS). See WO 2007/024535, which is incorporated by reference in its entirety. The mouse antibody's VH region has the amino acid sequence of SEQ ID NO:3 and its VL region has the amino acid sequence of SEQ ID NO:4. These VH and VL regions are shown in FIG. 1A and FIG. 1B, respectively, in which the amino acid sequence of each of the VH and VL region CDRs are depicted in bold font. The SEQ ID NOs associated with each VH and VL CDR in both the Kabat and AbM numbering systems are listed in Table 1 set forth below. CDR H1, H2, and H3 as defined under the Kabat numbering system are assigned SEQ ID NO:10, 11 and 12, respectively, whereas CDR L1, L2, and L3 are assigned SEQ ID NO:13, 14, and 15, respectively. Under the AbM numbering system, CDR H1, H2, and H3 are assigned SEQ ID NO:20, 21, and 22, respectively, whereas CDR L1, L2, and L3 are assigned SEQ ID NO:23, 24, and 25, respectively.

TABLE 1

Nucleic acid and amino acid sequences of the disclosure identified by sequence identification numbers

| Seq ID No. | Type | Species | Sequence Description |
| --- | --- | --- | --- |
| 1 | Protein | Human | Mature GDF-8 |
| 2 | DNA | Mouse | Mouse anti-GDF-8 antibody VH region |
| 3 | Protein | Mouse | Mouse anti-GDF-8 antibody VH region |
| 4 | DNA | Mouse | Mouse anti-GDF-8 antibody VL region |
| 5 | Protein | Mouse | Mouse anti-GDF-8 antibody VL region |
| 6 | DNA | Artificial | Humanized anti-GDF-8 antibody VH1 (reverse translated from SEQ ID NO: 7) |
| 7 | Protein | Artificial | Humanized anti-GDF-8 antibody VH1 |
| 8 | DNA | Artificial | Humanized anti-GDF-8 antibody VL1 (reverse translated from SEQ ID NO: 9) |
| 9 | Protein | Artificial | Humanized anti-GDF-8 antibody VL1 |
| 10 | Protein | Mouse | Anti-GDF-8 antibody CDR H1 Kabat numbering system |

TABLE 1-continued

Nucleic acid and amino acid sequences of the disclosure identified by sequence identification numbers

| Seq ID No. | Type | Species | Sequence Description |
|---|---|---|---|
| 11 | Protein | Mouse | Anti-GDF-8 antibody CDR H2 Kabat numbering system |
| 12 | Protein | Mouse | Anti-GDF-8 antibody CDR H3 Kabat numbering system |
| 13 | Protein | Mouse | Anti-GDF-8 antibody CDR L1 Kabat numbering system |
| 14 | Protein | Mouse | Anti-GDF-8 antibody CDR L2 Kabat numbering system |
| 15 | Protein | Mouse | Anti-GDF-8 antibody CDR L3 Kabat numbering system |
| 16 | DNA | Human | Kappa CL region |
| 17 | Protein | Human | Kappa CL region |
| 18 | DNA | Artificial | Human IgG1 CH region with two substitution mutations |
| 19 | Protein | Artificial | Human IgG1 CH region with two substitution mutations |
| 20 | Protein | Mouse | Anti-GDF-8 antibody CDR H1 AbM numbering system |
| 21 | Protein | Mouse | Anti-GDF-8 antibody CDR H2 AbM numbering system |
| 22 | Protein | Mouse | Anti-GDF-8 antibody CDR H3 AbM numbering system |
| 23 | Protein | Mouse | Anti-GDF-8 antibody CDR L1 AbM numbering system |
| 24 | Protein | Mouse | Anti-GDF-8 antibody CDR L2 AbM numbering system |
| 25 | Protein | Mouse | Anti-GDF-8 antibody CDR L3 AbM numbering system |
| 26 | Protein | Artificial | Humanized anti-GDF-8 antibody VH with back mutations |
| 27 | Protein | Artificial | Humanized anti-GDF-8 antibody VL with back mutations |
| 28 | DNA | Mouse | Mouse anti-GDF-8 antibody VH + leader sequence |
| 29 | Protein | Mouse | Mouse anti-GDF-8 antibody VH + leader sequence |
| 30 | DNA | Mouse | Mouse anti-GDF-8 antibody VL + leader sequence |
| 31 | Protein | Mouse | Mouse anti-GDF-8 antibody VL + leader sequence |
| 32 | Protein | Human | DPK-9 germline VL region |
| 33 | Protein | Human | DP-47 germline VH region |
| 34 | Protein | Artificial | Synthetic linker sequence |
| 35 | DNA | Human | JH3 J region (Genbank accession no. X86355) |
| 36 | Protein | Human | JH3 J region (Genbank accession no. X86355) |
| 37 | DNA | Human | JH4 J region (Genbank accession no. J00256) |
| 38 | Protein | Human | JH4 J region (Genbank accession no. J00256) |
| 39 | DNA | Human | JK1 J region (Genbank accession no. J00242) |
| 40 | Protein | Human | JK1 J region (Genbank accession no. J00242) |
| 41 | DNA | Human | JK4 J region (Genbank accession no. J00242) |
| 42 | Protein | Human | JK4 J region (Genbank accession no. J00242) |
| 43 | DNA | Artificial | Humanized anti-GDF-8 antibody VH0 |
| 44 | Protein | Artificial | Humanized anti-GDF-8 antibody VH0 |
| 45 | DNA | Artificial | Humanized anti-GDF-8 antibody VL0 |
| 46 | Protein | Artificial | Humanized anti-GDF-8 antibody VL0 |
| 47 | DNA | Artificial | Humanized anti-GDF-8 antibody VH1 |
| 48 | DNA | Artificial | Humanized anti-GDF-8 antibody VL1 |
| 49 | DNA | Artificial | Humanized anti-GDF-8 antibody VH0 + leader sequence |
| 50 | Protein | Artificial | Humanized anti-GDF-8 antibody VH0 + leader sequence |
| 51 | DNA | Artificial | Humanized anti-GDF-8 antibody VL0 + leader sequence |
| 52 | Protein | Artificial | Humanized anti-GDF-8 antibody VL0 + leader sequence |
| 53 | DNA | Artificial | Humanized anti-GDF-8 antibody VH1 + leader sequence |
| 54 | Protein | Artificial | Humanized anti-GDF-8 antibody VH1 + leader sequence |
| 55 | DNA | Artificial | Humanized anti-GDF-8 antibody VL1 + leader sequence |
| 56 | Protein | Artificial | Humanized anti-GDF-8 antibody VL1 + leader sequence |
| 57 | Protein | Artificial | Human IgG1 CH region with three substitution mutations |
| 58 | Protein | Artificial | Humanized anti-GDF-8 antibody VH0 + human IgG1 CH region with three substitution mutations |
| 59 | Protein | Artificial | Humanized anti-GDF-8 antibody VL0 + human kappa CL region |
| 60 | DNA | Artificial | Anti-GDF-8 scFv-Fc mouse VL – mouse VH |
| 61 | Protein | Artificial | Anti-GDF-8 scFv-Fc mouse VL – mouse VH |
| 62 | DNA | Artificial | Anti-GDF-8 scFv-Fc humanized VL0 – humanized VH0 |
| 63 | Protein | Artificial | Anti-GDF-8 scFv-Fc humanized VL0 – humanized VH0 |
| 64 | DNA | Artificial | Anti-GDF-8 scFv-Fc humanized VH0 – humanized VL0 |
| 65 | Protein | Artificial | Anti-GDF-8 scFv-Fc humanized VH0 – humanized VL0 |
| 66 | Protein | Artificial | Humanized anti-GDF-8 antibody VH2 |
| 67 | Protein | Artificial | Humanized anti-GDF-8 antibody VL2 |
| 68 | Protein | Artificial | Humanized anti-GDF-8 antibody VH3 |
| 69 | Protein | Artificial | Humanized anti-GDF-8 antibody VL3 |
| 70 | Protein | Artificial | Humanized anti-GDF-8 antibody VH4 |
| 71 | Protein | Artificial | Humanized anti-GDF-8 antibody VL4 |
| 72 | Protein | Artificial | Humanized anti-GDF-8 antibody VH5 |
| 73 | Protein | Artificial | Humanized anti-GDF-8 antibody VL5 |

As further explained in WO 2007/024535, the murine antibody was humanized by CDR grafting. Specifically, the murine VH region was humanized by using the human germline variable heavy (VH) gene DP47 (VH3-23; Genbank Accession No. AB019439) as a human acceptor framework onto which the murine VH CDRs from were grafted. The amino acid sequence of DP47 (SEQ ID NO:33) is shown in FIG. 1A. The murine VL region was humanized using the human germline kappa variable light (VL) gene DPK9 (O12m Vk1; Genbank Accession No. X59315) as a human acceptor framework onto which the murine VL CDRs were grafted. The amino acid sequence of DPK9 (SEQ ID NO:32) is shown in FIG. 1B.

Because the DP47 and DPK9 V region sequences were derived from the germline, not recombined V region genes, the humanization process also required selection of a human J gene segment to encode the amino acid sequence of each partially humanized VH and VL region carboxy terminal to CDR3. As described in WO 2007/024535, humanization was completed using the JH3 heavy chain J segment (SEQ ID NO:35) for the VH region (i.e., DP47/JH3) and using the JK1 light chain J segment (SEQ ID NO:39) for the VL region (i.e., DPK9/JK1). The amino acid sequences encoded by these J segment genes appear directly after the VH CDR3 and VL CDR3 in the sequence alignment shown in FIG. 1A and FIG. 1B, respectively.

As used herein, the humanized anti-GDF-8 antibody VH region constructed using DP47 and JH3 described in WO 2007/024535 is called VH1 (SEQ ID NO:7), whereas the humanized anti-GDF-8 antibody VL region constructed using DPK9 and JK1 is called VL1 (SEQ ID NO:9). Also as used herein, a humanized anti-GDF-8 antibody comprising VH1 and VL1 is called OGD1.1.1. In this nomenclature, the VH region number follows directly after the antibody name "OGD1" and the VL region number follows directly after the VH region number. Thus, for example, the antibody name OGD1.0.1 would refer to an antibody having a VH0 region and a VL1 region, whereas the antibody name OGD1.1.0 would refer to an antibody having a VH1 region and a VL0 region. Alignment between mouse VH and VL regions, humanized VH1 and VL1 regions, and amino acids encoded by the DPK9 and DP47 gene sequences is illustrated in FIG. 1A and FIG. 1B.

Novel versions of humanized anti-GDF-8 antibody are described herein which have the surprising property of being expressed by cells at substantially higher levels compared to OGD1.1.1 while retaining the capacity to specifically bind GDF-8 with high affinity and to neutralize GDF-8 activity.

In certain embodiments of these new antibodies, a different heavy J segment, i.e., JH4 (Genbank Accession No. J00256) (SEQ ID NO:37), was used after CDR3 in the VH region. As a result of this change, Leu (L) replaces Met (M) at position 108 of the VH region using the Kabat numbering scheme compared to VH1. As used herein, this novel humanized VH region in which L appears at Kabat position 108 is called VH0. The amino acid sequence of VH0 (SEQ ID NO:44) is illustrated in the sequence alignment of FIG. 1A.

Because the Kabat numbering scheme uses letters appended to certain of the same numbers to indicate CDRs of variable lengths, there is not necessarily a one-to-one correspondence between a residue's Kabat number and its physical location in the sequence of residues in a polypeptide. For this reason, Kabat position 108 of the VH region is equivalent to amino acid number 111 in SEQ ID NO:44 (i.e., VH0) and the amino acid sequences of the other humanized VH regions disclosed herein.

In other embodiments of the antibodies of the present disclosure, a different light J segment, i.e., JK4 (Genbank Accession No. J00242) (SEQ ID NO:41), was used after CDR3 in the VL region. As a result of this change, Gly (G) replaces Gln (Q) at position 100 of the VL region using the Kabat numbering scheme compared to VL1. As used herein, this novel humanized VL region in which G appears at Kabat position 100 is called VL0. The amino acid sequence of VL0 (SEQ ID NO:46) is illustrated in the sequence alignment FIG. 1B.

As used herein, a humanized anti-GDF-8 antibody comprising a heavy chains comprising VH0 and a light chain comprising VL0 is called OGD1.0.0.

The gene segments, sequences and terminology associated with the VH and VL embodiments described above is summarized in Table 2, below.

TABLE 2

Summary of humanized VH and VL regions

| Humanized Variable Region | Human Acceptor Framework | Human J-Segment |
|---|---|---|
| VH1 (Seq ID No: 7) | DP47 (Seq ID No: 33) | JH3 (Seq ID No: 36) |
| VH0 (Seq ID No: 44) | DP47 (Seq ID No: 33) | JH4 (Seq ID No: 38) |
| VL1 (Seq ID No: 9) | DPK9 (Seq ID No: 32) | JK1 (Seq ID No: 40) |
| VL0 (Seq ID No: 46) | DPK9 (Seq ID No: 32) | JK4 (Seq ID No: 42) |

As described further in the Examples, it has surprisingly been discovered that anti-GDF-8 antibodies comprising VH0 are expressed by cells at much higher levels compared to anti-GDF-8 antibodies comprising VH1. For example, in one non-limiting embodiment described in Example 1, it was surprisingly demonstrated that an intact immunoglobulin comprising VH0 and VL0 (i.e., OGD1.0.0) was transiently expressed at levels more than 12 times greater than a similar antibody comprising VH1 and VL1 (i.e., OGD1.1.1). Stable expression levels were also much higher, as discussed in Example 2. Interestingly, as explored in Example 3, it was found that the enhanced expression was attributable to the presence of VH0, since enhanced expression occurred regardless whether VH0 was paired with VL0 or VL1 and only occurred when VL0 was paired with VH0, but not VH1.

In certain embodiments the antibodies of the present disclosure are intact heterotetrameric Ig molecules comprising full length heavy and light chains in which the variable heavy region is VH0 and the variable light region is VL0 (OGD1.0.0) or VL1 (OGD1.0.1), whereas in other embodiments, the antibodies are GDF-8 specific binding fragments or derivatives of such full length antibodies.

According to some embodiments, the VH regions of the antibodies of the present disclosure comprise the three heavy chain CDRs, i.e., CDRH1, CDRH2, and CDRH3, present in the amino acid sequence of SEQ ID NO:44 or its mouse counterpart, SEQ ID NO:3, and in which the amino acid at Kabat position 108 is leucine. In other embodiments, the VH region comprises the amino acid sequence of SEQ ID NO:44 (i.e., VH0). In other embodiments, the VL regions of the antibodies of the present disclosure comprise the three light chain CDRs, i.e., CDRL1, CDRL2, and CDRL3, present in the amino acid sequence of SEQ ID NO:46 or its mouse counterpart, SEQ ID NO:5, and in which the amino acid at Kabat position 100 is glycine or is glutamine. In other embodiments, the VL region comprises the amino acid sequence of SEQ ID NO:46 (i.e., VL0) or of SEQ ID NO:48 (i.e., VL1).

In the antibodies of the present disclosure, the antibody heavy chain isotype can be any of the human Ig isotypes or subtypes, i.e., IgA1, IgA2, IgD, IgE, IgG1, IgG2, IgG3, IgG4, or IgM. The antibody light chain isotype can be kappa or lambda. In specific non-limiting embodiments, the antibody constant heavy chain is the amino acid sequence of SEQ ID NO:19 or SEQ ID NO:57, both of which are the IgG1 subtype. SEQ ID NO:19 contains two substitution mutations in the hinge region that prevent binding to Fc receptors on immune cells, whereas SEQ ID NO:57 contains an additional hinge region mutation, for a total of three, having similar phenotype. In another specific non-limiting embodiment, the light chain CH region is the amino acid sequence of SEQ ID NO:17, which is the kappa isotype.

In a specific non-limiting embodiment of the present disclosure, an anti-GDF-8 antibody comprises a full length antibody heavy chain according to the amino acid sequence of SEQ ID NO:58 and a full length antibody light chain according to the amino acid sequence of SEQ ID NO:59. The former sequence comprises VH0 and the heavy chain constant regions of the amino acid sequence of SEQ ID NO:57, whereas the latter sequence comprises VL0 and the light chain kappa constant region of the amino acid sequence of SEQ ID NO:17. According to another exemplary non-limiting embodiment, an anti-GDF-8 antibody of the disclosure comprises an intact heterotetrameric antibody consisting of two antibody heavy chains and two antibody light chains according to the amino acid sequences of SEQ ID NO:58 and SEQ ID NO:59 (i.e., OGD1.0.0).

As stated above, in yet other embodiments, antibodies of the present disclosure include antigen binding fragments or derivatives of anti-GDF-8 immunoglobulins comprising VH0. In certain embodiments of the fragments or derivatives, VH0 may be paired with VL0 or VL1. Non-limiting examples fragments or derivatives according to the present disclosure include Fab', F(ab)₂, Fab, Fv, scFv, dsFv, diabodies, triabodies, and single domain antibodies, such as shark antibody or camelized antibody or nanobody, comprising VH0. Other fragments or derivatives are also possible. A specific non-limiting example of an Ig derivative according to the present disclosure includes SEQ ID NO:63, an scFv in which VL0 is tandemly arranged amino-terminal to VH0. Another non-limiting example is SEQ ID NO:65, an scFv in which the V regions are reversed, with VH0 being tandemly arranged amino-terminal to VL0.

Although the antibodies of the present disclosure are exemplified by an immunoglobulin in which the heavy chain CDRs of a murine anti-GDF-8 antibody were grafted onto the human germline VH region DP47, humanized anti-GDF-8 antibodies of the disclosure are not limited to use of that variable region only. Thus, for example, antibodies also include intact immunoglobulins, and fragments or derivatives thereof, in which the murine heavy chain CDRs (i.e., SEQ ID NO:10-12 or 20-22) are grafted onto human VH regions different from DP47, and further modified so that the resulting VH region polypeptide includes Leu (L) at Kabat position 108. The sequence of other human germline VH regions can be found by searching Genbank or various publicly accessible internet databases, including VBASE (http://vbase.mrc-cpe.cam.ac.uk/) or VBASE2 (http://www.vbase2.org/).

As described further in Example 10, the co-crystal structure of OGD1.0.0 and a chimeric anti-GDF-8 antibody comprising the murine VH and VL regions of SEQ ID NO:3 and SEQ ID NO:5, respectively bound to GDF-8 was solved and used to identify the contact residues in the antibody responsible for antigen binding. Using this information, and as explained further in Example 11, the VH and VL regions were further humanized by mutating non-contact residues in the CDRs to match the residues present at the same position in a human germline variable sequence. As shown in FIG. 1A, the further humanized variable heavy regions are called VH2, VH3, VH4 and VH5. And, as shown in FIG. 1B, the further humanized variable light regions are called VL2, VL3, VL4 and VL5.

In certain embodiments of the antibodies of the present disclosure, any of the humanized VH regions may be paired with any of the humanized VL regions to generate intact anti-GDF-8 antibodies, or antigen binding fragments or derivatives thereof. For example, in certain embodiments, VH0 may be paired with any one of the VL regions VL0, VL1, VL2, VL3, VL4, or VL5. In other embodiments, VH1 may be paired with any one of the VL regions VL0, VL1, VL2, VL3, VL4, or VL5. In other embodiments, VH2 may be paired with any one of the VL regions VL0, VL1, VL2, VL3, VL4, or VL5. In other embodiments, VH3 may be paired with any one of the VL regions VL0, VL1, VL2, VL3, VL4, or VL5. In other embodiments, VH4 may be paired with any one of the VL regions VL0, VL1, VL2, VL3, VL4, or VL5. And in certain other embodiments, VH5 may be paired with any one of the VL regions VL0, VL1, VL2, VL3, VL4, or VL5.

As explained above, mutation of non-contact residues within the CDRs and framework regions is expected to minimally impact GDF-8 binding specificity and/or affinity, whereas mutation of contact residues is expected to have greater effect. Although mutations, particularly of contact residues, may reduce binding specificity and/or affinity, in some cases, mutations will be observed to increase specificity and/or affinity for GDF-8. The actual effect on specificity or affinity of any particular mutation can be determined using techniques familiar to those of ordinary skill in the art, e.g., surface plasmon resonance or other techniques.

In view of the foregoing principles, in certain embodiments, one, two, three or more non-contact residues within one or more VH and/or VL CDRs or framework regions of the antibodies of the disclosure can be conservatively or non-conservatively substituted with different amino acid residue and retain substantial specificity and binding affinity for GDF-8. In other embodiments, one, two, three or more contact residues within one or more VH and/or VL CDRs can be conservatively substituted and retain substantial GDF-8 specificity and binding affinity. In yet other embodiments, mutations of non-contact residues or contact residues results in improved specificity and/or affinity for GDF-8.

In other embodiments of the antibodies of the disclosure, the amino acid sequences of the VH and/or VL region may differ by varying percentages from the sequences specifically recited herein and retain substantial, or even improved, specificity and/or affinity for GDF-8. Thus, in certain embodiments, the VH region of an anti-GDF-8 antibody of the disclosure can differ by 80%, 85%, 90%, 91%, 92%, 93%, 94%, 95%, 96%, 97%, 98%, or 99% from the amino acid sequence of VH0, VH1, VH2, VH3, VH4, or VH5. In other embodiments, the VL region of an anti-GDF-8 antibody of the disclosure can differ by 80%, 85%, 90%, 91%, 92%, 93%, 94%, 95%, 96%, 97%, 98%, or 99% from the amino acid sequence of VL0, VH1, VH2, VH3, VH4, or VH5. And in yet other embodiments, the VH and VL regions of anti-GDF-8 antibodies can differ from those specifically recited herein by similar percentages while retaining substantial, or even improved, GDF-8 specificity and/or binding affinity.

Antibodies of the present disclosure can also be derivatized, covalently modified, or conjugated to other molecules to alter their properties or improve their function. For example, but not by way of limitation, derivatized antibodies include antibodies that have been modified, e.g., by glycosylation, fucosylation, acetylation, pegylation, phosphorylation, amidation, formylation, derivatization by known protecting/blocking groups, linkage to a cellular ligand or other protein, etc.

In some embodiments, the C-terminal lysine of the heavy chain of an anti-GDF-8 antibody of the present invention may be cleaved and removed. Thus, for example, in certain embodiments of the present disclosure, an anti-GDF-8 antibody comprises the heavy chain constant regions of SEQ ID NO:19 or SEQ ID NO:57 lacking the C-terminal lysine, or can comprise the antibody heavy chain of SEQ ID NO:58 lacking the C-terminal lysine.

Certain modifications to the structure of anti-GDF-8 antibodies may occur naturally as a result of the type of cell in which they are produced. In a non-limiting example, synthesis of antibodies in mammalian cells, such as CHO cells, may result in glycosylation at one or more amino acids in the antibody chains. In an exemplary non-limiting embodiment of an anti-GDF-8 antibody, amino acid N296 in the heavy chain is glycosylated. Glycosylation at other sites may also be possible. As will be appreciated by those of ordinary skill, production of antibodies in some other types of cells, e.g., bacterial cells, can result in antibody chains that are non-glycosylated. Other types of antibody modification may occur naturally, or non-naturally via chemical or enzymatic modifications undertaken during or after antibody purification.

Alternatively, specific amino acids in the variable or constant regions can be altered to change or improve function. In one non-limiting example, amino acid residues in the Fc region of an antibody may be altered to increase the serum half-life of the antibody by increasing its binding to FcRn. See, e.g., WO 2000/009560, incorporated by reference herein. In other non-limiting examples, antibody amino acids can be changed to reduce binding to one or more Fc receptors, complement, or other immune receptors that mediate Ig biological effector functions. In another non-limiting example, amino acids in the CDRs, framework regions or constant regions may be changed to increase GDF-8 binding affinity or to reduce immunogenicity. In a specific non-limiting example, certain human framework residues of the VH or VL regions of the antibodies of the present disclosure may be changed back to their murine counterparts as in the amino acid sequences of SEQ ID NO:26 and SEQ ID NO:27, respectively.

In other embodiments, antibodies are labeled with a detectable moiety and can be detected, both according to methods familiar to those of ordinary skill in the art. Such labels can be conjugated directly or indirectly to an antibody of the disclosure. The label can itself be directly detectable (e.g., radionuclide or fluorescent label), or be indirectly detectable by its ability to generate detectable molecules (e.g., an enzymatic label that catalyzes a substrate to produce a product that is directly detectable). Examples of detectable labels include enzymes (e.g., horseradish peroxidase, β-galactosidase, luciferase, alkaline phosphatase, etc.), prosthetic groups (e.g., biotin, etc.), fluorescent dyes or moieties (e.g., FITC, rhodamine, lanthanide phosphors), luminescent moieties, bioluminescent moieties, radionuclides (e.g., $^3$H, $^{14}$C, $^{15}$N, $^{35}$S, $^{90}$Y, $^{99}$Tc, $^{111}$In, $^{125}$I, $^{131}$I etc.), positron emitting atoms or ions, magnetic atoms or ions, paramagnetic metal atoms or ions, or peptide epitopes that can be specifically bound by other antibodies. In some embodiments, labels may be attached using spacers of various lengths to reduce or prevent potential steric hindrance with an antigen binding site.

Antibodies of the present disclosure can be expressed in culture or in animals from any cell type capable of sustaining the expression of mammalian proteins. Non-limiting examples include human cells, mouse, rat or other rodent cells, other mammalian cells, CHO cells, yeast cells or cells of other fungi, plant cells, or bacterial cells. Techniques useful for cloning DNA encoding Ig molecules, or fragments or derivatives thereof, into expression vectors, and then transiently or stably transfecting cells with such vectors, are well known in the art. Culture conditions can be altered to maximize antibody expression levels. Antibodies can also be expressed in animals using techniques familiar to those of ordinary skill, and then purified from milk or other bodily fluids. Antibodies may also be fully or partially synthetic.

Antibodies of the present disclosure bind GDF-8 with high affinity, e.g., with an equilibrium dissociation constant ($K_D$) of at least about $1\times10^{-6}$ M, $1\times10^{-7}$ M, $1\times10^{-8}$, $1\times10^{-9}$, $1\times10^{-10}$, $1\times10^{-11}$ M or higher. The $K_D$ of an anti-GDF-8 antibody for GDF-8 can be determined according to various methods familiar to those of ordinary skill in the art. Non-limiting examples of such techniques include surface plasmon resonance (SPR) and ELISA. As will be familiar to those of ordinary skill, due to avidity effects, the apparent binding affinity of an anti-GDF-8 antibody having two or more antigen binding sites may be greater than an antibody fragment having a monovalent antigen binding site.

Although antibodies of the present disclosure are specific for GDF-8, such antibodies may depending on the epitope or epitopes recognized also be able to bind with high affinity to the closely related growth and differentiation factor known as GDF-11. Thus, an antibody specific for GDF-8 does not necessarily exclude antibodies capable of binding to GDF-11 molecules.

As used herein, a neutralizing anti-GDF-8 antibody is one that reduces a biological activity of GDF-8 compared to a non-specific control antibody or other suitable control. Without wishing to be bound by any particular theory of operation, one way at least that an anti-GDF-8 antibody may neutralize a biological function mediated by GDF-8 is to prevent mature GDF-8 binding to its high affinity receptor, e.g., ActRIIB, or one or more of its low affinity receptors. However, other mechanisms by which an anti-GDF-8 neutralizing antibody may interfere with GDF-8 biological activities are possible.

Numerous biological activities mediated by GDF-8 that may be reduced by a neutralizing antibody of the disclosure are known in the art. Non-limiting examples include GDF-8 binding to ActRIIB, which can be measured, e.g., using an ELISA based assay. Another example includes activation by GDF-8 of its cellular signaling pathway, which can be detected, e.g., using a transfected reporter gene including so-called GAGA elements. See, e.g., Lee, et al., Regulation of muscle growth by multiple ligands signaling through activin type II receptors, PNAS (2005) 102:18117-18122, and Thies, et al., GDF-8 Propeptide Binds to GDF-8 and Antagonizes Biological Activity by Inhibiting GDF-8 Receptor Binding, Growth Factors (2001) 18:251-59, which are incorporated by reference. Yet another example includes phosphorylation of SMAD proteins responsible for conveying GDF-8 mediated signaling from GDF-8 receptors at the cell surface into the nucleus. See, e.g., Philip, et al., Regulation of GDF-8 signaling by the p38 MAPK, Cellular Signalling (2005) 17:365-375, which is incorporated by reference. Phosphorylation of SMAD proteins can be detected with, e.g., quantitative Western blotting using anti-phosho-SMAD antibodies. Modulation of downstream gene expression of genes ordinarily activated or repressed by GDF-8 can also be detected. Yet another example of a GDF-8 mediated activity that can be reduced using neutralizing antibodies of the present invention is negative regulation of muscle mass or strength. Other activities are also possible.

Neutralizing antibodies of the present disclosure can reduce a biological activity mediated by GDF-8 to varying degrees depending on variables familiar to those of ordinary skill, such as antibody and antigen concentration and binding affinity, as well as others. Exemplary non-limiting percentage reductions in GDF-8 mediated biological activity caused by antibody binding to GDF-8 include reductions of at least about 10%, 20%, 30%, 40%, 50%, 60%, 70%, 80%, 90%, 95%, 99%, or more compared to suitable controls.

Inhibition by an anti-GDF-8 antibody of a GDF-8 mediated biological activity can conveniently be expressed as the concentration of such antibody that is capable of inhibiting 50% of the biological activity under whatever assay conditions are selected. This concentration is also called $IC_{50}$. In certain embodiments, anti-GDF-8 antibodies of the present disclosure have $IC_{50}$ values equal to or less than about 500 nM, 250 nM, 100 nM, 75 nM, 50 nM, 40 nM, 30 nM, 20 nM, 10 nM, 5 nM, 1 nM, 0.5 nM, 0.1 nM, or less.

Secretory Leader Sequences

According to certain embodiments, the genes encoding antibody heavy and light chains can be provided with sequence encoding an amino-terminal secretory leader peptide that directs newly synthesized proteins to the secretory compartment. Post-translational processing then removes the leader peptides before the mature antibody is secreted from the cell. In specific non-limiting embodiments of antibodies of the present disclosure, VH0, VH1, VL0 and VL1 regions are provided with a secretory leader peptide 19 amino acids long. These V regions including a leader sequence are assigned the following sequence identification numbers: VH0 (SEQ ID NO:50); VL0 (SEQ ID NO:52); VH1 (SEQ ID NO:54); and VL1 (SEQ ID NO:56). Other secretory leader sequences may also be used. Non-limiting examples include the first 19 amino acids of the murine VH region and its leader sequence (SEQ ID NO:29) and the first 20 amino acids of murine VL region and its leader sequence (SEQ ID NO:31).

Anti-GDF-8 Antibody Expression

As explained in more detail in the Examples, OGD1.0.0 was expressed at substantially higher levels compared to OGD1.1.1 in mammalian cells. For example, when OGD1.0.0 and OGD1.1.1 were expressed in transiently transfected COS cells, OGD1.0.0 was expressed at about 12 fold higher levels compared to OGD1.1.1. Similarly, when these antibodies were expressed in stably transfected CHO cells, OGD1.0.0 was expressed at about 6 fold higher levels compared to OGD1.1.1. Also as explained in the Examples, the difference in expression levels appears to be mainly attributable to presence in the antibody of VH0 instead of VH1.

Thus, antibodies of the present disclosure comprising VH0 exhibit greater expression compared to similar antibodies comprising VH1 when expressed under similar conditions. For example, in certain embodiments, the expression level of antibodies comprising VH0 is greater than that of a similar antibody containing VH1 expressed under similar conditions by an amount that is at least about 1.5 fold, 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold or more. The extent of the difference in expression levels between the antibodies may depend, for example, on the type of host cell used to express the antibodies, for example, COS cells or CHO cells, or whether the host cells are transiently or stably transfected. The comparative expression levels of antibodies containing VH0 or VH1 variable heavy regions may vary as other growth conditions are changed and can be determined using methods familiar to those of ordinary skill in the art.

In other embodiments, the level of VH0 antibody expression is greater than that of a similar antibody containing VH1 expressed under similar conditions by an amount that is at least about 10%, 15%, 20%, 25%, 30%, 35%, 40%, 45%, 50%, 75%, 100%, 150%, 200%, 250%, 300%, 400%, 500%, 600%, 700%, 800%, 900%, 1000%, 1100%, 1200%, 1300%, 1400%, 1500%, 1600%, 1700%, 1800%, 1900%, 2000%, 3000%, 4000%, 5000%, or more. Other differences in expression levels, such as between the percentages recited herein, are also possible.

Antibody expression levels can be measured using techniques familiar to those of ordinary skill in the art. In one non-limiting example, antibody expression levels can be measured using a quantitative ELISA assay. Other quantitative assays may also be used according to the knowledge of those ordinarily skilled.

Nucleic Acid Molecules Encoding Anti-GDF-8 Antibodies

The present disclosure also provides nucleic acid molecules or polynucleotides encoding anti-GDF-8 antibodies. Nucleic acids may comprise DNA or RNA in which U replaces T in the DNA nucleobase sequence. Nucleic acids may also contain modifications, such as non-standard nucleobases (e.g., 5 methylcytosine) or a modified backbone (e.g., phosphorothioate). Other modifications are possible. Nucleic acids may be single or double stranded. Nucleic acids may be obtained from a natural source, such as a cell or whole organism. Non-limiting examples of naturally sourced nucleic acids include genomic DNA, amplified plasmid DNA or mRNA. Alternatively, nucleic acids may be synthesized. Non-limiting examples of synthetic nucleic acids include cDNA, a product of PCR or a nucleic acid synthesized on a nucleic acid synthesis machine.

In certain embodiments, nucleic acids of the present disclosure encode the amino acid sequence of an antibody heavy chain, or fragment or derivative thereof, comprising VH0. In other embodiments, nucleic acids encode the amino acid sequence of an antibody light chain, or derivative or fragment thereof, comprising VL0. In yet other embodiments, nucleic acid sequences encoding VH0 and a VL region, such as VL0 or VL1 are present in different or the same isolated polynucleotides.

Although the present disclosure provides specific nucleic acid sequences encoding anti-GDF-8 antibodies, or fragments or derivatives thereof, one of ordinary skill in the art will appreciate that due to the degeneracy of the genetic code such sequences are merely exemplary and are not to be construed as limiting. Thus, exemplary nucleic acid sequences encoding the VH and VL regions of a murine anti-GDF-8 antibody are SEQ ID NO:2 and SEQ ID NO:4, respectively. Exemplary nucleic acid sequences encoding VH1 are SEQ ID NO:6 and SEQ ID NO:47. Exemplary nucleic acid sequences encoding VL1 are SEQ ID NO:8 and SEQ ID NO:48. An exemplary nucleic acid sequence encoding VH0 is SEQ ID NO:43. An exemplary nucleic acid sequence encoding VL0 is SEQ ID NO:45. An exemplary nucleic acid sequence encoding the amino acid sequence of SEQ ID NO:19, comprising the CH regions of an IgG1 containing two hinge region mutations, is SEQ ID NO:18. An exemplary nucleic acid sequence encoding the amino acid sequence of SEQ ID NO:17, comprising a human kappa CL region, is SEQ ID NO:16. Exemplary nucleic acid sequences encoding the VH and VL regions of a murine anti-GDF-8 antibody preceded by leader sequences are SEQ ID NO:28 and SEQ ID NO:30, respectively. Exemplary nucleic acid sequences encoding the amino acid sequences of the VH0, VL0, VH1 and VL1 regions preceded by leader sequences are SEQ ID NO:49; SEQ ID NO:51; SEQ ID NO:53; and SEQ ID NO:55, respectively.

According to certain embodiments, a nucleic acid molecule comprises a nucleic acid sequence encoding the amino acids of any of the following SEQ ID NOs: 7, 9, 10, 11, 12, 13, 14, 15, 17, 19, 20, 21, 22, 23, 24, 25, 26, 27, 36, 38, 40, 42, 44, 46, 50, 52, 54, 56, 57, 58, 59, 63 or 65. In other embodiments, nucleic acid molecules comprise a nucleic acid sequence encoding amino acid sequences that are at least 85%, 90%, 91%, 92%, 93%, 94%, 95%, 96%, 97%, 98% or 99% identical to SEQ ID NOs: 7, 9, 10, 11, 12, 13, 14, 15, 17, 19, 20, 21, 22, 23, 24, 25, 26, 27, 36, 38, 40, 42, 44, 46, 50, 52, 54, 56, 57, 58, 59, 63 or 65. In yet other embodiments, nucleic acid molecules comprise a nucleic acid sequence encoding amino acid sequences that are at least 80%, 85%, 90%, 91%, 92%, 93%, 94%, 95%, 96%, 97%, 98% or 99% identical to VH0 (SEQ ID NO:44) and in which Kabat position 108 is Leucine.

According to certain embodiments, a nucleic acid molecule comprises the nucleic acid sequence of any of the following SEQ ID NOs: 6, 8, 16, 18, 35, 37, 39, 41, 43, 45, 47, 48, 49, 51, 53, 55, 62 or 64. In other embodiments, nucleic acid molecules comprise a nucleic acid sequence that is at least 80%, 85%, 90%, 91%, 92%, 93%, 94%, 95%, 96%, 97%, 98% or 99% identical to the nucleic acid sequences of SEQ ID NOs: 6, 8, 16, 18, 35, 37, 39, 41, 43, 45, 47, 48, 49, 51, 53, 55, 62 or 64. In yet other embodiments, nucleic acid molecules comprise a nucleic acid sequence that hybridize under highly stringent conditions to the nucleic acid sequences of SEQ ID NOs: 6, 8, 16, 18, 35, 37, 39, 41, 43, 45, 47, 48, 49, 51, 53, 55, 62 or 64.

A non-limiting example of highly stringent hybridization conditions is incubation of the nucleic acids being hybridized in 1×SSC at 65° C., or 1×SSC and 50% formamide at 42° C., followed by washing in 0.3×SSC at 65° C. Additional examples of stringency conditions are provided in Sambrook et al., Molecular Cloning: A Laboratory Manual, Chs. 9 & 11, Cold Spring Harbor Laboratory Press, Cold Spring Harbor, N.Y. (1989), herein incorporated by reference.

As will be appreciated by those of ordinary skill in the art, certain of the nucleic acids of the present disclosure may be ligated together in-frame to create composite nucleic acid sequences. For example, a nucleic acid encoding VH0 can be ligated in-frame to a nucleic acid encoding CH regions to create a composite nucleic acid encoding a complete heavy chain. In a non-limiting example, the nucleic acid sequence of SEQ ID NO:43, encoding VH0, can be ligated in frame with a nucleic acid sequence encoding the amino acid sequence of SEQ ID NO:57, the constant portion of a human IgG1 heavy chain containing three mutations affecting effector function. Similar ligations to create a light chain are possible, as are other ligations to create other composites of the nucleic acids described herein.

Vectors

Nucleic acids of the present disclosure may be incorporated into vectors using techniques well known to those of ordinary skill in the art. Vectors, in certain embodiments, include plasmids generally, bacterial plasmids, eukaryotic episomes, yeast artificial chromosomes and viral genomes. Exemplary non-limiting viruses include retroviruses, adenoviruses, adeno-associated viruses (AAV), and plant viruses such as cauliflower mosaic virus, and tobacco mosaic virus. Other types of vectors are possible. In some embodiments, vectors are capable of autonomous replication in suitable hosts. In other embodiments, vectors are maintained in hosts extrachomosomally or can become integrated into the host's genome allowing the vector to replicate with the host's genome. Vectors comprising a gene and control sequences sufficient to maintain transcription and translation of the gene are called expression vectors. Vectors according to the present disclosure may be selected or designed, according to the knowledge of those ordinarily skilled in the art, to function in any cell type capable of supporting expression of Ig genes, including bacterial cells, other prokaryotic cells, yeast cells, other fungal cells, plant cells, animal cells, insect cells, mammalian cells, CHO cells, and human cells, or others.

Vectors may optionally contain one or more control sequences. Certain control sequences permit replication, such as origins of replication. Other control sequences control or modulate transcription, such as promoters, enhancers, and transcription termination sites. Non-limiting examples of promoter or enhancers are those derived from retroviral LTRs, cytomegalovirus (CMV), Simian Virus 40 (SV40), adenovirus (e.g., the adenovirus major late promoter (AdMLP)), or polyoma virus. Additional examples include tissue specific promoters and enhancers, constitutively active promoters and enhancers, inducible promoters and enhancers, Ig gene promoters and enhancers and actin promoters and enhancers. Other promoters and enhancers are also possible.

Certain control sequences control or modulate post-transcriptional RNA processing, such as splicing and polyadenylation signals, or signals that increase or decrease mRNA stability. Yet other control sequences control or modulate protein translation, such as translation initiation sequences (e.g., Kozak consensus sequence), post-translational processing, such as signal peptide sequences directing secretion of a gene product out of a host cell, or protein stability. Signal peptide sequences can be derived from immunoglobulins or from secreted proteins that are not part of the Ig superfamily. Other control sequences are also possible.

Vectors can also include selectable marker genes, permitting the selection of host cells that have taken up the vectors. Non-limiting examples include selectable marker genes that confer a drug resistant phenotype, such as the dihydrofolate reductase gene (DHFR) (for use in dhfr⁻ host cells permitting selection using methotrexate), the neo gene (permitting selection with G418 or similar drugs), the hph gene (permitting selection with hygromycin B), and the glutamate synthetase gene (permitting selection with methionine sulfoximine).

In some embodiments, vectors can comprise a nucleic acid sequence encoding a single Ig heavy or light chain, or antigen binding fragments thereof, but not both chains in the same vector. Typically, expression of intact antibodies from such vectors involves introducing the separate vectors comprising the heavy chain and the light chain into the same cell. In other embodiments, vectors can comprise nucleic acid sequences encoding both heavy and light Ig chains, or antigen binding fragments thereof, in the same vector.

Nucleic acid molecules of the present disclosure, or vectors comprising such nucleic acids, may be introduced into one or more types of host cells capable of supporting antibody expression. Methods for introducing nucleic acids or vectors into suitable host cells are well known to those of ordinary skill in the art. Non-limiting examples include transient and stable transfection, transformation, transduction and viral infection of target host cells. Other examples include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Exemplary non-limiting methods are discussed in, e.g., U.S. Pat. Nos. 4,399,216, 4,912,040, 4,740,461, and 4,959,455, which are incorporated by reference. Methods for transforming plant cells are also well known in the art including, e.g., *agrobacterium*-mediated transformation, biolistic transformation, direct injection, electroporation and viral transformation. Methods of transforming bacterial and yeast cells are also well known in the art.

Host Cells

In certain embodiments, nucleic acids encoding antibodies of the present disclosure, or fragments or derivatives thereof, are introduced into suitable host cells for purposes of expression. Cells capable of expressing antibodies include bacterial, fungal, plant, animal, and mammalian cells. The types of cells may also be used according to the knowledge of the skilled artisan.

Mammalian cell lines suitable as hosts for antibody expression are known in the art. Exemplary non-limiting examples include certain immortalized cell lines available from the American Type Culture Collection (ATCC) or other sources, including Chinese hamster ovary (CHO) cells, NS0 cells, SP2 cells, HEK-293T cells, NIH-3T3 cells, HeLa cells, baby hamster kidney (BHK) cells, African green monkey kidney cells (e.g., COS, CV-1 or Vero cells), human hepatocellular carcinoma cells (e.g., HepG2), A549 cells, A431 cells, HeLa cells, L cells, BHK21 cells, HL-60 cells, U937 cells, HaK cells, Jurkat cells, and others. Other animal, insect, or mammalian cells suitable as hosts for antibody expression are possible.

In other embodiments, cell lines from insects, plants, bacteria or fungi may be used. Exemplary non-limiting insect cells include Sf9 or Sf21 cells, which are often used in conjunction with the baculovirus vector expression system. Exemplary non-limiting plant cells include those from *nicotiana, arabidopsis*, duckweed, corn, wheat, and potato species. Exemplary non-limiting bacteria include *Escherichia coli, Bacillus subtilis, Salmonella typhimurium*, and *Streptomyces* strains. Exemplary non-limiting fungi include *Schizosaccharomyces pombe, Saccharomyces cerevisiae, Pichia pastoris, Kluyveromyces* yeast strains, and *Candida* yeast strains. Other insect, plant, bacterial and fungal cells are possible.

Methods for growing and maintaining different types of host cells under conditions conducive to antibody expression are well known in the art. After antibody expression has occurred, the antibodies so expressed can then be purified from the host cells according to the knowledge of the skilled artisan. For example, secreted antibodies can be purified from the media in which the host cells are grown. Alternatively, in some embodiments, particularly where the host cells have cell walls, the host cells can be broken open mechanically, chemically or enzymatically to release expressed antibody sequestered within the cells. Exemplary non-limiting methods of antibody purification include ion exchange chromotography, salt precipitation, and gel filtration. In other embodiments, affinity chromotography may be used. For example, mouse antibodies recognizing human constant region sequences can be immobilized to purification columns. Alternatively, antibodies can be expressed fused to epitope tags, or larger affinity tags, such as maltose binding protein, glutathione S-transferase, and thioredoxin, for purification with specific antibodies or other molecules that bind tightly to the affinity tag. Thereafter, the epitopes or affinity tags can be cleaved using techniques familiar to those of ordinary skill and the antibodies purified using other techniques, such as those disclosed herein. Other techniques for purifying antibodies from media and host cells are also possible. Antibodies can also be subjected to additional processing steps to further purify the antibodies in accordance with good manufacturing practice or other regulatory requirements, as the case may be. Suitable purifications and steps for carrying them out are within the knowledge of the skilled artisan.

Transgenic Animals and Plants

Antibodies of the present disclosure may also be produced in genetically modified non-human animals or plants. Expression of antibodies in such organisms may be constitutive or inducible. Antibodies expressed in such organisms can then be isolated using techniques known to those of ordinary skill in the art. Methods for expressing antibodies and antigen-binding fragments thereof in transgenic non-human organisms are well known in the art. In a non-limiting example, antibodies of the present disclosure can be produced in, and recovered from, the milk of goats, cows, or other non-human mammals. See, e.g., U.S. Pat. Nos. 5,827,690, 5,756,687, 5,750,172, and 5,741,957, incorporated by reference herein. Other non-limiting examples of transgenic mammals in which antibodies may be are mice, rats, sheep, pigs, or horses. An additional non-limiting example of a bodily fluid from which antibodies may be isolated is blood. Other bodily fluids are also possible. Antibodies of the present disclosure may also be produced in, and recovered from plants. See, e.g., U.S. Pat. Nos. 6,417,429, 6,046,037, and 5,959,177, incorporated by reference herein.

Pharmaceutical Compositions

For use in the therapeutic and prophylactic methods of the present disclosure the antibodies disclosed herein can be formulated as compositions. Optionally, the compositions can comprise one or more additional agents, including antibodies binding different GDF-8 epitopes than those disclosed herein, therapeutically or prophylactically effective against GDF-8-mediated disorders. The compositions will usually be supplied as part of a sterile, pharmaceutical composition that will normally include a pharmaceutically acceptable carrier. This composition can be in any suitable form depending upon the desired method of administering it to a patient.

Antibodies of the present disclosure can be administered to a subject by a variety of routes, typically parenterally, for example, via subcutaneous, intravenous, intraperitoneal or intramuscular injection. Administration can be effected as one or more bolus injections, or as one or more infusions. Other routes of administration are also possible in accordance with the knowledge of those ordinarily skilled in the art. The most suitable route for administration in any given case may depend on the particular composition to be administered and characteristics of the subject, such as disorder to be treated, age or sex.

Pharmaceutical compositions can be conveniently presented in unit dose forms containing a predetermined amount of antibody per dose. Such a unit can contain for example but without limitation 5 mg to 5 g, 10 mg to 1 g, or 20 to 50 mg. Pharmaceutically acceptable carriers for use in the disclosure can take a wide variety of forms depending, e.g., on the route of administration.

Pharmaceutical compositions of the disclosure can be prepared for storage as lyophilized formulations or aqueous solutions by mixing the antibody having the desired degree of purity with optional pharmaceutically acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, *Remington's Pharmaceutical Sciences*, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-4% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize antibodies, and any other therapeutic agents that may be included, against agitation-induced aggregation, which also permits the composition to be exposed to shear surface stresses without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml.

Additional miscellaneous excipients can include chelating agents (e.g., EDTA), antioxidants (e.g., ascorbic acid, methionine, vitamin E), and co-solvents.

In an exemplary non-limiting embodiment, the antibodies of the disclosure are formulated in a solution comprising 20 mM L-histidine, 85 mg/ml sucrose, 0.2 mg/ml PS-80, 0.05 mg/ml EDTA, at pH 5.8. In other embodiments, the concentration of antibody in this formulation is 100 mg/ml. And, in yet other embodiments, the antibody in this formulation is lyophilized.

Pharmaceutical Kits

In certain embodiments, the invention provides for pharmaceutical kits for use by clinicians or others. The pharmaceutical kit is a package comprising an anti-GDF-8 antibody of the disclosure (e.g., either in lyophilized form or as an aqueous solution) and one or more of the following: at least a second therapeutic agent as described elsewhere in this disclosure; a device for administering the antibody, e.g., a needle and/or syringe; and pharmaceutical grade water or buffer to resuspend or dilute the antibody if the antibody is in lyophilized or concentrated form. Kits may also include instructions for preparing the antibody composition and/or administering the composition to a patient.

Each unit dose of the anti-GDF-8 antibody composition can be packaged separately, and a kit can contain one or more unit doses (e.g., two unit doses, three unit doses, four unit doses, five unit doses, seven unit doses, eight unit doses, ten unit doses, or more). In one embodiment, the one or more unit doses are each housed in a syringe, and in another embodiment, the one or more unit doses are each contained in a bag or similar receptacle suitable for connecting to an I.V. line.

Methods of Treatment and Prevention

The present disclosure provides methods for treating and preventing conditions and disorders in which reducing GDF-8 activity directly or indirectly results in a therapeutic benefit. Such methods comprise administering to a subject an effective amount of a composition comprising an anti-GDF-8 antibody. In certain of these embodiments, the antibody is OGD1.0.0, or GDF-8 binding fragments, parts, portions or derivatives thereof.

The subject to whom anti-GDF-8 antibody compositions can be administered may be a mammal, such as a non-primate (e.g., cow, pig, horse, cat, dog, rat, etc.) or a primate (e.g., monkey, chimpanzee, ape or human). The subject can be a human, such as an adult patient or a pediatric patient.

Conditions and disorders that can be treated with the antibody compositions of the present disclosure are those mediated, at least in part, by GDF-8, or where a scientific rationale exists to suggest that reducing GDF-8 activity in a subject would confer a therapeutic benefit.

Although therapeutic benefit depends, in part, on the particular condition or disorder, therapeutic benefit exists when reducing GDF-8 activity in a subject results in any amelioration of the symptoms, signs or severity of the condition or disorder, or halting or slowing the progressive worsening of such symptoms, signs or severity. Therapeutic benefit further exists where reducing GDF-8 activity increases the life expectancy, comfort or quality of life of a subject. Therapeutic benefit also exists where reducing GDF-8 activity improves or halts or slows the deterioration of one or more bodily or physiologic functions of a subject, or performance of a subject on a test reflecting such functions.

Therapeutic benefit can be inferred by observing a subject perform certain tasks, asking the subject questions about he or she feels, or performing one or more tests on the subject at bedside, or in the laboratory on samples obtained from the subject. Therapeutic benefit may also be evidenced by markers of GDF-8 inhibition. By way of example, not limitation, muscle from a subject under treatment may be biopsied and tested for the presence or absence of markers associated with down-regulation of the signal transduction pathway stimulated by GDF-8, e.g., reduction in the level of phosphorylated SMAD2 or SMAD3 protein. Other tests suitable for detecting therapeutic benefit in a subject under treatment with compositions comprising the antibodies of the present disclosure are within the knowledge of those ordinarily skilled in the art. A complete cure or reversal of the condition or disorder being treated or prevented, while desirable, is not required for therapeutic benefit to exist.

In certain embodiments, compositions comprising antibodies of the present disclosure can be used to treat or prevent conditions or disorders characterized by a loss of skeletal muscle mass and/or strength, or where increasing such muscle mass and/or strength confers therapeutic benefit. In certain of these embodiments the antibody is OGD1.0.0, or GDF-8 binding fragments or derivatives thereof.

Conditions or disorders relating to diminished muscle mass and/or strength treatable or preventable by administration of the antibodies disclosed herein include, but are not limited to, age-related loss of muscle mass or strength, frailty, sarcopenia, and loss of muscle mass or strength caused by muscle atrophy, immobilization or disuse, such as after injury, denervation, or sustained exposure to a zero gravity environment. In other embodiments, conditions or disorders that can be treated or prevented include bone fractures, particularly in the elderly or others susceptible to bone fracture, such as hip fracture, or that of other bones, or to stabilize joint replacements. In some other embodiments, conditions or disorders that can be treated or prevented are muscle wasting syndromes, including those attributable to a primary disease process. Non-limiting examples of muscle wasting syndromes include cachexia, such as that caused by cancer, anorexia or other types of malnutrition, and muscle wasting caused by AIDS, sepsis, burns, chronic kidney failure, congestive heart failure (CHF), and chronic obstructive pulmonary disease (COPD).

By way of example and not limitation, therapeutic benefit in subjects administered a composition comprising antibodies of the present disclosure can be demonstrated through an increase in muscle mass or strength, generally or of specific muscles. Non-limiting examples of muscles the mass and/or strength of which can be increased by treatment with anti-GDF-8 antibodies includes skeletal muscles and cardiac muscle. Other examples include the muscles that control breathing, including the diaphragm and intercostal muscles, as well as accessory muscles of inspiration, including sternocleidomastoid scalene muscles and others. Yet other examples of skeletal muscles include gastrocnemius, tibialis posterior, soleus, tibialis anterior, longus, brevis, gluteus maximus muscle, biceps femoris, semitendinosus, semimembranosus, iliopsoas, quadriceps femoris, adductor muscles of the hip, levator scapulae, trapezius, rectus abdominis, transversus abdominis, abdominal external oblique muscle, abdominal internal oblique muscle, erector spinae, pectoralis major, biceps brachii, triceps brachii, brachialis, pronator teres, brachioradialis, rhomboids, deltoid, and latissimus dorsi. Other skeletal muscles the mass and/or strength of which can be increased by treatment with anti-GDF-8 antibodies of the present disclosure are also possible.

Increases in muscle mass or strength can be assessed directly, such as by observing a subject's ability to resist a force, or lift a weight, or indirectly, such as by scanning a subject's body using MRI, CT or dual-energy X-ray absorptiometry (DEXA). Other techniques are also possible.

Alternatively, therapeutic benefit can be inferred from a reduction in severity of what would otherwise be progressively worsening symptoms. Benefit can also be demonstrated using physiologic tests of muscle function, such as electromyography, histopathological tests of biopsied muscle structure, and biochemical tests, such as presence of serum creatine kinase, an enzyme released by damaged muscle. Other tests of muscle structure and function useful for detecting therapeutic benefit are also possible.

In other embodiments relating to muscle mass and/or strength, the present disclosure provides methods of treating and preventing muscular dystrophy ("MD") by administering to patients in need of such treatment or prevention a composition comprising anti-GDF-8 antibodies. In some embodiments of the methods, the antibody is OGD1.0.0, or anti-GDF-8 binding fragments or derivatives thereof. According to certain embodiments, the subjects are human pediatric patients suffering with muscular dystrophy, and in other embodiments, the subjects are human adult patients with muscular dystrophy.

As is known in the art, there exist different types of muscular dystrophy which differ in the nature of the genetic lesion or lesions responsible for the disease, and the phenotype that results from the underlying genetic defects. Non-limiting examples of types of muscular dystrophy that may be treated or prevented by administration of compositions comprising the antibodies of the present disclosure include Duchenne Muscular Dystrophy (DMD) (also known as Pseudohypertrophic MD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine MD), Myotonic Dystrophy (MMD) (also known as DM or Steinert Disease), Oculopharyngeal Muscular Dystrophy (OPMD), Distal Muscular Dystrophy (DD) (also known as Miyoshi MD), and Congenital Muscular Dystrophy (CMD).

In addition to those techniques for assessing improvements in muscle mass and/or strength described above, therapeutic benefit of administering compositions comprising antibodies of the present disclosure to subjects with MD can be quantified using the 6 minute walk test ("6MWT"). See, e.g., McDonald, et al., The 6-minute walk test as a new outcome measure in Duchenne muscular dystrophy, Muscle Nerve (2010) 41:500-510, which is incorporated by reference herein.

In the 6MWT, subjects are tested to determine how far they are able to walk within 6 minutes along a preset course.

Typically, a subject would be tested prior to beginning treatment to establish a baseline and then at intervals thereafter as treatment progresses. Therapeutic benefit is seen when the MD subject's performance in the 6MWT stays constant or actually improves with treatment, or alternatively, when the subject's performance does not decline as quickly as the average untreated subject. Exemplary non-limiting improvements in performance on the 6MWT include percentage improvements of about 4%, 5%, 6%, 7%, 8%, 9%, 10%, 11%, 12%, 13%, 14%, 15%, 20%, 25%, 30%, 35%, 40%, 45%, 50%, 60%, 70%, 80%, 90%, 100% or greater compared to non-treated, or placebo treated controls. The 6MWT may also be used to detect therapeutic benefit in subjects being treated for conditions or disorders that affect ambulation other than MD.

In other embodiments, the present disclosure provides methods of treating and preventing motor-neuron diseases by administering to patients in need of such treatment or prevention a composition comprising anti-GDF-8 antibodies. In some embodiments of the methods, the antibody is OGD1.0.0, or anti-GDF-8 binding fragments or derivatives thereof. Non-limiting examples of types of motor-neuron diseases that may be treated or prevented by administration of compositions comprising the antibodies of the present disclosure include amyotrophic lateral sclerosis (ALS) (also known as Lou Gehrig's Disease), Spinal Muscular Atrophy Type 1 (SMA1) (also known as Werdnig-Hoffmann Disease), Spinal Muscular Atrophy Type 2 (SMA2), Spinal Muscular Atrophy Type 3 (SMA3) (also known as Kugelberg-Welander Disease), and Spinal Bulbar Muscular Atrophy (SBMA) (also known as Kennedy Disease).

In prior work, it was demonstrated that a murine anti-GDF-8 antibody was effective to increase muscle mass and strength in SOD1 mice and rats, which are small animal models of human ALS. See WO 2007/024535 and Holzbauer, et al., Myostatin inhibition slows muscle atrophy in rodent models of amyotrophic lateral sclerosis, Neurobiology of Disease (2006) 23:697-707, which are incorporated by reference herein. As reported, treatment with the murine antibody increased muscle mass in diaphragm and skeletal muscles of SOD1 mice and rats compared to PBS treated controls. Similarly, antibody treatment reduced muscle atrophy of gastrocnemius muscle and diaphragm in SOD1 mice compared to controls receiving PBS. The trophic effects of antibody treatment were principally evident during the early stages of the disease process as opposed to end stage, although inhibition of diaphragm atrophy was evident during both times. Antibody treatment was also observed to increase limb muscle strength, as well as overall body weight in SOD1 mice and rats, although the antibody did not extend survival compared to control animals treated with vehicle alone. Because the humanized anti-GDF-8 antibodies of the present disclosure, such as OGD1.0.0, share the same antigen binding determinants as the murine antibody discussed above, it is expected that they will also be effective to treat or prevent ALS in humans.

Other inborn or acquired diseases and disorders of the muscles, central nervous system and peripheral nervous system affecting muscle mass, function and/or strength may also be treated or prevented by administering to subjects in need therefor compositions comprising the antibodies of the present disclosure.

The present disclosure also provides methods of treating and preventing metabolic disorders by administering to patients in need of treatment for metabolic disorders a composition comprising anti-GDF-8 antibodies. In certain of these embodiments the antibody is OGD1.0.0, or GDF-8 binding fragments or derivatives thereof.

Non-limiting examples of metabolic disorders that can be treated or prevented by administering the antibodies of the present disclosure include type 2 diabetes mellitus, metabolic syndromes, such as syndrome X, insulin resistance, and impaired glucose tolerance.

In other embodiments, the present disclosure provides methods of treating and preventing adipose tissue disorders by administering to patients in need of treatment for such disorders a composition comprising anti-GDF-8 antibodies. In certain of these embodiments the antibody is OGD1.0.0, or GDF-8 binding fragments or derivatives thereof.

Non-limiting examples of adipose tissue disorders that can be treated or prevented by administering the antibodies of the present disclosure include obesity and higher than normal body mass index (BMI) for a particular subject's sex, age and stature.

In other embodiments, the present disclosure provides methods of treating and preventing bone loss disorders by administering to patients in need of treatment for such disorders a composition comprising anti-GDF-8 antibodies. In certain of these embodiments the antibody is OGD1.0.0, or GDF-8 binding fragments or derivatives thereof.

Non-limiting examples of bone loss disorders that can be treated or prevented by administering the antibodies of the present disclosure include osteoporosis, hormone-related osteoporosis, osteopenia, osteoarthritis, and osteoporosis-related fractures.

Combination Therapies

According to certain embodiments of the methods of the present disclosure, anti-GDF-8 antibodies can be administered in a composition as a monotherapy or as a combination therapy with at least a second therapeutic agent. Typically, but not in all cases, the second therapeutic agent is chosen to treat or prevent the same condition or disorder targeted by the anti-GDF-8 antibody. In other embodiments, however, the second agent can be chosen to treat or prevent a different condition or disorder. Doses of antibody and a second therapeutic agent for use in a combination therapy are selected according to the knowledge of those ordinarily skilled in the art to maximize efficacy and minimize side effects.

The anti-GDF-8 antibody compositions of the present disclosure can be administered to a subject using the same or different mode of administration than a second therapeutic agent. Depending on the chemical and physical characteristics of the anti-GDF-8 antibodies and second therapeutic agent, they may be combined into the same composition. In alternative embodiments, they are administered as separate compositions. Compositions of antibodies and second therapeutic agents can conveniently be included in kits according to the present disclosure.

If administered as a combination therapy, the antibody and second therapeutic agent may be administered concurrently, successively, or separately.

Concurrent administration occurs when two or more agents are administered at the same time, even where the respective administrations overlap, but begin or end at different times. Successive administration occurs when two or more agents are administered to a subject on the same day, for example during the same clinic visit, but not concurrently.

Successive administration can occur 1, 2, 3, 4, 5, 6, 7, 8 or more hours apart. An anti-GDF-8 antibody composition may be administered first, followed by the second agent, or vice versa.

Separate administration occurs when the agents are administered to a subject on different days. Exemplary intervals between separate administrations of agents can be 1-day, 2-days, 3-days, 4-days, 5-days, 6-days, one-week, 2-weeks, 3-weeks or a month or more. As with successive administration, administration of the anti-GDF-8 antibody composition can precede or follow the separate administration of the second agent.

In certain other embodiments of the present disclosure, an anti-GDF-8 antibody composition and a second therapeutic agent can be administered repeatedly in an alternating pattern, whether administered successively or separately.

In methods for treating or preventing a metabolic disorder, the anti-GDF-8 antibodies of the present disclosure can be combined with a second agent effective to treat or prevent such disorders. Non-limiting examples of second agents effective for this purpose include metformin, sulfonylureas, insulin, pramlintide, thiazolidinediones, such as rosiglitazone and pioglitazone, GLP-1 analogs, such as exenitide, and DPP-IV inhibitors, such as vildagliptin.

In methods for treating or preventing a bone loss disorder, the anti-GDF-8 antibodies of the present disclosure can be combined with a second agent effective to treat or prevent such disorders. Non-limiting examples of second agents effective for this purpose include bisphosphonates, such as alendronate and risedronate, calcitonin, raloxifene, and hormonal agents such estrogen or parathyroid hormone (PTH).

In methods for treating or preventing muscular dystrophy, the anti-GDF-8 antibodies of the present disclosure can be combined with a second agent effective to treat or prevent muscular dystrophy, such as a corticosteroid. Other agents effective to treat or prevent muscular dystrophy are known in the art. Non-limiting examples of corticosteroids effective to treat muscular dystrophy include methylprednisolone, deflazacort, betamethasone, prednisolone, hydrocortisone, cortisone, beclomethasone, budesonide, cortisol, dexamethasone, fluticason, prednisone, mometasone, triamcinolone, and derivatives thereof. In other embodiments, anti-GDF-8 antibodies can be administered with agents for treating the cardiomyopathy that often occurs in DMD patients, particularly older DMD patients. Such agents include, but are not necessarily limited to beta adrenergic blockers and inhibitors of angiotensin-converting enzymes.

In methods for treating or preventing ALS, the anti-GDF-8 antibodies of the present disclosure can be combined with a second agent effective to treat or prevent ALS including, but not necessarily limited to riluzole, talampanel, glycopyrrolate, benztropine, scopolamine, atropine, trihexyphenidyl hydrochloride, amitriptyline, fluvoxamine, baclofen, tizanidine, dantrolene, diazepam, quinine, phenytoin, benzodiazepines, gabapentin, anti-spasmodics, antidepressants, and morphine or other pain relievers.

According to yet other embodiments, compositions comprising the anti-GDF-8 antibodies of the present disclosure can be administered in concert with non-drug based therapies, including by way of example, not limitation, exercise, physical therapy, respiratory therapy, ventilatory support, cardiotherapy, and nutritional supplements.

Effective Dosages

As described above, compositions comprising anti-GDF-8 antibodies of the present disclosure may be administered to a subject in need of treating or preventing certain conditions or disorders in a dosage effective to achieve, at least partially, the desired therapeutic benefit.

Binding all GDF-8 is not necessarily required to achieve therapeutic efficacy. Rather, reducing the concentration of mature, active GDF-8 within a body fluid, such blood or serum, or within a body tissue, such as muscle or other body tissues or organs, may also be effective.

In accordance with the knowledge of those ordinarily skilled in the art, the dose of an anti-GDF-8 antibody composition can be titrated in a patient so as to reduce the active GDF-8 concentration in a tissue or body fluid of interest at a predetermined time after administration at least about 10%, 20%, 30%, 40%, 50%, 60%, 70%, 80%, 90%, 91%, 92%, 93%, 94%, 95%, 96%, 97%, 98%, 99%, or 100%, or about 5%-10%, about 10%-45%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, about 90%-95%, about 95%-99%, or a percentage reduction in active GDF-8 concentration ranging between any of the foregoing values.

The amount of anti-GDF-8 antibody administered to a subject will depend on a variety of factors, including the condition or disorder to be treated or prevented, the size and weight of the subject, the form, route and site of administration, the therapeutic regimen (e.g., whether a second therapeutic agent is used), the age and condition of the particular subject, the level of active GDF-8 detected in a tissue or body fluid of interest of said subject prior to beginning treatment, and the responsiveness or sensitivity of the subject to the effects of the antibody composition. The appropriate dosage can be readily determined by a person skilled in the art. Ultimately, a clinician or similar care provider will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using methods known to those of ordinary skill in the art.

Effective dosages can be estimated initially from in vitro assays. For example, an initial dose for use in animals may be formulated to achieve a circulating blood or serum concentration of anti-GDF-8 antibody that is at or above the binding affinity of the antibody for GDF-8 as measured in vitro. Calculating dosages to achieve such circulating blood or serum concentrations taking into account the bioavailability of the particular antibody is well within the capabilities of skilled artisans. For guidance, the reader is referred to Part 1: General Principles in "Goodman and Gilman's The Pharmacological Basis of Therapeutics," 11th Ed., Hardman, J. G., et al., Eds., McGraw-Hill Professional, and the references cited therein. Initial dosages can also be estimated from in vivo data, such as animal models. Ordinarily skilled artisans can routinely adapt such information to determine dosages suitable for human administration.

In certain embodiments, a dose may be determined for an individual subject by measuring the active GDF-8 concentration in serum, muscle or other body fluid or tissue of interest a number of times in the days to weeks preceding administration of the antibody composition to calculate an amount of anti-GDF-8 antibody that would be saturating, i.e., an amount that would be sufficient to bind essentially all active GDF-8. As will be appreciated by skilled artisans, the amount of any specific antibody necessary to achieve saturation for a given amount of GDF-8 in serum, muscle or elsewhere will depend, in part, on the affinity of the particular antibody for GDF-8. Methods for calculating saturating quantities for specific anti-GDF-8 antibodies, taking into consideration the pharmacokinetic properties and bioavailability of a particular antibody when necessary, are well known in the art. To insure saturation, an amount that is greater than the calculated saturating amount may be administered, for example, at least 2-, 3-, 4-, 5-, 6-, 7-, 8-, 9- or even 10-fold greater than the calculated saturating amount may be administered.

The effective dose of an anti-GDF-8 antibody composition can range from about 0.01 mg/kg to about 250 mg/kg per single (e.g., bolus) administration, multiple administrations or continuous (e.g., infusion) administration, or any effective range or value therein depending on the factors, for example, condition or disorder to be treated or prevented, etc., discussed above.

In certain embodiments, each dose can range from about 0.1 mg/kg to about 0.5 mg/kg; about 0.25 mg/kg to about 0.75 mg/kg; about 0.5 mg/kg to about 1 mg/kg; about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg; about 70 mg/kg to about 80 mg/kg; about 75 mg/kg to about 85 mg/kg; about 80 mg/kg to about 90 mg/kg; about 85 mg/kg to about 95 mg/kg; about 90 mg/kg to about 100 mg/kg; about 95 mg/kg to about 105 mg/kg; about 100 mg/kg to about 150 mg/kg; about 125 mg/kg to about 175 mg/kg; about 150 mg/kg to about 200 mg/kg; about 175 mg/kg to about 225 mg/kg; about 200 mg/kg to about 250 mg/kg. Other dosage ranges are also possible.

The amount, frequency, and duration of administration will depend on a variety of factors, such as the subject's age, weight, and disease condition. Thus, in non-limiting examples, a therapeutic regimen for administration can continue for 1 day or more, 2 days or more, 3 days or more, 4 days or more, 5 days or more, 6 days or more, 1 week or more, 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., twice daily, once daily, every two days, three days, four days, five days, six days, once weekly, once every two weeks, or once monthly. The repeated administration can be at the same dose or at a different dose. The administration can be repeated once, twice, three times, four times, five times, six times, seven times, eight times, nine times, ten times, or more. A therapeutically effective amount of anti-GDF-8 antibody composition can be administered as a single dose or over the course of a therapeutic regimen, e.g., over the course of a week, two weeks, three weeks, one month, three months, six months, one year, or longer. What constitutes an effective dose of an anti-GDF-8 antibody composition in a particular subject may vary over time as the subject's condition changes or other health issues arise.

EXAMPLES

Example 1

Transient Expression Analysis of OGD1.0.0 and OGD1.1.1

Transient expression of intact heterotetrameric OGD1.1.1 and OGD1.0.0 was tested in COS-1 M6 cells and demonstrated that OGD1.0.0 was expressed at substantially higher levels.

Briefly, DNA encoding VH0 and VH1 (SEQ ID NO:49 and 53, respectively) were cloned into mammalian IgG expression vectors so that the VH regions were each joined in frame with a nucleic acid sequence encoding the constant heavy regions of human IgG1 including three mutations abrogating effector function (SEQ ID NO:57) so as to express full length antibody heavy chain including VH0 or VH1. Similarly, DNA encoding VL0 and VL1 (SEQ ID NO:51 and 55, respectively) were cloned into mammalian IgG expression vectors so that the VL regions were each joined in frame with a nucleic acid sequence encoding the human kappa constant light region of SEQ ID NO:17 so as to express full length antibody light chain including VL0 or VL1.

After the expression vectors were created, maxiprep DNA was prepared using standard techniques. Cells were plated on to 100 mm tissue culture dishes and then transiently co-transfected with the heavy and light chain expression vectors (i.e., VH0 and VL0 combined in one plate and VH1 and VL1 combined in a second plate). TransiT (Mirus MIR2306) transfection reagent (40 µl) was added to 2 ml OptiMEM growth media plus glutamine (2 mM final concentration) at room temperature, mixed by vortexing and then incubated at room temperature for 15 minutes. Maxiprep DNA (8 µg each of heavy and light chain DNA) was added to the mixture and incubated at room temperature for 15 minutes. The transfection solution was then added to the tissue culture dishes containing 8 ml of growth media (DMEM, HIFBS, pen, strep, glutamine). After incubation for 24 hours at 37° C., 10% $CO_2$ the cells were washed with R1 CD1 serum free growth media and then grown for 48 hours at 37° C., 10% $CO_2$ in 10 ml R1CD1 (with added pen, strep, glutamine). The conditioned medium was removed from the cells, centrifuged to pellet any debris and the supernatant removed to a new tube.

The concentration of antibody produced by the transiently transfected COS-1 cells was quantitated using a total human IgG-Fc specific ELISA. Briefly, a flat bottom ELISA plate was coated with goat anti-human IgG (Pierce 31125) by adding 100 µl of the antibody in PBS (1 µg/ml) to each well and incubating overnight at room temperature. Plates were blocked with 100 µl/well of a 0.02% Casein Solution in PBS for 3 to 24 hours at room temperature and then washed. Standard and samples were serially diluted in assay buffer (0.5% BSA, 0.02% Tween-20 in PBS), dispensed to the ELISA plate (100 µl/well) and incubated for 3 to 24 hours at room temperature. After washing, goat anti-human IgG (Pierce 31413) diluted 1:5000 in assay buffer was dispensed (100 µl/well) and the plate incubated for 15 minutes at room temperature. After washing, the plate was developed by adding BioFX TMB (TMBW-0100-01) (100 µl/well). After stopping the reaction with 0.18 N $H_2SO_4$ (100 µl/well), the plate was read at 450 nm using a Molecular Devices vMax plate reader. Sample concentrations were calculated using the linear range of the curve determined from the dilution series of the standard.

The results of the transient transfection experiment are shown in the table below, in which POI stands for peak of interest by size exclusion chromatography (SEC) after protein A purification. POI represents the proportion of intact full size antibody expressed by the cells, as opposed by high molecular weight aggregates or degradation products.

Unexpectedly, the OGD1.0.0 antibody was expressed at much higher levels (i.e., more than 10-fold higher) than the OGD1.1.1 antibody under the same conditions after transient transfection. Importantly, as indicated by the POI value, the greatly increased expression levels observed are associated almost entirely with intact full size antibody as opposed to high molecular weight complexes or degradation products. This difference in expression is even more surprising in view of the fact that, as between OGD1.0.0 and OGD1.1.1, there is just one amino difference at Kabat position 108 of the VH regions (i.e., residue number 111 of SEQ ID NO:44 and 7) and one amino acid difference at Kabat position 100 of the VL region (i.e., residue number 100 of SEQ ID NO:46 and 9). See FIG. 1A and FIG. 1B.

As explained above, these structural and functional differences are attributable to the use of different J segments in VH0 and VL0 as compared to VH1 and VL1, respectively. As explained below, the most important difference appears to be the change to the VH region. Notably, it is believed that this is the first demonstration that the choice of J segment used to construct a humanized antibody can affect antibody expression levels at all, let alone to the dramatically increased extent observed here. This discovery is particularly important because it is expected to significantly reduce the cost of goods necessary to produce OGD1.0.0. Without this discovery, it would not be economic to produce this antibody in the quantities required to bring it to market to the detriment of the patient populations that may benefit from being treated with it.

TABLE 3

Comparison of OGD1.0.0 and OGD1.1.1 expressed transiently in COS cells.

| Antibody | Transient Expression in COS-1 Cells | POI |
|---|---|---|
| OGD1.0.0 | 28.45 µg/ml | >99% |
| OGD1.1.1 | 2.35 µg/ml | >99% |

Example 2

Stable Expression Analysis of OGD1.0.0 and OGD1.1.1

Stable expression of OGD1.0.0 and OGD1.1.1 was tested in CHO-DUKX cells. Briefly, cells were grown to 80% confluence and then co-transfected using a lipofectamine transfection reagent with 25 µg each of the heavy and light chain expression vectors (50 µg total) described in the previous example (i.e., VH0 and VL0 for one set of cells, and VH1 and VL1 for another set of cells). After transfection, spent media was exchanged with fresh R1 CD1 media plus 10% FBS every three to four days while the stable pools were being established.

After stable transfectants were established, the ability of the cells to express anti-GDF-8 antibody when grown as attached cells in serum free R5CD1 media was tested. Under these conditions, the cells expressing OGD1.0.0 expressed 47.3 mg/L antibody after 96 hours of growth, whereas the cells expressing OGD1.1.1 expressed 41 mg/L antibody after 72 hours of growth. Antibodies were purified using a 1 mL protein-A column and concentration then quantified using HPLC.

After attached cells were adapted to suspension growth in serum free medium, expression of OGD1.0.0 and OGD1.1.1 antibodies was again determined. AS1 serum free media was seeded with $3.0 \times 10^5$ viable cells/mL and incubated at 37° C. On the fourth day, the pH was adjusted to 7.3, feed concentrate was added, and the incubation temperature was lowered to 31° C. for an additional 3 days growth. OGD1.0.0 expressing cells were grown in 100 L culture volume, whereas OGD1.1.1 expressing cells were grown in 50 mL culture volume. All other growth conditions were the same between the cells. On the seventh day, the cells expressing OGD1.0.0 expressed 66.12 mg/L antibody, whereas the cells expressing OGD1.1.1 expressed 10.6 mg/L antibody as determined by protein-A purification and HPLC quantification. When the experiment using OGD1.0.0 cells was repeated by growing the cells in 100 L culture for 9 days, including 5 days at 31° C., the antibody concentration increased to 207.2 mg/L. In another experiment in which OGD1.0.0 expressing cells were grown in 25 L culture for 11 days, including 7 days at 31° C., the antibody concentration was 145 mg/L. In a separate experiment in which OGD1.1.1 expressing cells were grown in 50 mL culture in serum-free R5CD1 medium for 7 days, including 3 days at 31° C., the antibody concentration was 39.3 mg/L.

The results of the stable transfection experiment are shown in the table below, in which POI stands for peak of interest by size exclusion chromatography (SEC) after protein A purification. Consistent with the results obtained when OGD1.0.0 and OGD1.1.1 were expressed in transiently transfected COS-1 cells, the expression levels of the OGD1.0.0 antibody were substantially higher in stably transfected CHO cells compared to expression of OGD1.1.1 under similar conditions. This surprising result is consistent with the increase in expression level observed in the transient transfection experiment, above. This result also suggests that the manner in which the expressing cells are cultured, whether adherent or in suspension, and cell type, does not substantially affect the enhanced expression of the OGD1.0.0 antibody compared to OGD1.1.1.

TABLE 4

Comparison of expression levels of OGD1.0.0 and OGD1.1.1 expressed stably in CHO cells.

| Antibody | CHO Stable Pool |
|---|---|
| OGD1.0.0 | 66.1 mg/L |
| OGD1.1.1 | 10.6 mg/L |

Example 3

Transient Expression Analysis of OGD1.0.1 and OGD1.1.0

Because the J segments in each of the heavy and light chain variable regions were changed, it was unclear whether either change alone might be sufficient to cause the markedly higher expression levels of OGD1.0.0 that were observed, or possibly whether both changes contributed to increased antibody expression.

To study this, applicants repeated the transient transfection experiment described above, but additionally combined VH0 and VL1 constructs in one plate, and combined VH1 and VL0 constructs in another plate, and then quantified the antibody expression levels using ELISA. The results of the experiment, which are shown in the table below, demonstrate that substitution of the JH4 for the JH3 J segment in the VH region is sufficient to confer the greatly increased antibody expression observed by applicants. Conversely, changing the kappa J segments (i.e., JK4 for JK1) did not appear substantially to impact expression levels.

TABLE 5

Effect on antibody expression of combining VH1 with VL0 and VH0 and VL1

| Antibody | Expression |
| --- | --- |
| OGD1.0.0 | 28.5 μg/ml |
| OGD1.0.1 | 27.6 μg/ml |
| OGD1.1.0 | 1.9 μg/ml |
| OGD1.1.1 | 2.4 μg/ml |

Example 4

GDF-8-Binding by Anti-GDF-8 Antibodies

GDF-8 binding by the parental murine antibody, chimeric mouse-human antibody (murine variable domains and human constant domains) and humanized antibodies OGD1.0.0 and OGD1.1.1 were analyzed using quantitative ELISA and surface plasmon resonance (SPR). In the ELISA experiments, the ability of the antibodies to inhibit GDF-8 binding to its cognate high affinity receptor ActRIIB was determined by calculating $IC_{50}$ values. SPR analysis was used to calculate apparent $K_D$ values. Results are shown in Table 6.

For ELISA, ActRIIB-Fc fusion protein (1 μg/ml in 0.2 M sodium carbonate buffer) was coated on 96 well flat-bottom assay plates overnight at 4° C. Coated plates were then blocked with 1 mg/ml BSA in PBS 0.1% Tween (200 μl/well) for 1 hour at room temperature or overnight at 4° C. and then washed. Different antibody concentrations were combined with 10 ng/ml GDF-8 conjugated to biotin and incubated for 45 minutes at room temperature. After incubation, the test solution was added to the blocked ELISA plate (100 μl/well) and further incubated for 1 hour at room temperature. After washing the wells, the amount of GDF-8 bound to the immobilized ActRIIB-Fc relative to control was detected with streptavidin-horseradish peroxidase (30 minute incubation) and TMB. Colorimetric measurements at 450 nm were recorded in a microplate reader. Experiments using murine and chimeric antibodies were repeated four times each and averaged.

SPR was performed at 25° C. using a BIACORE 3000 (GE Healthcare) machine. The murine antibody was captured using anti-mouse IgG antibodies, whereas the humanized antibodies was captured using protein A. Protein A was immobilized on all four flow cells of a CM5 sensorchip using amine coupling chemistry. The surface was activated by injecting a solution of 0.2M N-ethyl-N-dimethyl-aminopropyl-carbodiimide (EDC) and 50 mM N-hydroxysuccinimide (NHS) for 7 minutes. Protein A was diluted to 50 μg/ml in 10 mM Sodium acetate buffer at pH 5.0 and injected for 3 minutes at a flow rate of 10 μl per minute. The surface was then blocked with 1M ethanolamine (ETH) for 7 minutes. Final immobilization levels of protein A were between 1000-1200 Response Units (RU). The immobilization procedure was followed by several washes with running buffer (0.01 M HEPES pH 7.4, 0.15 M NaCl, 3 mM EDTA, 0.005% P20) to equilibrate the surface. Antibodies were diluted to 0.25 μg/ml in HBS-EP buffer. Solutions of each antibody (5 μl) were injected over Protein A coated flow cells 2, 3 or 4 at a rate of 10 μl/min, yielding approximately 200 RU of captured antibody. A GDF-8 titration series (2-fold dilutions from 4.0 nM to 0.125 nM) was prepared in 0.01M Sodium acetate at pH 5.0, 0.15M NaCl, 3 mM EDTA, 0.005% P20. The latter solution was also used as running buffer. GDF-8 solution was injected over the captured antibody for 2 minutes at a flow rate of 50 μl/min and allowed to dissociate for 30 min. After each cycle of injection and capture the sensor chip surface was regenerated with 30 μl of 10 mM NaPO4, 0.5 M NaCl at pH 2.5 at a flow rate of 50 μl/min. BIAevaluation software (ver. 4.1.1, GE Healthcare) was used for data analysis. Data were double referenced by subtracting the signal contributed by the buffer and the reference surface. A Langmuir 1:1 model was used to globally fit the sensorgram data and calculate $K_D$ values. Experiments using OGD1.0.0 were repeated three times each and averaged.

$IC_{50}$ values determined using ELISA are comparable among the antibody versions tested. In the more precise SPR assay, OGD1.0.0 had a substantially greater binding affinity for GDF-8 compared to OGD1.1.1.

TABLE 6

GDF-8-binding by anti-GDF-8 antibodies

| Antibody | $IC_{50}$ (nM) by ELISA | $K_D$ by Biacore |
| --- | --- | --- |
| Murine antibody | 0.165 nM | 21.83 pM |
| Chimeric antibody | 0.165 nM | 2.99 pM |
| OGD1.0.0 | 0.140 nM | 2.59 pM |
| OGD1.1.1 | 0.140 nM | 7.25 pM |

Example 5

GDF-8 Neutralizing Ability of OGD1.0.0 Antibody

The ability of anti-GDF-8 antibodies to neutralize GDF-8 mediated signaling was confirmed using a reporter gene assay. The reporter construct, called pGL3(CAGA)$_{12}$, was constructed by placing 12 GAGA boxes upstream of the TATA box and transcription initiation site from the adenovirus major later promoter in luciferase reporter vector pGL3 (Promega). The GAGA box, which is found in the promoter of the PAI-1 gene, is a TGFβ response element that also responds to GDF-8. The human rhabdomyosarcoma cell line A204 (ATCC HTB-82) was transiently transfected with pGL3(CAGA)$_{12}$ and cultured in 96-well plates in McCoy's 5A medium supplemented with 2 mM glutamine, 100 U/ml streptomycin, 100 μg/ml penicillin and 10% fetal calf serum for 16 hrs. Antibodies were preincubated with GDF-8 (10 ng/ml) in medium supplemented with 1 mg/ml BSA for 1 hr at room temperature. Cells were then treated for 6 hrs at 37° C. with the test samples and controls including no GDF-8 and GDF-8 (10 ng/ml) with no antibody added. Luciferase activity was measured using the Luciferase Assay System (Promega). Experiments using the murine and chimeric antibodies were repeated two times each and averaged, whereas experiments using OGD1.0.0 were repeated three times and averaged. $EC_{50}$ values determined using reporter gene assay are comparable among the antibody versions tested.

TABLE 7

GDF-8 neutralizing activity of anti-GDF-8 antibodies

| Antibody | CAGA EC50 nM |
|---|---|
| Murine antibody | 33.50 nM |
| Chimeric antibody | 24.25 nM |
| OGD1.0.0 | 27.30 nM |
| OGD1.1.1 | 26.00 nM |

Example 6

OGD1.0.0 Antibody Increases Muscle Mass, Muscle Force and Lean Mass in Mice

Eight-week old male C57Bl/6 mice were dosed intraperitoneally (IP) once per week for two weeks with OGD1.0.0 (10 mg/kg) or vehicle control (PBS). A total of eight mice were used for each group. At day 14, the full body lean mass was determined by small animal NMR imaging. After lean mass was determined, the animals were euthanized and the gastrocnemius, quadriceps, and extensor digitalis longus (EDL) muscles were dissected and weighed. The EDL muscle was also tested for its ability to generate force ex vivo.

After two weeks of treatment, the lean mass of control animals increased by 1.66±0.56 g while the lean mass of animals treated with OGD1.0.0 increased by 3.36±0.62 g, which represents a 102% increase over controls.

Figure 2B:
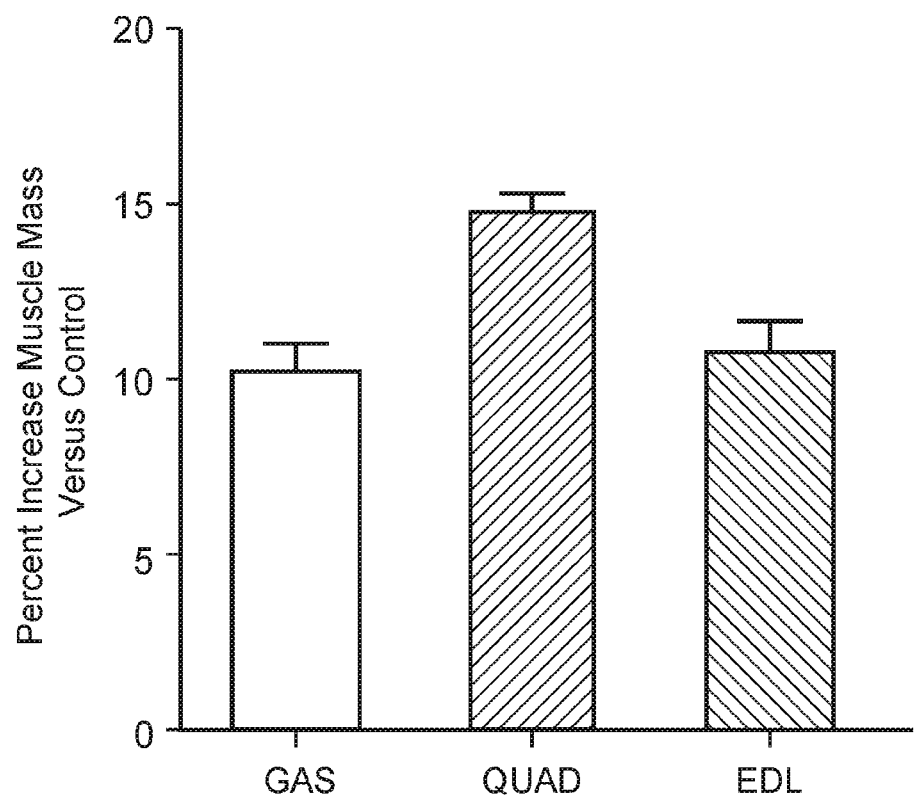
FIG. 2B reports the same data in FIG. 2A as a percentage increase in the mass of the muscles in mice treated with OGD1.0.0 antibody relative to control.
Figure 3:
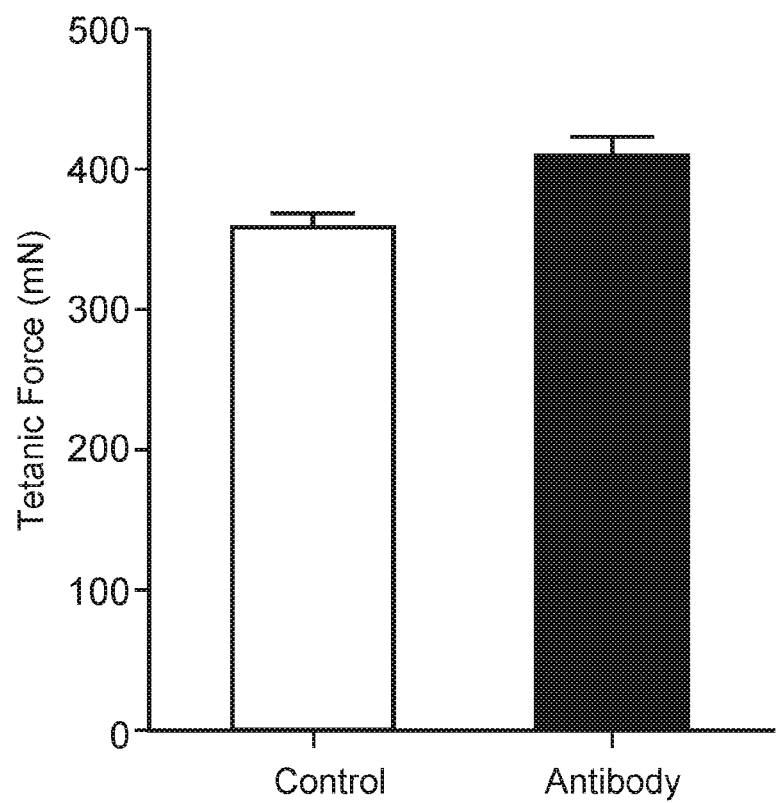
FIG. 3 provides a graph showing the increase in total tetanic force generated by the EDL muscle from C57Bl/6 mice treated for two weeks with 10 mg/kg OGD1.0.0 antibody compared to vehicle control.

As shown in FIG. 2A and FIG. 2B, quadriceps mass increased 14.8% compared to control, gastrocnemius mass increased 10.3% compared to control and EDL muscle mass increased 10.8% compared to control in the animals treated with OGD1.0.0 antibody. As shown in FIG. 3, in the animals treated with OGD1.0.0 antibody, total tetanic force exerted by the EDL muscle increased 14.8% relative to the force generated by EDL muscle from mice treated with vehicle control. Data is shown as mean±SEM.

Figure 4B:
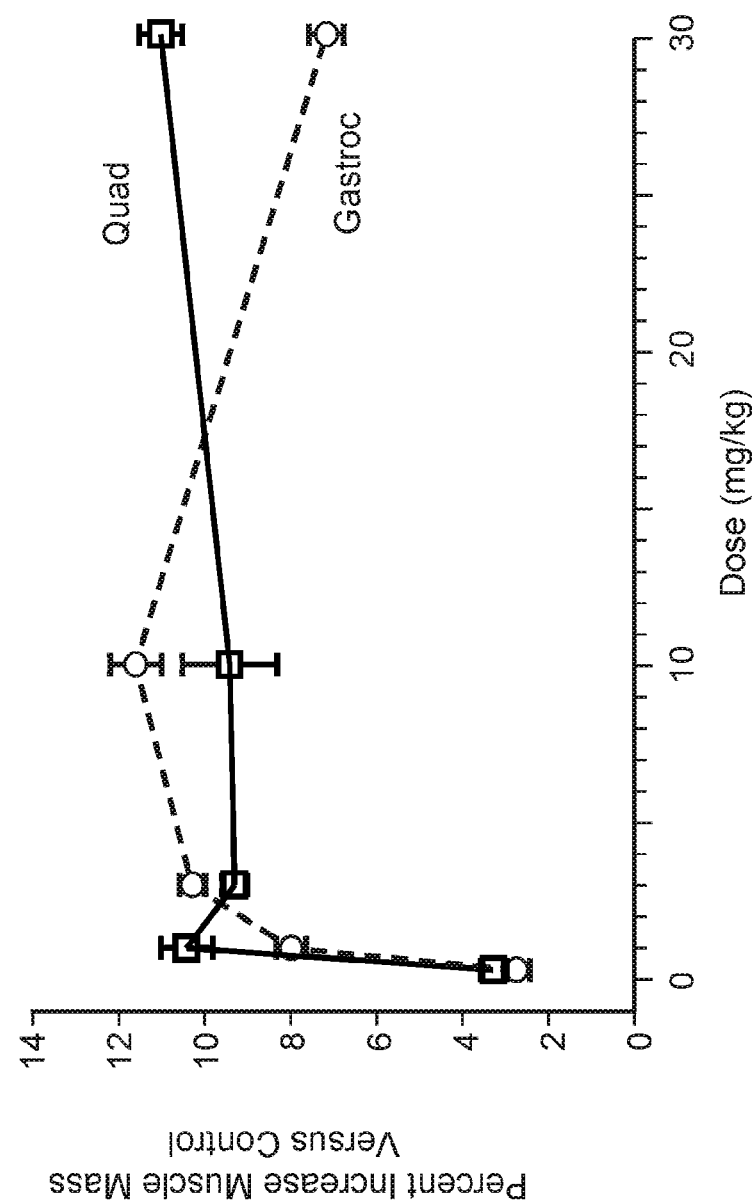
FIG. 4B reports the same data in FIG. 4A as a percentage increase in the mass of the gastrocnemius and quadriceps muscles in mice treated with OGD1.0.0 antibody relative to control.
Figure 5B:
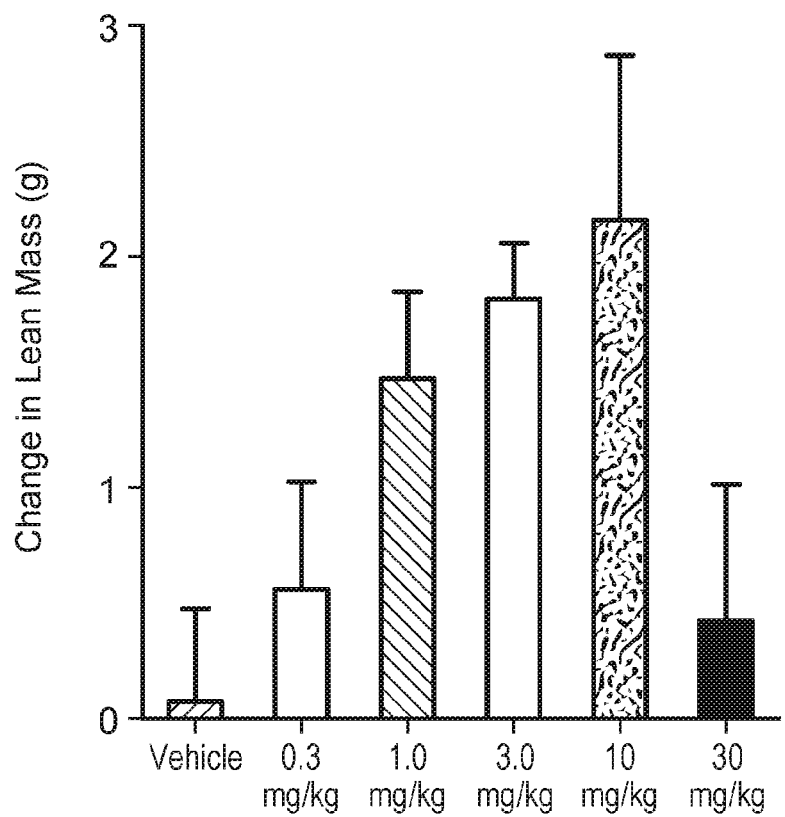
FIG. 5B provides a graph showing the increase in total body lean mass of C57Bl/6 mice treated weekly for four weeks with PBS vehicle, and 0.3, 1, 3, 10 and 30 mg/kg OGD1.0.0 antibody at the end of the four week study.

Dose responsiveness of total body lean mass and muscle mass of the quadriceps and gastrocnemius in response to OGD1.0.0 treatment was also determined. In these experiments, 12-week-old female C57Bl/6 mice were divided into groups (n=6) and treated weekly with vehicle or OGD1.0.0 at 0.3, 1, 3, 10, or 30 mg/kg for 4 weeks. At 7, 14, 21 and 28 days of the treatment period, lean mass was determined using NMR imaging. At the end of the study period, quadriceps and gastrocnemius muscles were dissected and weighed after euthanizing the test animals. As shown in FIG. 4A and FIG. 4B, muscle mass of the quadriceps and gastrocnemius muscles increased with rising antibody dose up to about 10 mg/kg. Similarly, as shown in FIG. 5A and FIG. 5B, total body lean mass increased with rising antibody dose up to about 10 mg/kg. Data is shown as mean±SEM.

Example 7

OGD1.0.0 Antibody Increases Muscle Mass and Lean Mass in Mdx Mice

The mdx mutation of the X-linked dystrophin gene (Dmd) arose spontaneously in C57BL/10ScSn mice and causes a point mutation within an exon at gene position 3185 converting a glutamine codon to a termination codon and resulting in premature termination of the dystrophin protein. As a result, mdx mice lack functional dystrophin and serve as a small animal model of human Duchenne muscular dystrophy. Starting around 3 weeks muscle necrosis develops with some visible muscle weakness. While skeletal limb muscles are characterized by a persistent and progressive degeneration and necrosis, this is offset by a regenerative response activated by satellite cells and muscle hypertrophy. The muscles of mdx mutants have an overall reduction in elasticity, making them more susceptible to injury due to lengthening-activation. Leg muscles in mutant mice initially develop normally, but the differentiation of regenerated myotubes into both fast and slow fiber types is significantly inhibited. The comparatively mild phenotype of the mdx mice can, in part, be attributed to the compensatory function of the dystrophin-related protein utrophin, which is highly upregulated in regenerating muscle fibers in adult mdx mutants. In contrast to limb muscles, the diaphragm muscles of mdx mice do not undergo a significant regeneration phase such that the continuous dystrophy weakens these muscles with age. The specific twitch force, specific tetanic force and maximum power are all reduced in the diaphragm of mdx mutants.

Eight-week old male mdx and control C57Bl/6 mice were dosed intraperitoneally (IP) once per week for eight weeks with OGD1.0.0 (10 mg/kg) or vehicle control (PBS). In these experiments, ten mdx mice were treated with antibody, eight were administered vehicle control, and six C57Bl/6 mice each were treated with antibody or PBS. At the end of the treatment period, full body lean mass, grip strength, and muscle mass were measured. Full body lean mass was determined by small animal NMR imaging. Grip strength was tested by placing a test animal on a wire grid, allowing it to grip the mesh with all limbs, and then pulling on the tail and measuring maximal peak force as the animal released its grip. Data per animal was averaged from 3-5 trials. After measuring lean body mass and grip strength, the mice were euthanized and the quadriceps and gastrocnemius muscles were dissected and weighed.

Figure 6A:
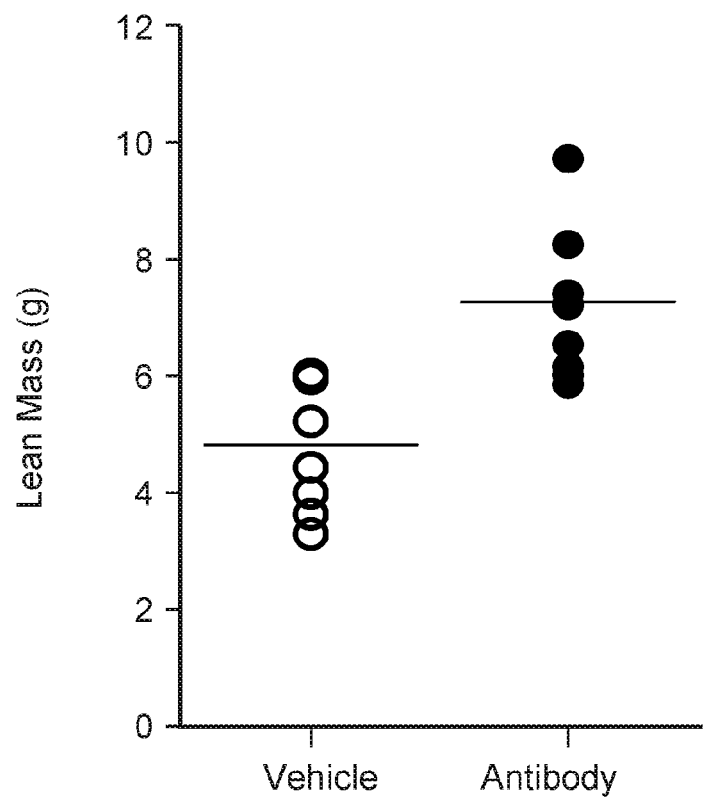
FIG. 6A provides a graph showing the increase in total body lean mass of mdx mice treated weekly for eight weeks with 10 mg/kg OGD1.0.0 antibody relative to control mdx mice administered PBS vehicle.
Figure 6B:
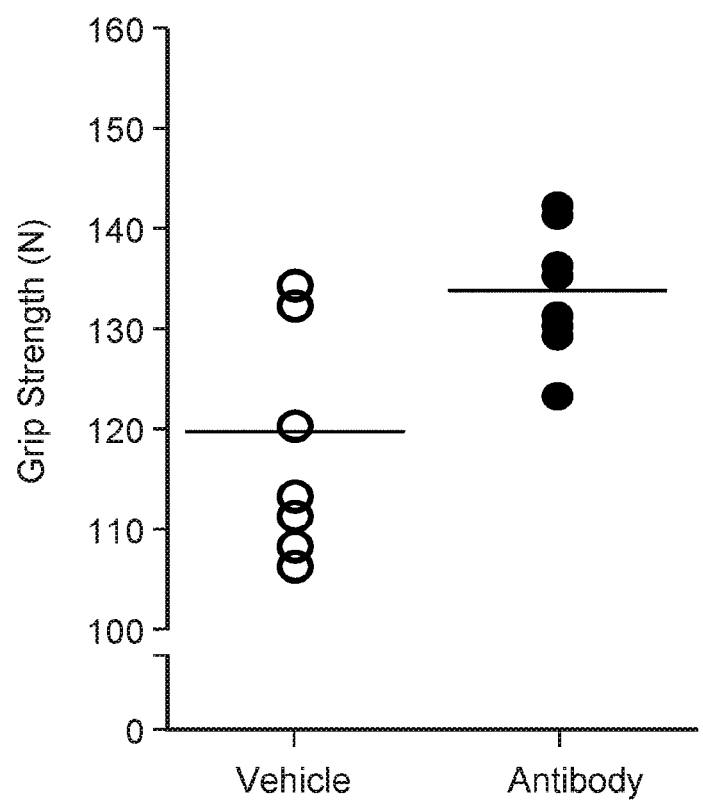
FIG. 6B provides a graph showing the increase in maximal peak grip force of mdx mice treated weekly for eight weeks with 10 mg/kg OGD1.0.0 antibody relative to control mdx mice administered PBS vehicle.

As shown in FIG. 6A, treatment with OGD1.0.0 antibody increased lean mass in the mdx mice an average 7.28±0.4 g compared to an average 4.83±0.4 g in mdx mice treated with PBS. The difference was statistically significant at p<0.05. Thus, lean mass increased by 50%±8.2% in mdx mice over the vehicle treated controls in the eight week study. As shown in FIG. 6B, antibody treatment also increased grip strength in mdx mice compared to vehicle treated controls. The difference was statistically significant at p<0.05.

Figure 7A:
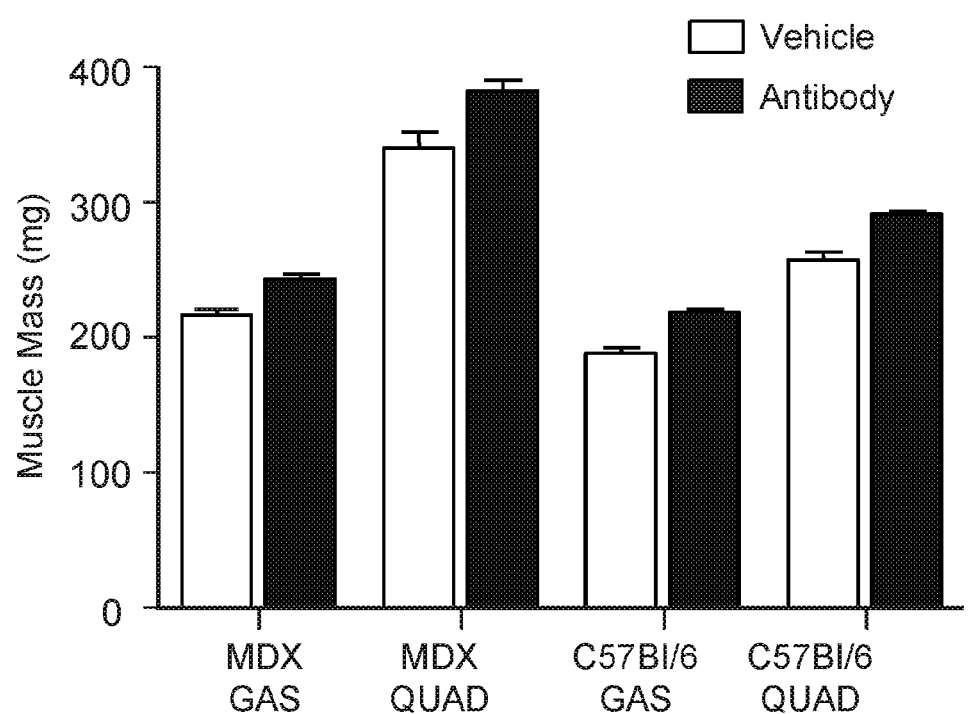
FIG. 7A provides a graph showing the increase in mass of gastrocnemius and quadriceps muscles from mdx mice and C57Bl/6 mice treated weekly for eight weeks with 10 mg/kg OGD1.0.0 antibody relative to control mice administered PBS vehicle. Data represents the muscle mass measured at the end of eight weeks.
Figure 7B:
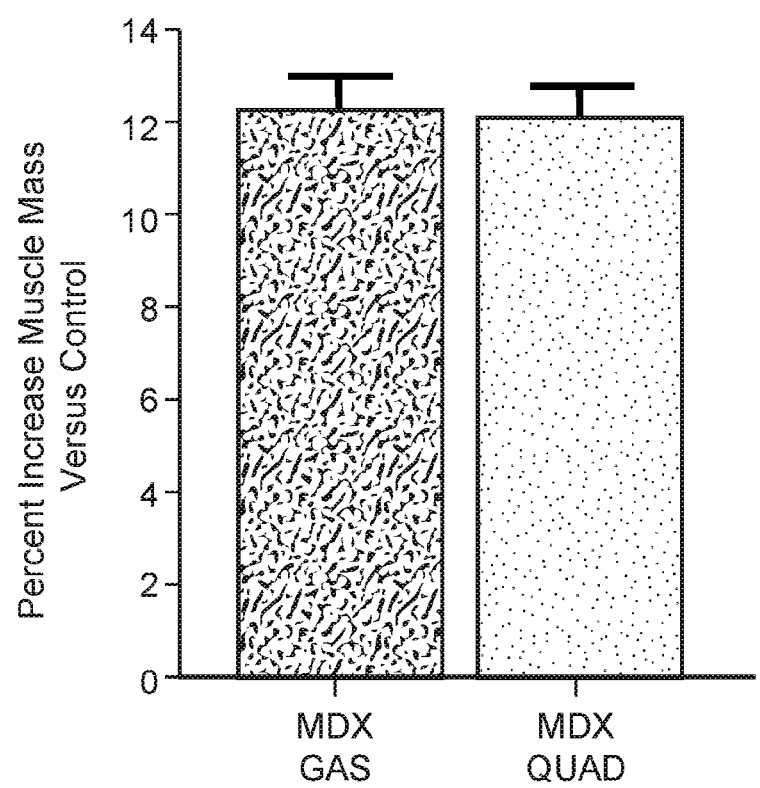
FIG. 7B reports the same data in FIG. 7A as a percentage increase in the mass of the gastrocnemius and quadriceps muscles in mcx mice treated with OGD1.0.0 antibody relative to control.

As shown in FIG. 7A antibody treatment increased the mass of gastrocnemius and quadriceps muscles in mdx and C57Bl/6 mice compared to the same type of mice treated with PBS. The increases were statistically significant (p=0.005 and p=0.002 for mdx quadriceps and gastrocnemius, respectively, and p=0.001 and p=0.003 for C57Bl/6 quadriceps and gastrocnemius, respectively). As shown in FIG. 7B, the mass of gastrocnemius and quadriceps muscles from antibody treated mdx mice increased 12.2% and 12.1%, respectively, compared to vehicle treated control mice. The mass of the same types of muscles from C57Bl/6 mice also increased by 15.2% and 12.8% after treatment with antibody compared to vehicle treated controls (not shown).

Example 8

OGD1.0.0 Antibody Increases Muscle Volume and Lean Mass in Non-Human Primates

Two studies investigating the effect of OGD1.0.0 antibody administration in cynomolgus monkeys on lean body mass and muscle volume were designed and carried out.

Each study lasted eight weeks, in which animals were dosed with antibody weekly by IV administration and provided excess food to ensure a positive nitrogen balance. In the first study, each of three male and three female subjects were administered PBS vehicle or OGD1.0.0 antibody at doses of 3.0 mg/kg, 10 mg/kg, and 30 mg/kg. Before the first treatment and then at week four and week eight, animals were anesthetized and then imaged using dual-energy X-ray absorptiometry (DEXA), computerized x-ray tomography (CT) and magnetic resonance imaging (MRI) to detect and measure body composition, including lean mass and fat content. Subject animals from Study 1 were then euthanized and necropsied. In the second study, only male subjects were used and received vehicle alone (n=5) or OGD1.0.0 antibody at doses of 10 mg/kg and 30 mg/kg (n=5 and n=3 subjects, respectively). The subject animals were imaged at eight weeks as in the first study. Thereafter, the animals were maintained on a supplemented diet and imaged again at 12, 17 and 26 weeks.

Figure 8:
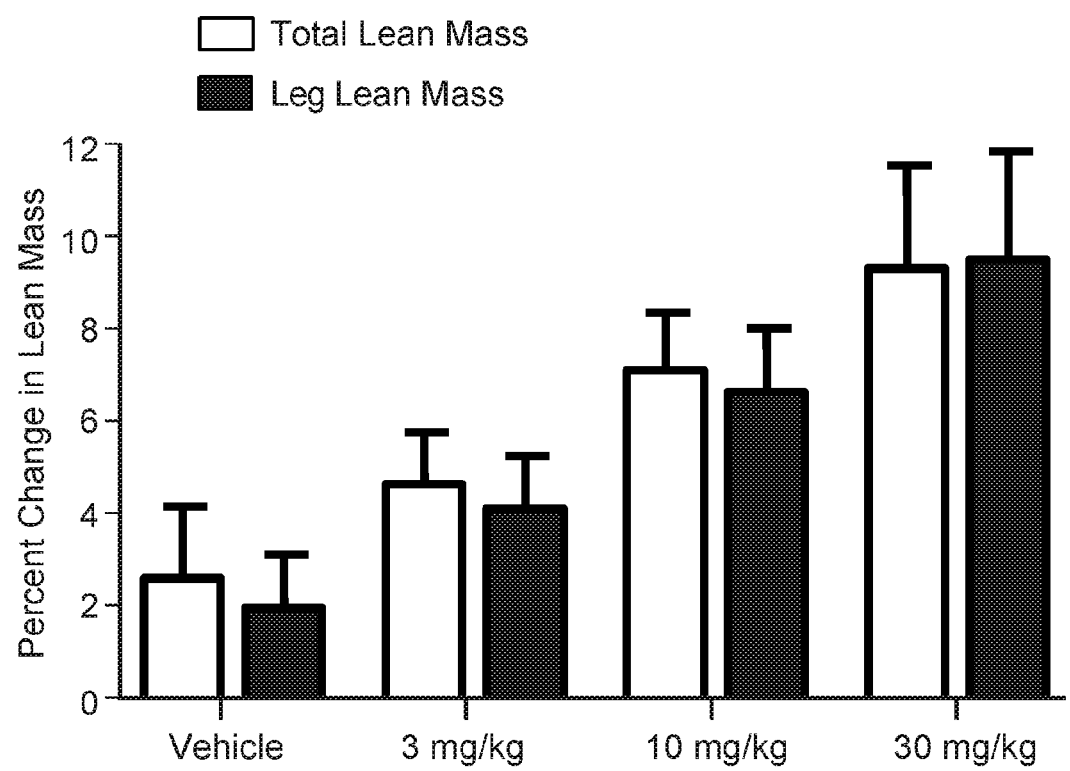
FIG. 8 provides a graph showing the of dose responsive increase in total body lean mass and leg lean mass in cynomolgus monkeys treated with 0, 3, 10, and 30 mg/kg OGD1.0.0 antibody.

The eight week data for lean body mass measured by DEXA from both studies was combined and analyzed. The results are shown in FIG. 8, which demonstrates that after eight weeks of treatment with OGD1.0.0 antibody there was a dose responsive increase in total lean mass and leg lean mass. Data is expressed as the mean±SEM. The number of subjects included in the study were, for vehicle only, n=11, for 3 mg/kg antibody, n=6, for 10 mg/kg, n=10, and for 30 mg/kg, n=8. The increase in total body lean mass and leg lean mass over vehicle treated controls was statistically significant (p<0.05) at all antibody doses tested. Further, the increase in leg lean mass in subjects treated with 30 mg/kg over 10 mg/kg was also found to reach statistical significance (p<0.05).

Figure 9:
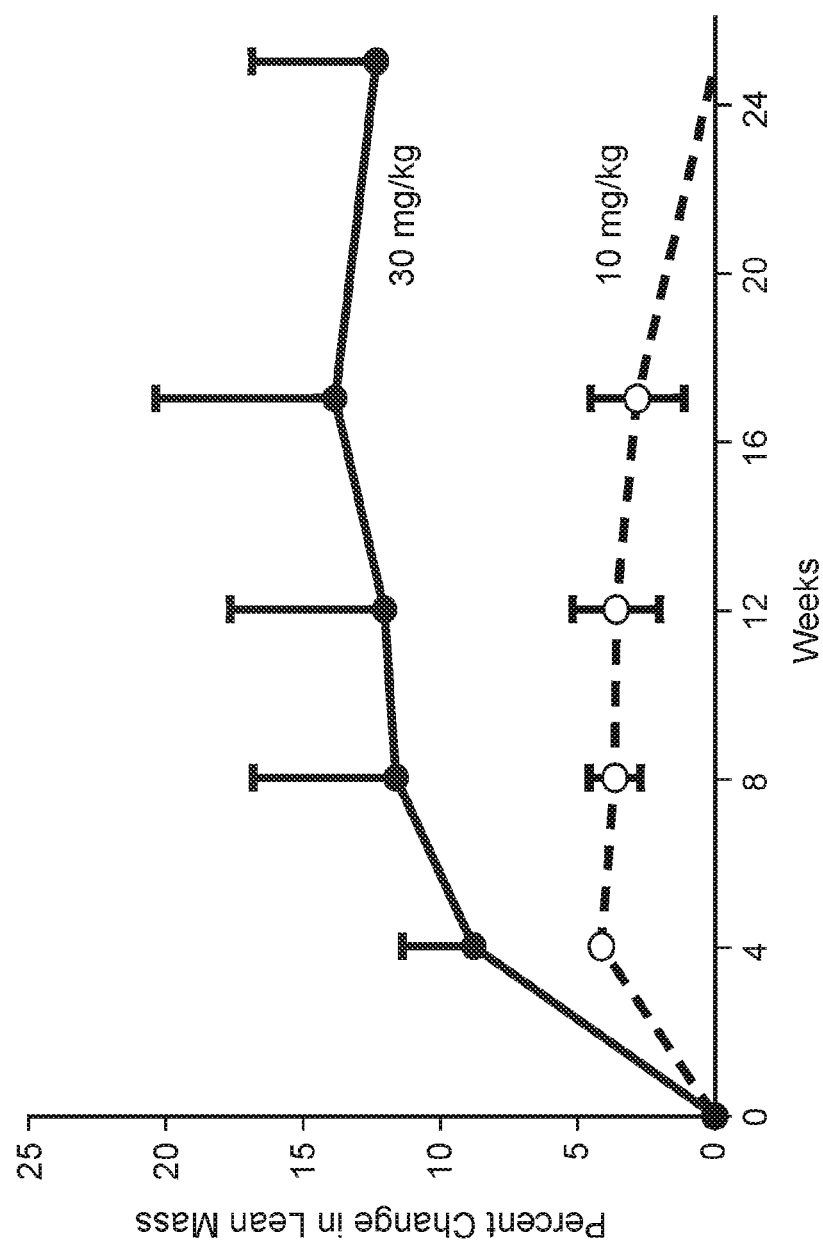
FIG. 9 provides a graph showing that the increase in total lean body mass of cynomolgus monkeys treated with both 10 mg/kg and 30 mg/kg OGD1.0.0 antibody persisted for a number of weeks after treatment with the antibody was discontinued.

Interestingly, as shown in FIG. 9, the increase in lean body mass among subjects in the second study treated with 10 mg/kg and 30 mg/kg OGD1.0.0 antibody persisted for a period of weeks following the last antibody dose at week seven. The data is shown as the difference compared to PBS vehicle at each time point. The increase relative to control for the higher dose was statistically significant at p<0.05 at all weeks shown. The increase for the lower dose was statistically significant at weeks 4 and 8 at p<0.09.

Figure 10A:
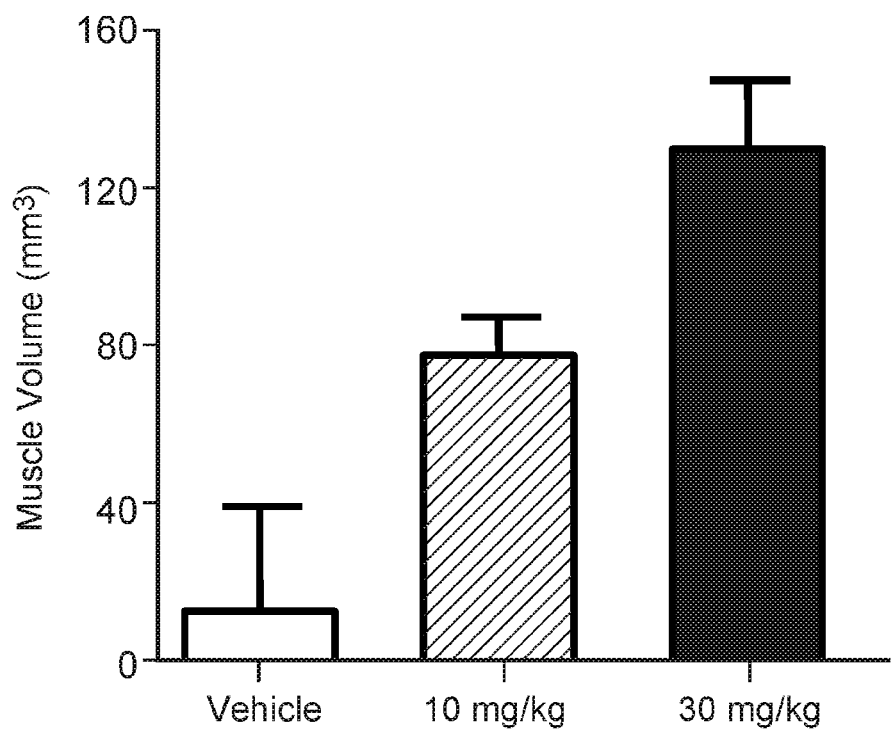
FIG. 10A provides a graph showing that the volume of the epaxial muscles overlying the L3-L5 vertebrae of cynomolgus monkeys treated with 10 mg/kg and 30 mg/kg OGD1.0.0 antibody for 8 weeks increased relative to control animals administered PBS vehicle.
Figure 10B:
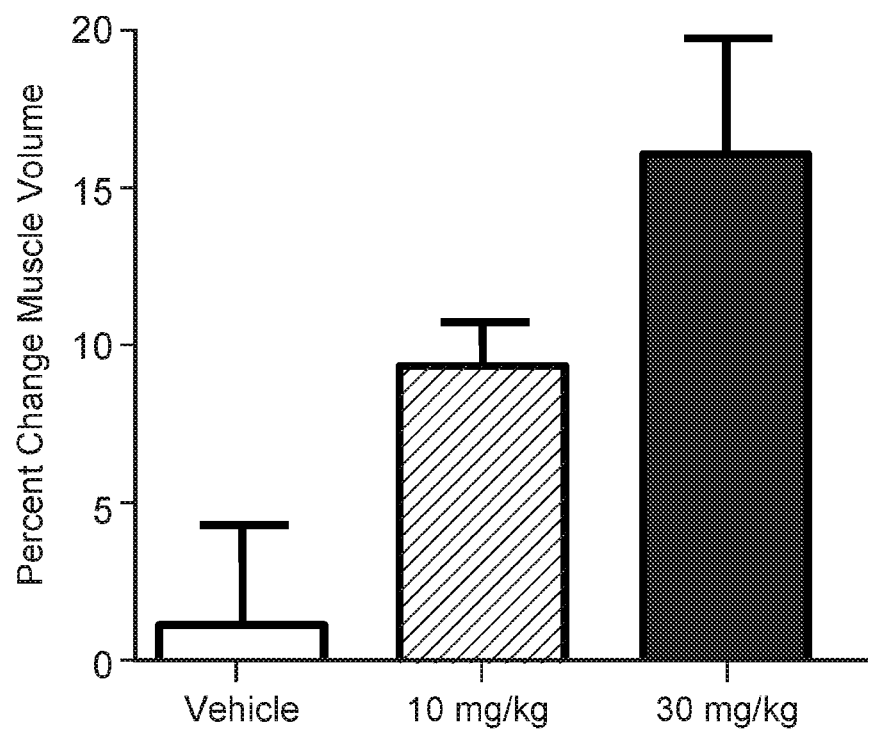
FIG. 10B shows a graph of the same data as shown in FIG. 10A but expressed as a percentage change compared to baseline.

The effect of OGD1.0.0 antibody treatment on the volume of the epaxial muscles lying dorsal to the vertebral column over lumbar vertebrae L3-L5 was measured by CT scan. As shown in FIG. 10A and FIG. 10B, epaxial volume increased substantially in subject animals treated with 10 mg/kg (n=5) and 30 mg/kg (n=3) OGD1.0.0 antibody for 8 weeks compared to controls administered PBS. The increase in muscle volume was statistically significant at p<0.05.

Figure 11:
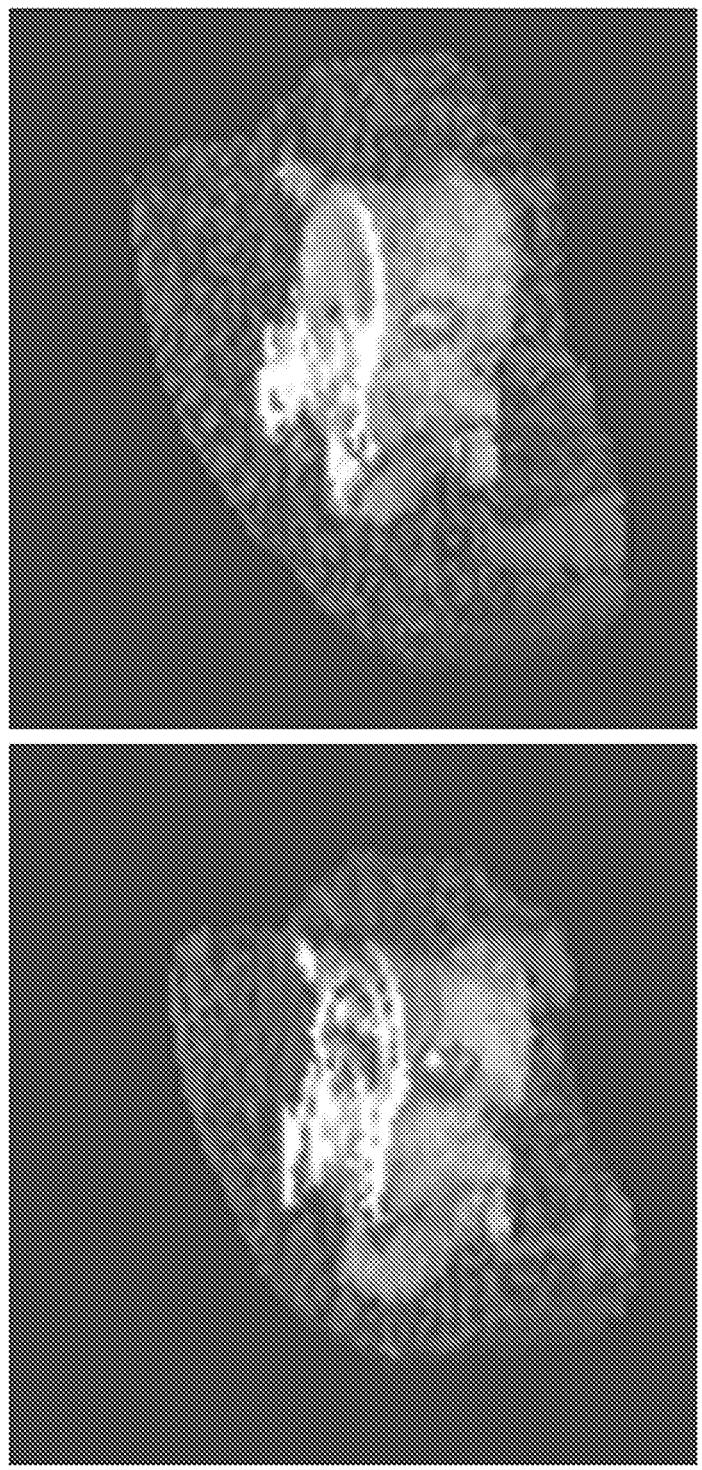
FIG. 11 provides a 3D rendering of an epaxial muscle from an exemplary animal subject before and after 4 weeks treatment with OGD1.0.0 antibody.

FIG. 11 is a 3D rendering of the epaxial muscle from an exemplary test subject after 4 weeks treatment with 30 mg/kg OGD1.0.0 antibody. Compared to baseline (left) the resulting increase in muscle volume, which is visually apparent (right), was 22%.

Example 9

OGD1.0.0 Antibody Lacks Fc Domain Effector Function

Binding by OGD1.0.0 antibody including three mutations in the Fc region known to abrogate Fcγ receptor (FcγR) binding to a panel of Fcγ receptors was tested using surface plasmon resonance. All experiments were performed using a Biacore T200 instrument (GE HealthCare). Briefly, 100 RU of GDF-8 was captured on a sensor chip-SA via the biotin tag to which approximately 100RU of OGD1.0.0 antibody was captured followed by flow of FcγRs in the concentration range of 0-21 μM for CD32a-131 H, CD16a-158V, CD32b and 0-270 nM for CD64. For each FcγR binding experiment, injections were conducted in series using single-cycle kinetics mode. The association and dissociation phases lasted 120 s each. At the end of the dissociation phase following the last injection, the surface containing GDF-8 was regenerated using a 20 s pulse of 0.1% TFA solution.

No binding to CD16, CD32a and CD64 was observed. In contrast, binding to CD32b was observed but only at the highest concentration tested (21 μM). Due to the lack of data points above 21 μM an accurate Kd was not determined but can be assumed to be above 21 μM, which is considered very weak compared to the Kd of wild type IgG1 molecules (i.e., 2-4 μM). These results indicate that OGD1.0.0 antibody will have no or substantially reduced ability to induce effector functions.

Example 10

Crystal Structure of Anti-GDF-8 Antibodies Bound to GDF-8

As explained in this example, the crystal structure of chimeric mouse and humanized anti-GDF-8 antibodies bound to human GDF-8 were solved and used to determine the identities of amino acids within the antibodies and GDF-8 that contact each other.

Fab fragments were prepared from chimeric anti-GDF-8 antibody containing murine VH and VL regions (SEQ ID NO:3 and SEQ ID NO:5, respectively) joined with human IgG1 constant regions. The Fab fragments were then mixed with human GDF-8 protein to form bound complexes. Protein complexes were concentrated to 10.75 mg/mL in 50 mM tris hydrochloride pH 7.5 and 100 mM sodium chloride. Crystals were formed using the hanging drop method with equilibration at 18° C. against a solution containing 20% PEG MME 5000 and 100 mM bis-tris pH 6.5. Crystals containing Fab prepared from humanized anti-GDF-8 antibody OGD1.0.0 and GDF-8 were prepared similarly except the protein solution was equilibrated against an unbuffered solution containing 20% PEG 3350 and 200 mM sodium chloride.

Single-wavelength (1.0 Å) data for each crystal was collected on the ID beamline at SER-CAT, Advanced Photon Source, Argonne National Laboratory. A single crystal, cooled to −180° C., was used for each data set. Data was processed using DENZO and Scalepack (Z. Otwinowski and W. Minor, "Processing of X-ray Diffraction Data Collected in Oscillation Mode", Methods in Enzymology, Volume 276: Macromolecular Crystallography, part A, p. 307-326, 1997, C. W. Carter, Jr. & R. M. Sweet, Eds., Academic Press (New York)) (incorporated by reference). The structure of the chimeric antibody complexed with GDF-8 was solved by molecular replacement using the program AMORE (Navaza, J. (2001). Implementation of molecular replacement in AMoRe. Acta Crystallogr., Sect. D: Biol. Crystallogr. 57, 1367-1372) (incorporated by reference). The probe used in the molecular replacement search was PDB entry 1 HZH. Prior to refinement, 5% of the data was randomly selected and designated as an $R_{free}$ test set to monitor the progress of the refinement. The structures of each complex was then rebuilt within Coot utilizing a series of omit maps (Emsley, P. & Cowtan, K. (2004) Coot: model-building tools for molecular graphics. Acta Crystallogr., Sect. D: Biol. Crystallogr. 60, 2126-2132) (incorporated by reference). Statistics from the refinement are listed in Table 8. The structure of humanized OGD1.0.0 complexed with GDF-8 was solved similarly, except that the probe used was the structure of the chimeric antibody.

TABLE 8

Refinement statistics for antibody: GDF-8 co-crystal structure

| Model Refinement | Chimeric Antibody-GDF-8 Complex | Humanized Antibody-GDF-8 Complex |
|---|---|---|
| Maximum resolution (Å) | 1.76 | 2.70 |
| $R_{work}$ (%) | 17.9 | 21.4 |
| $R_{free}$ (%) | 20.6 | 30.4 |
| Mean B value (Å$^2$) | 27.4 | 25.7 |
| Rms deviations from ideal geometry | | |
| Bonds (Å) | 0.010 | 0.009 |
| Angles (°) | 1.08 | 1.32 |
| Water molecules | 1047 | 0 |
| Ions | 5 Glycerol | 0 |

Residues in the antibodies and GDF-8 inferred to contact each other based on the co-crystal structure are listed in Table 9 in which antibody residues from the VH chain are preceded with an "H" and are numbered in relation to SEQ ID NO:3. Residues from the VL chain are preceded by an "L" and are numbered in relation to SEQ ID NO:5. Numbers from mature human GDF-8 are numbered in relation to SEQ ID NO:1. Residues were defined to be in contact with each other if they contained at least one pair of contacting atoms. Atoms were defined as contacting if they had a contact ratio C<1.3, where C=$D_{12}$÷($R_1$+$R_2$), $D_{12}$ is the distance between the atoms, $R_1$ is the vdW radius of atom 1 and $R_2$ is the vdW radius of atom 2. In practice, the average distance between contact atoms was about 4.7 Å, although the actual distance in any particular case varied according to the types of atoms in question.

TABLE 9

Residue contacts between antibodies and GDF-8 observed in co-crystal structure

| Antibody Residues | GDF-8 Residues |
|---|---|
| H30(SER) | 25(GLU) |
| H31(SER) | 25(GLU), 36(LYS) |
| H32(TYR) | 36(LYS) |
| H33(ALA) | 33(ILE) |
| H47(TRP) | 93(ILE) |
| H50(THR) | 33(ILE), 87(PHE), 93(ILE) |
| H51(ILE) | 87(PHE) |
| H52(SER) | 29(TRP), 30(ASP), 87(PHE) |
| H52A(SER) | 25(GLU), 29(TRP), 30(ASP) |
| H53(GLY) | 30(ASP) |
| H54(GLY) | 30(ASP) |
| H55(SER) | 30(ASP) |
| H56(TYR) | 30(ASP), 31(TRP) |
| H56(TYR) | 87(PHE) |
| H57(THR) | 87(PHE), 90(LYS), 91(GLU) |
| H58(SER) | 87(PHE), 91(GLU), 92(GLN), 93(ILE) |
| H64(LYS) | 91(GLU) |
| H95(GLN) | 33(ILE), 85(LEU) |
| H96(ASP) | 33(ILE), 34(ALA), 36(LYS), 85(LEU) |
| H97(TYR) | 33(ILE), 35(PRO), 83(ASN), 84(MET), 85(LEU), 95(TYR) |
| L30(SER) | 95(TYR) |
| L31(THR) | 83(ASN), 95(TYR) |
| L32(ALA) | 95(TYR) |
| L50(SER) | 95(TYR) |

TABLE 9-continued

Residue contacts between antibodies and GDF-8 observed in co-crystal structure

| Antibody Residues | GDF-8 Residues |
|---|---|
| L91(HIS) | 85(LEU), 95(TYR) |
| L92(TYR) | 93(ILE), 94(ILE), 95(TYR) |
| L93(SER) | 93(ILE), 94(ILE) |
| L94(THR) | 91(GLU), 92(GLN), 93(ILE) |
| L96(TRP) | 33(ILE), 85(LEU), 93(ILE) |

Example 11

Further Humanization of Antibody VH and VL Regions

Based on sequence analysis and the structure of anti-GDF-8 antibodies co-crystallized with GDF-8, antibody VH and VL regions were modified in an effort to further humanize their sequences. A sequence alignment of further humanized VH regions is shown in FIG. 1A. A sequence alignment of further humanized VL regions is shown in FIG. 1B. After expression constructs containing the new VH and VL regions were created antibodies were produced in transiently transfected COS-1 cells and purified using standard techniques. Binding affinity for GDF-8 and neutralizing activity of the antibodies was then tested as described herein. Results are reported in Table 10.

The CDR2 amino acid sequence from the humanized VH0 and VL0 regions (which originated from the murine antibody) were compared to the CDR2 sequence from the human germline VH region DP-47 and VL region DPK-9, respectively. All residues in the VH0 and VL0 CDR2 sequences differing from the human sequence were changed to human. The new VH and VL regions were designated VH2 (SEQ ID NO:66) and VL2 (SEQ ID NO:67), respectively. Intact antibodies produced using VH2 and VL0 regions and VH0 and VL2 regions were tested for binding to GDF-8 in a competition ELISA experiment. The results showed that completely humanizing VH CDR2 substantially reduced GDF-8 binding, whereas completely humanizing the VL CDR2 did not result in loss of antigen binding.

Further humanization of VH and VL regions was based on the co-crystal structure. Here, mouse-derived residues in the CDRs of the VH and VL regions were retained only if observed to contact GDF-8 residues in the co-crystal structure. Otherwise, all VH and VL CDR residues were changed to the corresponding human residues in DP-47 and DPK9, respectively, to generate VH3 (SEQ ID NO:68) and VL3 (SEQ ID NO:69). In a competition ELISA experiment an antibody comprising VH3 and VL0 (i.e., OGD1.3.0) showed significant loss in activity, while an antibody comprising VH0 and VL3, (i.e., OGD1.0.3) appeared to retain full activity.

Based on the sequence of CDR2 in VL2, position 50 of VL3 was substituted with alanine (i.e., S50A) to create VL4 (SEQ ID NO:71). An antibody comprising VH0 and VL4 (i.e., OGD1.0.4) prepared using this VL region retained substantial activity. A different mutation, W96L, was introduced into CDR3 of VL3 to create VL5 (SEQ ID NO:73). An antibody comprising VH0 and VL5 (i.e., OGD1.0.5) prepared using this VL region, however, demonstrated reduced activity compared to OGD1.0.0.

New mutations were introduced into the heavy variable region as well. Two substitutions were introduced into CDR3, i.e., M99F and N101 D, to form VH4 (SEQ ID NO:70). An antibody comprising VH4 and VL0 (i.e., OGD1.4.0) prepared using this VH region had substantially reduced activity which correlated with reduced binding affinity for GDF-8. In CDR2, a G53S substitution was made to create VH5 (SEQ ID NO:72). An antibody comprising VH5 and VL0 (i.e., OGD1.5.0) prepared using this VH region retained substantial activity.

TABLE 10

Expression and activity of further humanized antibody VH and VL regions

| Antibody version | Expression compared to OGD1.0.0 | Peak of interest (POI) after protein A | $IC_{50}$ by ELISA compared to OGD1.0.0 | Binding affinity ($K_D$) by SPR for GDF-8 | $IC_{50}$ by reporter gene assay compared to OGD1.0.0 |
|---|---|---|---|---|---|
| OGD1.0.0 | 1 X | >99% | 1 X | 2.59 pM | 1 X |
| OGD1.0.2 | 0.9 X, 1.2 X | 98.60% | 0.91 X | 1.46 pM | 1.03 X |
| OGD1.0.3 | 0.8 X | 98.60% | 0.96 X | 3.17 pM | 0.85 X |
| OGD1.0.4 | 1.3 X | >99% | 0.61 X | 2.46 pM | 1.54 X |
| OGD1.0.5 | 1.4 X | >99% | 5.94 X | 57 pM | not active |
| OGD1.2.0 | 0.5 X | N/A | N/A | N/A | N/A |
| OGD1.3.0 | 0.5 X | N/A | N/A | N/A | N/A |
| OGD1.4.0 | 0.4 X | >99% | 1.71 X | 284 pM | 7.5 X |
| OGD1.5.0 | 0.4 X | >99% | 0.88 X | 9.24 pM | 1.3 X |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of increasing the mass or strength of a muscle of a mammal, comprising administering to a mammal a therapeutically effective amount of an antibody or antigen binding fragment thereof that specifically binds GDF-8, said antibody or fragment comprising:
- an antibody variable heavy (VH) region comprising first, second and third complementarity determining regions (CDR), wherein VH CDR1 comprises SEQ ID NO:10 or SEQ ID NO:20, VH CDR2 comprises SEQ ID NO:11 or SEQ ID NO:21, and VH CDR3 comprises SEQ ID NO:12; and
- an antibody variable light (VL) region comprising first, second and third complementarity determining regions (CDR), wherein VL CDR1 comprises SEQ ID NO:13, VL CDR2 comprises SEQ ID NO:14, and VL CDR3 comprises SEQ ID NO:15;
- wherein said VH region comprises leucine at the amino acid position corresponding to residue number 111 of SEQ ID NO:44 (Kabat position 108).

2. The method of claim 1, wherein the fourth framework region (FR4) of said VH region comprises amino acids 106-116 of SEQ ID NO:44.

3. The method of claim 1, wherein said VL region comprises glycine at the amino acid position corresponding to residue number 100 of SEQ ID NO:46 (Kabat position 100).

4. The method of claim 1, wherein said VL region comprises glutamine at the amino acid position corresponding to residue number 100 of SEQ ID NO:46 (Kabat position 100).

5. The method of claim 4, wherein the fourth framework region of said VL region comprises amino acids 98-107 of SEQ ID NO:46.

6. The method of claim 5, wherein the fourth framework region of said VL region comprises amino acids 98-107 of SEQ ID NO:9.

7. The method of claim 1, wherein the VH region comprises the amino acid sequence of SEQ ID NO:44.

8. The method of claim 7, wherein the VL region comprises the amino acid sequence of SEQ ID NO:46.

9. The method of claim 7, wherein the VL region comprises the amino acid sequence of SEQ ID NO:9.

10. The method of claim 1, wherein the antibody further comprises an antibody constant heavy (CH) region derived from an antibody subtype selected from the group consisting of IgA, IgG, IgD, IgE, or IgM.

11. The method of claim 1, wherein the IgG subtype is IgG1.

12. The method of claim 1, wherein said IgG subtype comprises at least one mutation that alters Fc domain function.

13. The method of claim 1, wherein the muscle is skeletal muscle.

14. The method of claim 13, wherein the skeletal muscle is active in breathing.

15. A method of treating a muscular disorder in a mammal characterized by diminished muscle mass or strength, comprising administering to a mammal in need of treatment for a muscular disorder characterized by diminished muscle mass or strength a therapeutically effective amount of an antibody or antigen binding fragment thereof that specifically binds GDF-8, said antibody or fragment comprising:
- an antibody variable heavy (VH) region comprising the first, second and third complementarity determining regions (CDR) from the VH region defined by the amino acid sequence of SEQ ID NO:44; and
- an antibody variable light (VL) region comprising the first, second and third complementarity determining regions (CDR) from the VL region defined by the amino acid sequence of SEQ ID NO:46;

wherein said VH region comprises leucine at the amino acid position corresponding to residue number 111 of SEQ ID NO:44 (Kabat position 108).

16. The method of claim 15, wherein the muscular disorder is selected from the group consisting of muscular dystrophy, muscle atrophy, sarcopenia, cachexia, muscle wasting syndrome, age-related loss of muscle mass or strength, and frailty.

17. The method of claim 15, wherein the muscular disorder is muscular dystrophy.

18. The method of claim 17, wherein the muscular dystrophy is Duchenne muscular dystrophy.

19. The method of claim 15, wherein treatment is effective to increase the subject's performance in a 6 minute walk test.

20. The method of claim 15, wherein said antibody is administered to a subject also being treated with a glucocorticoid.

* * * * *

SEQUENCE LISTING

<160> NUMBER OF SEQ ID NOS: 73

<210> SEQ ID NO 1
<211> LENGTH: 109
<212> TYPE: PRT
<213> ORGANISM: Homo sapiens

<400> SEQUENCE: 1

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105
```

<210> SEQ ID NO 2
<211> LENGTH: 348
<212> TYPE: DNA
<213> ORGANISM: Mus musculus

<400> SEQUENCE: 2

```
gaagtgcagc tggtggagtc tgggggaggc ttagtgaagc ctggagggtc cctgaaactc      60
tcctgtgcag cctctggatt cactttcagt agctatgcca tgtcttgggt tcgccagact     120
ccggagaaga ggctggagtg ggtcgcaacc attagtagtg gtggtagtta cacctcctat     180
ccagacagtg tgaagggtcg attcaccatc tccagagaca atgccaagaa caccctgtac     240
ctgcaaatga gcagtctgag gtctgaggac acggccatgt attactgtgc aagacaagac     300
tatgctatga actactgggg tcaaggaacc tcagtcaccg tctcctca                  348
```

<210> SEQ ID NO 3
<211> LENGTH: 116
<212> TYPE: PRT
<213> ORGANISM: Mus musculus

<400> SEQUENCE: 3

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser Tyr Thr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Asp Tyr Ala Met Asn Tyr Trp Gly Gln Gly Thr Ser Val
            100                 105                 110

Thr Val Ser Ser
        115

<210> SEQ ID NO 4
<211> LENGTH: 321
<212> TYPE: DNA
<213> ORGANISM: Mus musculus

<400> SEQUENCE: 4
gacattgaga tgacccagtc tcacaaattc atgtccacat cagtaggaga cagggtcagc       60
atcacctgca aggccagtca ggatgtgagt actgctgtag cctggtatca acagaaacca      120
ggacaatctc ctaaactact gctttactcg gcatcctacc ggtacactgg agtccctgat      180
cggttcactg gcagtggatc tgggacggat ttcacttca ccatcagcag tgtgcaggct       240
gaagacctgg cagtttatta ctgtcagcaa cattatagta ctccgtggac gttcggtgga      300
ggcaccaagc tggaaatcaa a                                                321

<210> SEQ ID NO 5
<211> LENGTH: 107
<212> TYPE: PRT
<213> ORGANISM: Mus musculus

<400> SEQUENCE: 5

Asp Ile Glu Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Leu
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

```
Thr Phe Gly Gly Gly Thr Lys Leu Glu Ile Lys
            100                 105
```

<210> SEQ ID NO 6
<211> LENGTH: 348
<212> TYPE: DNA
<213> ORGANISM: Artificial Sequence
<220> FEATURE:
<223> OTHER INFORMATION: Mouse CDRs and human VH & J segment

<400> SEQUENCE: 6

```
gaggtccaac tattagaatc gggaggcggt ctggttcagc caggagggag tctcaggctt     60
agttgcgctg cgtcgggatt cacctttca agttacgcaa tgtcatgggt cgtcaggca     120
ccggggaaag cttagagtg gtgtcaact attagctctg gcggtagcta tacgtcgtat     180
cctgactctg tgaagggacg atttacaata agccgggaca attctaaaaa cactttgtac   240
ctacagatga attccttgag agccgaagat accgccgtct actattgtgc gaagcaagat   300
tacgctatga actattgggg tcaagggaca atggtaacgg tatcctcc                348
```

<210> SEQ ID NO 7
<211> LENGTH: 116
<212> TYPE: PRT
<213> ORGANISM: Artificial Sequence
<220> FEATURE:
<223> OTHER INFORMATION: Mouse CDRs and human VH & J segment

<400> SEQUENCE: 7

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Met Val
            100                 105                 110

Thr Val Ser Ser
        115
```

<210> SEQ ID NO 8
<211> LENGTH: 321
<212> TYPE: DNA
<213> ORGANISM: Artificial Sequence
<220> FEATURE:
<223> OTHER INFORMATION: Mouse CDRs and human VH & J segment

<400> SEQUENCE: 8

```
gacattcaaa tgacccaaag cccttcttcc ttaagcgcat cagtaggtga ccgagttaca    60
ataacgtgta aagcgagcca agatgtgagt actgcagtag cgtggtatca gcaaagcca    120
gggaaggctc cgaaactatt gatttactcc gcctcttaca gatatacggg cgttcctgat   180
aggtttagtg gaagtgggtc gggtacggac tttaccctga ctatatcgtc acttcagcca   240
gaggattttg ctacctacta ttgccaacag cattattcaa caccgtggac attcggccag   300
```

```
ggaactaagg tcgaaataaa a                                              321
```

<210> SEQ ID NO 9
<211> LENGTH: 107
<212> TYPE: PRT
<213> ORGANISM: Artificial Sequence
<220> FEATURE:
<223> OTHER INFORMATION: Mouse CDRs and human VH & J segment

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 10
<211> LENGTH: 5
<212> TYPE: PRT
<213> ORGANISM: Mus musculus

<400> SEQUENCE: 10

```
Ser Tyr Ala Met Ser
1               5
```

<210> SEQ ID NO 11
<211> LENGTH: 17
<212> TYPE: PRT
<213> ORGANISM: Mus musculus

<400> SEQUENCE: 11

```
Thr Ile Ser Ser Gly Gly Ser Tyr Thr Ser Tyr Pro Asp Ser Val Lys
1               5                   10                  15

Gly
```

<210> SEQ ID NO 12
<211> LENGTH: 7
<212> TYPE: PRT
<213> ORGANISM: Mus musculus

<400> SEQUENCE: 12

```
Gln Asp Tyr Ala Met Asn Tyr
1               5
```

<210> SEQ ID NO 13
<211> LENGTH: 11
<212> TYPE: PRT
<213> ORGANISM: Mus musculus

<400> SEQUENCE: 13

```
Lys Ala Ser Gln Asp Val Ser Thr Ala Val Ala
1               5                   10
```

<210> SEQ ID NO 14
<211> LENGTH: 7
<212> TYPE: PRT
<213> ORGANISM: Mus musculus

<400> SEQUENCE: 14

Ser Ala Ser Tyr Arg Tyr Thr
1               5

<210> SEQ ID NO 15
<211> LENGTH: 9
<212> TYPE: PRT
<213> ORGANISM: Mus musculus

<400> SEQUENCE: 15

Gln Gln His Tyr Ser Thr Pro Trp Thr
1               5

<210> SEQ ID NO 16
<211> LENGTH: 321
<212> TYPE: DNA
<213> ORGANISM: Homo sapiens

<400> SEQUENCE: 16
cgaaccgtag cggcaccgtc agtattcata ttccctccat cggacgagca attgaaaagt      60
gggacagctt cggtcgtgtg tctcttgaat aacttttacc ccagagaagc taaggtccag     120
tggaaagttg acaatgcgtt acagagcgga aattctcaag aatccgttac tgaacaggat     180
agtaaggatt ctacgtattc acttagcagt actctgaccc tatcaaaggc agattatgaa     240
aaacacaagg tatacgcctg cgaggtgacg catcaaggct tatccagccc agttacaaaa     300
tcttttaaca ggggtgagtg t                                                321

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 990
<212> TYPE: DNA
<213> ORGANISM: Artificial Sequence
<220> FEATURE:
<223> OTHER INFORMATION: Human sequence with substitution mutations

<400> SEQUENCE: 18

```
gcctccacaa aaggaccatc tgttttcccc ttggcgccat caagtaaatc tacttccgga    60
ggtaccgctg cgcttggctg cctcgtgaaa gactatttcc cagaacctgt cacagtctcg   120
tggaatagtg gtgctttaac ctcgggcgta catactttc ctgctgtact tcaatcaagc    180
ggactgtact cattatcgtc tgtagtcacg gtcccgagtt cttcactcgg aacacagact   240
tatatatgca acgttaatca taagcctagc aacaccaagg ttgacaaaaa ggtggaacca   300
aaatcgtgcg ataagacgca cacatgtcca ccctgtcctg caccagaagc tctgggcgcg   360
ccatcggttt tcttgttccc acccaaacct aaggacacgt taatgataag tcgaacgcca   420
gaggtgacat gtgttgtagt ggatgtgagc cacgaagatc cggaagtaaa attcaattgg   480
tatgtagatg gtgttgaagt ccataacgca aaaactaagc cgagggaaga gcagtacaac   540
tctacttata gggtagtctc cgtactaact gtcttgcacc aagattggct aaatgggaag   600
gaatataaat gtaaggtttc aaataaggca ctaccagccc cgatagagaa gacaataagc   660
aaagcgaagg ggcaaccaag agagccccaa gtgtacacct tgcctccgag cagagaggaa   720
atgacaaaaa atcaagtatc ccttacgtgt ctggtaaagg gattttatcc aagtgacata   780
gcagtggagt gggagagtaa cggccagcca gaaaacaatt acaaaaccac tcccccggtt   840
ttagatagcg atgggagttt cttttttgtac tcaaagttga ccgttgacaa gtcacgatgg   900
cagcaaggta atgtatttag ttgttctgtt atgcatgagg ccttacataa tcactacacg   960
cagaaatctc tctccttaag ccccgggaaa                                    990
```

<210> SEQ ID NO 19
<211> LENGTH: 330
<212> TYPE: PRT
<213> ORGANISM: Artificial Sequence
<220> FEATURE:
<223> OTHER INFORMATION: Human CH region with substitution mutations

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 20
<211> LENGTH: 10
<212> TYPE: PRT
<213> ORGANISM: Mus musculus

<400> SEQUENCE: 20

Gly Phe Thr Phe Ser Ser Tyr Ala Met Ser
1               5                   10

<210> SEQ ID NO 21
<211> LENGTH: 10
<212> TYPE: PRT
<213> ORGANISM: Mus musculus

<400> SEQUENCE: 21

Thr Ile Ser Ser Gly Gly Ser Tyr Thr Ser
1               5                   10

<210> SEQ ID NO 22
<211> LENGTH: 7
<212> TYPE: PRT
<213> ORGANISM: Mus musculus

<400> SEQUENCE: 22

Gln Asp Tyr Ala Met Asn Tyr
1               5

<210> SEQ ID NO 23
<211> LENGTH: 11
<212> TYPE: PRT
<213> ORGANISM: Mus musculus

<400> SEQUENCE: 23

Lys Ala Ser Gln Asp Val Ser Thr Ala Val Ala
1               5                   10

<210> SEQ ID NO 24
<211> LENGTH: 7
<212> TYPE: PRT
<213> ORGANISM: Mus musculus
```

<400> SEQUENCE: 24

Ser Ala Ser Tyr Arg Tyr Thr
1               5

<210> SEQ ID NO 25
<211> LENGTH: 9
<212> TYPE: PRT
<213> ORGANISM: Mus musculus

<400> SEQUENCE: 25

Gln Gln His Tyr Ser Thr Pro Trp Thr
1               5

<210> SEQ ID NO 26
<211> LENGTH: 116
<212> TYPE: PRT
<213> ORGANISM: Artificial Sequence
<220> FEATURE:
<223> OTHER INFORMATION: Human VH, murine CDRs

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Glu Lys Arg Leu Glu Trp Val
        35                  40                  45

Ala Thr Ile Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Gln Asp Tyr Ala Met Asn Tyr Trp Gly Gln Gly Thr Met Val
            100                 105                 110

Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Human VL, murine CDRs

<400> SEQUENCE: 27

Asp Ile Glu Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln His Tyr Ser Thr Pro Trp
                85                  90                  95

```
Thr Phe Gly Gln Gly Thr Lys Val Glu Ile Lys
            100                 105
```

<210> SEQ ID NO 28
<211> LENGTH: 405
<212> TYPE: DNA
<213> ORGANISM: Mus musculus

<400> SEQUENCE: 28

```
atgaactttg tgctcagctt gattttcctt gccctcattt taaaaggtgt ccagtgtgaa      60
gtgcagctgg tggagtctgg gggaggctta gtgaagcctg agggtccct gaaactctcc      120
tgtgcagcct ctggattcac tttcagtagc tatgccatgt cttgggttcg ccagactccg     180
gagaagaggc tggagtgggt cgcaaccatt agtagtggtg gtagttacac ctcctatcca     240
gacagtgtga agggtcgatt caccatctcc agagacaatg ccaagaacac cctgtacctg     300
caaatgagca gtctgaggtc tgaggacacg gccatgtatt actgtgcaag acaagactat     360
gctatgaact actggggtca aggaacctca gtcaccgtct cctca                     405
```

<210> SEQ ID NO 29
<211> LENGTH: 135
<212> TYPE: PRT
<213> ORGANISM: Mus musculus

<400> SEQUENCE: 29

```
Met Asn Phe Val Leu Ser Leu Ile Phe Leu Ala Leu Ile Leu Lys Gly
1               5                  10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Thr Ile Ser Ser Gly Gly Ser Tyr Thr Ser Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Arg Ser Glu Asp Thr Ala Met
            100                 105                 110

Tyr Tyr Cys Ala Arg Gln Asp Tyr Ala Met Asn Tyr Trp Gly Gln Gly
        115                 120                 125

Thr Ser Val Thr Val Ser Ser
    130                 135
```

<210> SEQ ID NO 30
<211> LENGTH: 381
<212> TYPE: DNA
<213> ORGANISM: Mus musculus

<400> SEQUENCE: 30

```
atggagtcac agattcaggt ctttgtattc gtgtttctct ggttgtctgg tgttgacgga      60
gacattgaga tgacccagtc tcacaaattc atgtccacat cagtaggaga cagggtcagc     120
atcacctgca aggccagtca ggatgtgagt actgctgtag cctggtatca acagaaacca     180
ggacaatctc ctaaactact gctttactcg gcatcctacc ggtacactgg agtccctgat     240
cggttcactg gcagtggatc tgggacggat ttcactttca ccatcagcag tgtgcaggct     300
gaagacctgg cagtttatta ctgtcagcaa cattatagta ctccgtggac gttcggtgga     360
```
ggcaccaagc tggaaatcaa a                                                    381

<210> SEQ ID NO 31
<211> LENGTH: 127
<212> TYPE: PRT
<213> ORGANISM: Mus musculus

<400> SEQUENCE: 31

Met Glu Ser Gln Ile Gln Val Phe Val Phe Val Phe Leu Trp Leu Ser
1               5                   10                  15

Gly Val Asp Gly Asp Ile Glu Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Leu Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Thr Pro Trp Thr Phe Gly Gly Gly Thr Lys Leu Glu Ile Lys
        115                 120                 125

<210> SEQ ID NO 32
<211> LENGTH: 95
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 33
<211> LENGTH: 98
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
                50                   55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys
```

<210> SEQ ID NO 34
<211> LENGTH: 15
<212> TYPE: PRT
<213> ORGANISM: Artificial Sequence
<220> FEATURE:
<223> OTHER INFORMATION: Synthetic protein sequence

<400> SEQUENCE: 34

```
Gly Gly Gly Gly Ser Gly Gly Gly Gly Ser Gly Gly Gly Gly Ser
 1               5                  10                  15
```

<210> SEQ ID NO 35
<211> LENGTH: 45
<212> TYPE: DNA
<213> ORGANISM: Homo sapiens

<400> SEQUENCE: 35
gcttttgata tctggggcca agggacaatg gtcaccgtct cttca                45

<210> SEQ ID NO 36
<211> LENGTH: 15
<212> TYPE: PRT
<213> ORGANISM: Homo sapiens

<400> SEQUENCE: 36

```
Ala Phe Asp Ile Trp Gly Gln Gly Thr Met Val Thr Val Ser Ser
 1               5                  10                  15
```

<210> SEQ ID NO 37
<211> LENGTH: 46
<212> TYPE: DNA
<213> ORGANISM: Homo sapiens

<400> SEQUENCE: 37
tactttgact actggggcca aggaaccctg gtcaccgtct cctcag              46

<210> SEQ ID NO 38
<211> LENGTH: 15
<212> TYPE: PRT
<213> ORGANISM: Homo sapiens

<400> SEQUENCE: 38

```
Tyr Phe Asp Tyr Trp Gly Gln Gly Thr Leu Val Thr Val Ser Ser
 1               5                  10                  15
```

<210> SEQ ID NO 39
<211> LENGTH: 37
<212> TYPE: DNA
<213> ORGANISM: Homo sapiens

<400> SEQUENCE: 39
tggacgttcg gccaagggac caaggtggaa atcaaac                        37

<210> SEQ ID NO 40
<211> LENGTH: 12
<212> TYPE: PRT

<213> ORGANISM: Homo sapiens

<400> SEQUENCE: 40

Trp Thr Phe Gly Gln Gly Thr Lys Val Glu Ile Lys
1               5                   10

<210> SEQ ID NO 41
<211> LENGTH: 37
<212> TYPE: DNA
<213> ORGANISM: Homo sapiens

<400> SEQUENCE: 41
ctcactttcg gcggagggac caaggtggag atcaaac                         37

<210> SEQ ID NO 42
<211> LENGTH: 12
<212> TYPE: PRT
<213> ORGANISM: Homo sapiens

<400> SEQUENCE: 42

Leu Thr Phe Gly Gly Gly Thr Lys Val Glu Ile Lys
1               5                   10

<210> SEQ ID NO 43
<211> LENGTH: 348
<212> TYPE: DNA
<213> ORGANISM: Artificial Sequence
<220> FEATURE:
<223> OTHER INFORMATION: Human VH, murine CDRs

<400> SEQUENCE: 43
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcaacc attagtagtg gtggtagtta cacctcctat   180
ccagacagtg tgaagggtcg gttcaccatc tccagagaca attccaagaa cacgctgtat   240
ctgcaaatga acagcctgag agccgaggac acggccgtat attactgtgc gaaacaagac   300
tatgctatga actactgggg ccagggcacc ctggtcaccg tgtcctcc              348

<210> SEQ ID NO 44
<211> LENGTH: 116
<212> TYPE: PRT
<213> ORGANISM: Artificial Sequence
<220> FEATURE:
<223> OTHER INFORMATION: Mouse CDRs and human VH & J segment

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Leu Val

Thr Val Ser Ser
        115

<210> SEQ ID NO 45
<211> LENGTH: 321
<212> TYPE: DNA
<213> ORGANISM: Artificial Sequence
<220> FEATURE:
<223> OTHER INFORMATION: Human VL, murine CDRs

<400> SEQUENCE: 45

```
gacatccaga tgacccagtc ccctcctcc ctgtccgcct ccgtgggcga cagagtgacc      60
atcacctgca aggccagtca ggatgtgagt actgctgtgg cctggtatca gcagaagcct    120
ggcaaggccc ctaagctgct gatctactcc gcatcctacc ggtacactgg cgtgccttcc    180
cggttctccg gctccggctc tggcaccgac ttcaccctga ccatctcctc cctgcagcct    240
gaggacttcg ccacctacta ctgccagcaa cattatagta ctccatggac ctttggcggt    300
ggaacaaagg tggaaatcaa a                                              321
```

<210> SEQ ID NO 46
<211> LENGTH: 107
<212> TYPE: PRT
<213> ORGANISM: Artificial Sequence
<220> FEATURE:
<223> OTHER INFORMATION: Mouse CDRs and human VH & J segment

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 47
<211> LENGTH: 348
<212> TYPE: DNA
<213> ORGANISM: Artificial Sequence
<220> FEATURE:
<223> OTHER INFORMATION: Human VH, murine CDRs

<400> SEQUENCE: 47

```
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg gtctcaacc attagtagtg gtggtagtta cacctcctat    180
ccagacagtg tgaagggtcg gttcaccatc tccagagaca attccaagaa cacgctgtat    240
ctgcaaatga acagcctgag agccgaggac acggccgtat attactgtgc gaaacaagac    300
tatgctatga actactgggg ccagggcacc atggtcaccg tgtcctcc                 348
```

<210> SEQ ID NO 48
<211> LENGTH: 321
<212> TYPE: DNA
<213> ORGANISM: Artificial Sequence
<220> FEATURE:
<223> OTHER INFORMATION: Human VL, murine CDRs

<400> SEQUENCE: 48

```
gacatccaga tgacccagtc ccctcctcc ctgtccgcct ccgtgggcga cagagtgacc      60
atcacctgca aggccagtca ggatgtgagt actgctgtgg cctggtatca gcagaagcct     120
ggcaaggccc ctaagctgct gatctactcc gcatcctacc ggtacactgg cgtgccttcc    180
cggttctccg gctccggctc tggcaccgac ttcaccctga ccatctcctc cctgcagcct    240
gaggacttcg ccacctacta ctgccagcaa cattatagta ctccatggac ctttggccaa    300
ggaacaaagg tggaaatcaa a                                              321
```

<210> SEQ ID NO 49
<211> LENGTH: 405
<212> TYPE: DNA
<213> ORGANISM: Artificial Sequence
<220> FEATURE:
<223> OTHER INFORMATION: Human VH, murine CDRs

<400> SEQUENCE: 49

```
atgggatgga gctgtatcat cctcttcttg gtagcaacag ctacaggcgc gcactccgag     60
gtgcagctgt tggagtctgg gggaggcttg gtacagcctg gggggtccct gagactctcc    120
tgtgcagcct ctggattcac ctttagcagc tatgccatga gctgggtccg ccaggctcca    180 gggaagggc tggagtgggt ctcaaccatt agtagtggtg gtagttacac ctcctatcca    240
gacagtgtga agggtcggtt caccatctcc agagacaatt ccaagaacac gctgtatctg    300
caaatgaaca gcctgagagc cgaggacacg gccgtatatt actgtgcgaa acaagactat    360
gctatgaact actggggcca gggcaccctg gtcaccgtgt cctcc                    405
```

<210> SEQ ID NO 50
<211> LENGTH: 135
<212> TYPE: PRT
<213> ORGANISM: Artificial Sequence
<220> FEATURE:
<223> OTHER INFORMATION: Human VH, murine CDRs

<400> SEQUENCE: 50

```
Met Gly Trp Ser Cys Ile Ile Leu Phe Leu Val Ala Thr Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Thr Ile Ser Ser Gly Gly Ser Tyr Thr Ser Tyr Pro
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gln Asp Tyr Ala Met Asn Tyr Trp Gly Gln Gly
```

Thr Leu Val Thr Val Ser Ser
        130             135

<210> SEQ ID NO 51
<211> LENGTH: 378
<212> TYPE: DNA
<213> ORGANISM: Artificial Sequence
<220> FEATURE:
<223> OTHER INFORMATION: Human VL, murine CDRs

<400> SEQUENCE: 51
atgggatgga gctgtatcat cctcttcttg gtagcaacag ctacaggcgc gcactccgac     60
atccagatga cccagtcccc ctcctccctg tccgcctccg tgggcgacag agtgaccatc    120
acctgcaagg ccagtcagga tgtgagtact gctgtggcct ggtatcagca gaagcctggc    180
aaggccccta agctgctgat ctactccgca tcctaccggt acactggcgt gccttcccgg    240
ttctccggct ccggctctgg caccgacttc accctgacca tctcctccct gcagcctgag    300
gacttcgcca cctactactg ccagcaacat tatagtactc catggacctt tggcggtgga    360
acaaaggtgg aaatcaaa                                                  378

<210> SEQ ID NO 52
<211> LENGTH: 126
<212> TYPE: PRT
<213> ORGANISM: Artificial Sequence
<220> FEATURE:
<223> OTHER INFORMATION: Human VL, murine CDRs

<400> SEQUENCE: 52

Met Gly Trp Ser Cys Ile Ile Leu Phe Leu Val Ala Thr Ala Thr Gly
1               5                   10                  15

Ala His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asp Val
        35                  40                  45

Ser Thr Ala Val Ala Trp Tyr Gln Gln Lys Pro Gly Lys Ala Pro Lys
    50                  55                  60

Leu Leu Ile Tyr Ser Ala Ser Tyr Arg Tyr Thr Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Ser
            100                 105                 110

Thr Pro Trp Thr Phe Gly Gly Gly Thr Lys Val Glu Ile Lys
        115                 120                 125

<210> SEQ ID NO 53
<211> LENGTH: 405
<212> TYPE: DNA
<213> ORGANISM: Artificial Sequence
<220> FEATURE:
<223> OTHER INFORMATION: Human VH, murine CDRs

<400> SEQUENCE: 53
atgggatgga gctgtatcat cctcttcttg gtagcaacag ctacaggcgc gcactccgag     60
gtgcagctgt tggagtctgg gggaggcttg gtacagcctg gggggtccct gagactctcc    120
tgtgcagcct ctggattcac ctttagcagc tatgccatga gctgggtccg ccaggctcca    180

```
gggaagggc tggagtgggt ctcaaccatt agtagtggtg gtagttacac ctcctatcca    240
gacagtgtga aggtcggtt caccatctcc agagacaatt ccaagaacac gctgtatctg    300
caaatgaaca gcctgagagc cgaggacacg gccgtatatt actgtgcgaa acaagactat    360
gctatgaact actggggcca gggcaccatg gtcaccgtgt cctcc                   405

<210> SEQ ID NO 54
<211> LENGTH: 135
<212> TYPE: PRT
<213> ORGANISM: Artificial Sequence
<220> FEATURE:
<223> OTHER INFORMATION: Human VH, murine CDRs

<400> SEQUENCE: 54

Met Gly Trp Ser Cys Ile Ile Leu Phe Leu Val Ala Thr Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Thr Ile Ser Ser Gly Gly Ser Tyr Thr Ser Tyr Pro
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gln Asp Tyr Ala Met Asn Tyr Trp Gly Gln Gly
        115                 120                 125

Thr Met Val Thr Val Ser Ser
    130                 135

<210> SEQ ID NO 55
<211> LENGTH: 378
<212> TYPE: DNA
<213> ORGANISM: Artificial Sequence
<220> FEATURE:
<223> OTHER INFORMATION: Human VL, murine CDRs

<400> SEQUENCE: 55
atgggatgga gctgtatcat cctcttcttg gtagcaacag ctacaggcgc gcactccgac     60
atccagatga cccagtcccc ctcctccctg tccgcctccg tgggcgacag agtgaccatc    120
acctgcaagg ccagtcagga tgtgagtact gctgtggcct ggtatcagca gaagcctggc    180
aaggccccta gctgctgat ctactccgca tcctaccggt acactggcgt gccttccgg     240 ttctccggct ccggctctgg caccgacttc accctgacca tctcctccct gcagcctgag    300
gacttcgcca ctactactg ccagcaacat tatagtactc catggacctt tggccaagga    360
acaaaggtgg aaatcaaa                                                  378

<210> SEQ ID NO 56
<211> LENGTH: 126
<212> TYPE: PRT
<213> ORGANISM: Artificial Sequence
<220> FEATURE:
<223> OTHER INFORMATION: Human VL, murine CDRs

<400> SEQUENCE: 56
```

```
Met Gly Trp Ser Cys Ile Ile Leu Phe Leu Val Ala Thr Ala Thr Gly
1               5                   10                  15

Ala His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asp Val
        35                  40                  45

Ser Thr Ala Val Ala Trp Tyr Gln Gln Lys Pro Gly Lys Ala Pro Lys
    50                  55                  60

Leu Leu Ile Tyr Ser Ala Ser Tyr Arg Tyr Thr Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Ser
                100                 105                 110

Thr Pro Trp Thr Phe Gly Gln Gly Thr Lys Val Glu Ile Lys
            115                 120                 125
```

<210> SEQ ID NO 57
<211> LENGTH: 330
<212> TYPE: PRT
<213> ORGANISM: Artificial Sequence
<220> FEATURE:
<223> OTHER INFORMATION: Human CH region with substitution mutations

<400> SEQUENCE: 57

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 58
<211> LENGTH: 446
<212> TYPE: PRT
<213> ORGANISM: Artificial Sequence
<220> FEATURE:
<223> OTHER INFORMATION: Mouse CDRs and human VH & J segment; Human
      CH region with substitution mutations

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Thr Ile Ser Ser Gly Gly Ser Tyr Thr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gln Asp Tyr Ala Met Asn Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 59
<211> LENGTH: 214
<212> TYPE: PRT
<213> ORGANISM: Artificial Sequence
<220> FEATURE:
<223> OTHER INFORMATION: Mouse CDRs and human VH, J segment and CH

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 1476
<212> TYPE: DNA
<213> ORGANISM: Artificial Sequence
<220> FEATURE:
<223> OTHER INFORMATION: scFv

<400> SEQUENCE: 60

```
atgggatgga gctgtatcat cctcttcttg gtagcaacag ctacaggcgc gcactccgac      60
attgagatga cccagtctca caaattcatg tccacatcag taggagacag ggtcagcatc     120
acctgcaagg ccagtcagga tgtgagtact gctgtagcct ggtatcaaca gaaaccagga     180
caatctccta aactactgct ttactcggca tcctaccgt acactggagt ccctgatcgg     240
ttcactggca gtggatctgg gacggatttc actttcacca tcagcagtgt gcaggctgaa     300
gacctggcag tttattactg tcagcaacat tatagtactc cgtggacgtt ggcggtgga     360
acaaaggtgg aaatcaaagg aggcggcggt tcaggcggag gtggctctgg cggtggcgga     420
agctccgaag tgcagctggt ggagtctggg ggaggcttag tgaagcctgg agggtccctg     480
aaactctcct gtgcagcctc tggattcact ttcagtagct atgccatgtc ttgggttcgc     540
cagactccgg agaagaggct ggagtgggtc gcaaccatta gtagtggtgg tagttacacc     600
tcctatccag acagtgtgaa gggtcgattc accatctcca gagacaatgc caagaacacc     660
ctgtacctgc aaatgagcag tctgaggtct gaggacacgg ccatgtatta ctgtgcaaga     720
caagactatg ctatgaacta ctggggccag ggcaccctgg tcaccgtgtc ctctgatcag     780
gagcccaaat cttctgacaa aactcacaca tgcccaccgt gcccagcacc tgaagccgct     840
ggggcaccgt cagtcttcct cttccccca aaacccaagg acaccctcat gatctcccgg     900
accctgaggt cacatgcgt ggtggtggac gtgagccacg aagaccctga ggtcaagttc     960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatcccgg    1200
gaggagatga ccaagaacca ggtcagcctg acctgcctgg tcaaaggctt ctatcccagc    1260
gacatcgccg tggagtggga gagcaatggg cagccggaga acaactacaa gaccacgcct    1320
cccgtgctgg actccgacgg ctccttcttc ctctatagca agctcaccgt ggacaagagc    1380
aggtggcagc aggggaacgt cttctcatgc tccgtgatgc atgaggctct gcacaaccac    1440
tacacgcaga gagcctctc cctgtccccg ggtaaa                               1476
```

<210> SEQ ID NO 61
<211> LENGTH: 492
<212> TYPE: PRT
<213> ORGANISM: Artificial Sequence
<220> FEATURE:
<223> OTHER INFORMATION: scFv

<400> SEQUENCE: 61

Met Gly Trp Ser Cys Ile Ile Leu Phe Leu Val Ala Thr Ala Thr Gly
1               5                   10                  15

```
Ala His Ser Asp Ile Glu Met Thr Gln Ser His Lys Phe Met Ser Thr
             20                  25                  30

Ser Val Gly Asp Arg Val Ser Ile Thr Cys Lys Ala Ser Gln Asp Val
         35                  40                  45

Ser Thr Ala Val Ala Trp Tyr Gln Gln Lys Pro Gly Gln Ser Pro Lys
 50                  55                  60

Leu Leu Leu Tyr Ser Ala Ser Tyr Arg Tyr Thr Gly Val Pro Asp Arg
 65                  70                  75                  80

Phe Thr Gly Ser Gly Ser Gly Thr Asp Phe Thr Phe Thr Ile Ser Ser
                 85                  90                  95

Val Gln Ala Glu Asp Leu Ala Val Tyr Tyr Cys Gln Gln His Tyr Ser
             100                 105                 110

Thr Pro Trp Thr Phe Gly Gly Gly Thr Lys Val Glu Ile Lys Gly Gly
         115                 120                 125

Gly Gly Ser Gly Gly Gly Gly Ser Gly Gly Gly Gly Ser Ser Glu Val
130                 135                 140

Gln Leu Val Glu Ser Gly Gly Gly Leu Val Lys Pro Gly Gly Ser Leu
145                 150                 155                 160

Lys Leu Ser Cys Ala Ala Ser Gly Phe Thr Phe Ser Ser Tyr Ala Met
                 165                 170                 175

Ser Trp Val Arg Gln Thr Pro Glu Lys Arg Leu Glu Trp Val Ala Thr
             180                 185                 190

Ile Ser Ser Gly Gly Ser Tyr Thr Ser Tyr Pro Asp Ser Val Lys Gly
         195                 200                 205

Arg Phe Thr Ile Ser Arg Asp Asn Ala Lys Asn Thr Leu Tyr Leu Gln
 210                 215                 220

Met Ser Ser Leu Arg Ser Glu Asp Thr Ala Met Tyr Tyr Cys Ala Arg
225                 230                 235                 240

Gln Asp Tyr Ala Met Asn Tyr Trp Gly Gln Gly Thr Leu Val Thr Val
                 245                 250                 255

Ser Ser Asp Gln Glu Pro Lys Ser Ser Asp Lys Thr His Thr Cys Pro
             260                 265                 270

Pro Cys Pro Ala Pro Glu Ala Ala Gly Ala Pro Ser Val Phe Leu Phe
         275                 280                 285

Pro Pro Lys Pro Lys Asp Thr Leu Met Ile Ser Arg Thr Pro Glu Val
 290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                 325                 330                 335

Arg Glu Glu Gln Tyr Asn Ser Thr Tyr Arg Val Val Ser Val Leu Thr
             340                 345                 350

Val Leu His Gln Asp Trp Leu Asn Gly Lys Glu Tyr Lys Cys Lys Val
         355                 360                 365

Ser Asn Lys Ala Leu Pro Ala Pro Ile Glu Lys Thr Ile Ser Lys Ala
 370                 375                 380

Lys Gly Gln Pro Arg Glu Pro Gln Val Tyr Thr Leu Pro Pro Ser Arg
385                 390                 395                 400

Glu Glu Met Thr Lys Asn Gln Val Ser Leu Thr Cys Leu Val Lys Gly
                 405                 410                 415

Phe Tyr Pro Ser Asp Ile Ala Val Glu Trp Glu Ser Asn Gly Gln Pro
             420                 425                 430
```

Glu Asn Asn Tyr Lys Thr Thr Pro Val Leu Asp Ser Asp Gly Ser
            435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490

<210> SEQ ID NO 62
<211> LENGTH: 1476
<212> TYPE: DNA
<213> ORGANISM: Artificial Sequence
<220> FEATURE:
<223> OTHER INFORMATION: scFv

<400> SEQUENCE: 62

| | | | | | |
|---|---|---|---|---|---|
| atgggatgga | gctgtatcat | cctcttcttg | gtagcaacag | ctacaggcgc | gcactccgag | 60 |
| gtgcagctgt | tggagtctgg | gggaggcttg | gtacagcctg | gggggtccct | gagactctcc | 120 |
| tgtgcagcct | ctggattcac | ctttagcagc | tatgccatga | gctgggtccg | ccaggctcca | 180 |
| gggaaggggc | tggagtgggt | ctcaaccatt | agtagtggtg | gtagttacac | ctcctatcca | 240 |
| gacagtgtga | aggtcggttc | accatctcc | agagacaatt | ccaagaacac | gctgtatctg | 300 |
| caaatgaaca | gcctgagagc | cgaggacacg | gccgtatatt | actgtgcgaa | caagactat | 360 |
| gctatgaact | actggggcca | gggcaccctg | gtcaccgtgt | cctctggagg | cggcggttca | 420 |
| ggcggaggtg | gctctggcgg | tggcggaagc | tccgacatcc | agatgaccca | gtccccctcc | 480 |
| tccctgtccg | cctccgtggg | cgacagagtg | accatcacct | gcaaggccag | tcaggatgtg | 540 |
| agtactgctg | tggcctggta | tcagcagaag | cctggcaagg | cccctaagct | gctgatctac | 600 |
| tccgcatcct | accggtacac | tggcgtgcct | tccggttct | ccggctccgg | ctctggcacc | 660 |
| gacttcaccc | tgaccatctc | ctccctgcag | cctgaggact | tcgccaccta | ctactgccag | 720 |
| caacattata | gtactccatg | gacctttggc | ggtggaacaa | aggtggaaat | caaagatcag | 780 |
| gagcccaaat | cttctgacaa | aactcacaca | tgcccaccgt | gcccagcacc | tgaagccgct | 840 |
| ggggcaccgt | cagtcttcct | cttccccca | aaacccaagg | acaccctcat | gatctcccgg | 900 |
| accctgaggc | tcatgcgt | ggtggtggac | gtgagccacg | aagaccctga | ggtcaagttc | 960 |
| aactggtacg | tggacggcgt | ggaggtgcat | aatgccaaga | caaagccgcg | ggaggagcag | 1020 |
| tacaacagca | cgtaccgtgt | ggtcagcgtc | ctcaccgtcc | tgcaccagga | ctggctgaat | 1080 |
| ggcaaggagt | acaagtgcaa | ggtctccaac | aaagccctcc | cagcccccat | cgagaaaacc | 1140 |
| atctccaaag | ccaaagggca | gccccgagaa | ccacaggtgt | acaccctgcc | cccatcccgg | 1200 |
| gaggagatga | ccaagaacca | ggtcagcctg | acctgcctgg | tcaaaggctt | ctatcccagc | 1260 |
| gacatcgccg | tggagtggga | gagcaatggg | cagccggaga | acaactacaa | gaccacgcct | 1320 |
| cccgtgctgg | actccgacgg | ctccttcttc | ctctatagca | agctcaccgt | ggacaagagc | 1380 |
| aggtggcagc | aggggaacgt | cttctcatgc | tccgtgatgc | atgaggctct | gcacaaccac | 1440 |
| tacacgcaga | agagcctctc | cctgtccccg | ggtaaa | | | 1476 |

<210> SEQ ID NO 63
<211> LENGTH: 492
<212> TYPE: PRT
<213> ORGANISM: Artificial Sequence
<220> FEATURE:
<223> OTHER INFORMATION: scFv

<400> SEQUENCE: 63

| | | | | | | | | | | | | | | |
|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 | |
| Ala | His | Ser | Glu | Val | Gln | Leu | Leu | Glu | Ser | Gly | Gly | Gly | Leu | Val | Gln |
| | | | 20 | | | | | 25 | | | | | 30 | | |
| Pro | Gly | Gly | Ser | Leu | Arg | Leu | Ser | Cys | Ala | Ala | Ser | Gly | Phe | Thr | Phe |
| | | 35 | | | | | 40 | | | | | 45 | | | |
| Ser | Ser | Tyr | Ala | Met | Ser | Trp | Val | Arg | Gln | Ala | Pro | Gly | Lys | Gly | Leu |
| | 50 | | | | | 55 | | | | | 60 | | | | |
| Glu | Trp | Val | Ser | Thr | Ile | Ser | Ser | Gly | Gly | Ser | Tyr | Thr | Ser | Tyr | Pro |
| 65 | | | | | 70 | | | | | 75 | | | | | 80 |
| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | |
| Thr | Leu | Tyr | Leu | Gln | Met | Asn | Ser | Leu | Arg | Ala | Glu | Asp | Thr | Ala | Val |
| | | | 100 | | | | | 105 | | | | | 110 | | |
| Tyr | Tyr | Cys | Ala | Lys | Gln | Asp | Tyr | Ala | Met | Asn | Tyr | Trp | Gly | Gln | Gly |
| | | 115 | | | | | 120 | | | | | 125 | | | |
| Thr | Leu | Val | Thr | Val | Ser | Ser | Gly | Gly | Gly | Ser | Gly | Gly | Gly | Gly |
| 130 | | | | | 135 | | | | | 140 | | | | | |
| Ser | Gly | Gly | Gly | Gly | Ser | Ser | Asp | Ile | Gln | Met | Thr | Gln | Ser | Pro | Ser |
| 145 | | | | | 150 | | | | | 155 | | | | | 160 |
| Ser | Leu | Ser | Ala | Ser | Val | Gly | Asp | Arg | Val | Thr | Ile | Thr | Cys | Lys | Ala |
| | | | | 165 | | | | | 170 | | | | | 175 | |
| Ser | Gln | Asp | Val | Ser | Thr | Ala | Val | Ala | Trp | Tyr | Gln | Gln | Lys | Pro | Gly |
| | | | 180 | | | | | 185 | | | | | 190 | | |
| Lys | Ala | Pro | Lys | Leu | Leu | Ile | Tyr | Ser | Ala | Ser | Tyr | Arg | Tyr | Thr | Gly |
| | | 195 | | | | | 200 | | | | | 205 | | | |
| Val | Pro | Ser | Arg | Phe | Ser | Gly | Ser | Gly | Ser | Gly | Thr | Asp | Phe | Thr | Leu |
| | 210 | | | | | 215 | | | | | 220 | | | | |
| Thr | Ile | Ser | Ser | Leu | Gln | Pro | Glu | Asp | Phe | Ala | Thr | Tyr | Tyr | Cys | Gln |
| 225 | | | | | 230 | | | | | 235 | | | | | 240 |
| Gln | His | Tyr | Ser | Thr | Pro | Trp | Thr | Phe | Gly | Gly | Gly | Thr | Lys | Val | Glu |
| | | | | 245 | | | | | 250 | | | | | 255 | |
| Ile | Lys | Asp | Gln | Glu | Pro | Lys | Ser | Ser | Asp | Lys | Thr | His | Thr | Cys | Pro |
| | | | 260 | | | | | 265 | | | | | 270 | | |
| Pro | Cys | Pro | Ala | Pro | Glu | Ala | Ala | Gly | Ala | Pro | Ser | Val | Phe | Leu | Phe |
| | | 275 | | | | | 280 | | | | | 285 | | | |
| Pro | Pro | Lys | Pro | Lys | Asp | Thr | Leu | Met | Ile | Ser | Arg | Thr | Pro | Glu | Val |
| | 290 | | | | | 295 | | | | | 300 | | | | |
| Thr | Cys | Val | Val | Val | Asp | Val | Ser | His | Glu | Asp | Pro | Glu | Val | Lys | Phe |
| 305 | | | | | 310 | | | | | 315 | | | | | 320 |
| Asn | Trp | Tyr | Val | Asp | Gly | Val | Glu | Val | His | Asn | Ala | Lys | Thr | Lys | Pro |
| | | | | 325 | | | | | 330 | | | | | 335 | |
| Arg | Glu | Glu | Gln | Tyr | Asn | Ser | Thr | Tyr | Arg | Val | Val | Ser | Val | Leu | Thr |
| | | | 340 | | | | | 345 | | | | | 350 | | |
| Val | Leu | His | Gln | Asp | Trp | Leu | Asn | Gly | Lys | Glu | Tyr | Lys | Cys | Lys | Val |
| | | 355 | | | | | 360 | | | | | 365 | | | |
| Ser | Asn | Lys | Ala | Leu | Pro | Ala | Pro | Ile | Glu | Lys | Thr | Ile | Ser | Lys | Ala |
| | 370 | | | | | 375 | | | | | 380 | | | | |
| Lys | Gly | Gln | Pro | Arg | Glu | Pro | Gln | Val | Tyr | Thr | Leu | Pro | Pro | Ser | Arg |
| 385 | | | | | 390 | | | | | 395 | | | | | 400 |
| Glu | Glu | Met | Thr | Lys | Asn | Gln | Val | Ser | Leu | Thr | Cys | Leu | Val | Lys | Gly |

```
                    405                 410                 415
Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 64
<211> LENGTH: 1476
<212> TYPE: DNA
<213> ORGANISM: Artificial Sequence
<220> FEATURE:
<223> OTHER INFORMATION: scFv

<400> SEQUENCE: 64

| | | | | | |
|---|---|---|---|---|---|
| atgggatgga | gctgtatcat | cctcttcttg | gtagcaacag | ctacaggcgc | gcactccgac | 60 |
| atccagatga | cccagtcccc | ctcctccctg | tccgcctccg | tgggcgacag | agtgaccatc | 120 |
| acctgcaagg | ccagtcagga | tgtgagtact | gctgtggcct | ggtatcagca | gaagcctggc | 180 |
| aaggccccta | agctgctgat | ctactccgca | tcctaccggt | acactggcgt | gccttcccgg | 240 |
| ttctccggct | ccggctctgg | caccgacttc | accctgacca | tctcctccct | gcagcctgag | 300 |
| gacttcgcca | cctactactg | ccagcaacat | tatagtactc | catggacctt | tggcggtgga | 360 |
| acaaaggtgg | aaatcaaagg | aggcggcggt | tcaggcggag | gtggctctgg | cggtggcgga | 420 |
| agctccgagg | tgcagctgtt | ggagtctggg | ggaggcttgg | tacagcctgg | ggggtccctg | 480 |
| agactctcct | gtgcagcctc | tggattcacc | tttagcagct | atgccatgag | ctgggtccgc | 540 |
| caggctccag | ggaagggggct | ggagtgggtc | tcaaccatta | gtagtggtgg | tagttacacc | 600 |
| tcctatccag | acagtgtgaa | gggtcggttc | accatctcca | gagacaattc | caagaacacg | 660 |
| ctgtatctgc | aaatgaacag | cctgagagcc | gaggacacgg | ccgtatatta | ctgtgcgaaa | 720 |
| caagactatg | ctatgaacta | ctggggccag | ggcaccctgg | tcaccgtgtc | ctctgatcag | 780 |
| gagcccaaat | cttctgacaa | aactcacaca | tgcccaccgt | gcccagcacc | tgaagccgct | 840 |
| ggggcaccgt | cagtcttcct | cttcccccca | aaacccaagg | acaccctcat | gatctcccgg | 900 |
| acccctgagg | tcacatgcgt | ggtggtggac | gtgagccacg | aagaccctga | ggtcaagttc | 960 |
| aactggtacg | tggacggcgt | ggaggtgcat | aatgccaaga | caaagccgcg | ggaggagcag | 1020 |
| tacaacagca | cgtaccgtgt | ggtcagcgtc | ctcaccgtcc | tgcaccagga | ctggctgaat | 1080 |
| ggcaaggagt | acaagtgcaa | ggtctccaac | aaagccctcc | cagcccccat | cgagaaaacc | 1140 |
| atctccaaag | ccaaagggca | gccccgagaa | ccacaggtgt | acaccctgcc | ccatcccgg | 1200 |
| gaggagatga | ccaagaacca | ggtcagcctg | acctgcctgg | tcaaaggctt | ctatcccagc | 1260 |
| gacatcgccg | tggagtggga | gagcaatggg | cagccggaga | acaactacaa | gaccacgcct | 1320 |
| cccgtgctgg | actccgacgg | ctccttcttc | ctctatagca | agctcaccgt | ggacaagagc | 1380 |
| aggtggcagc | aggggaacgt | cttctcatgc | tccgtgatgc | atgaggctct | gcacaaccac | 1440 |
| tacacgcaga | agagcctctc | cctgtccccg | ggtaaa | | | 1476 |

<210> SEQ ID NO 65

-continued

```
<211> LENGTH: 492
<212> TYPE: PRT
<213> ORGANISM: Artificial Sequence
<220> FEATURE:
<223> OTHER INFORMATION: scFv

<400> SEQUENCE: 65
```

| | | | | | | | | | | | | | | | |
|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 | |
| Ala | His | Ser | Asp | Ile | Gln | Met | Thr | Gln | Ser | Pro | Ser | Ser | Leu | Ser | Ala |
| | | | 20 | | | | | 25 | | | | | 30 | | |
| Ser | Val | Gly | Asp | Arg | Val | Thr | Ile | Thr | Cys | Lys | Ala | Ser | Gln | Asp | Val |
| | | | 35 | | | | | 40 | | | | | 45 | | |
| Ser | Thr | Ala | Val | Ala | Trp | Tyr | Gln | Gln | Lys | Pro | Gly | Lys | Ala | Pro | Lys |
| | 50 | | | | | 55 | | | | | 60 | | | | |
| Leu | Leu | Ile | Tyr | Ser | Ala | Ser | Tyr | Arg | Tyr | Thr | Gly | Val | Pro | Ser | Arg |
| 65 | | | | | 70 | | | | | 75 | | | | | 80 |
| Phe | Ser | Gly | Ser | Gly | Ser | Gly | Thr | Asp | Phe | Thr | Leu | Thr | Ile | Ser | Ser |
| | | | | 85 | | | | | 90 | | | | | 95 | |
| Leu | Gln | Pro | Glu | Asp | Phe | Ala | Thr | Tyr | Tyr | Cys | Gln | Gln | His | Tyr | Ser |
| | | | 100 | | | | | 105 | | | | | 110 | | |
| Thr | Pro | Trp | Thr | Phe | Gly | Gly | Gly | Thr | Lys | Val | Glu | Ile | Lys | Gly | Gly |
| | | | 115 | | | | | 120 | | | | | 125 | | |
| Gly | Gly | Ser | Gly | Gly | Gly | Gly | Ser | Gly | Gly | Gly | Gly | Ser | Ser | Glu | Val |
| | | | 130 | | | | | 135 | | | | | 140 | | |
| Gln | Leu | Leu | Glu | Ser | Gly | Gly | Gly | Leu | Val | Gln | Pro | Gly | Gly | Ser | Leu |
| 145 | | | | | 150 | | | | | 155 | | | | | 160 |
| Arg | Leu | Ser | Cys | Ala | Ala | Ser | Gly | Phe | Thr | Phe | Ser | Ser | Tyr | Ala | Met |
| | | | | 165 | | | | | 170 | | | | | 175 | |
| Ser | Trp | Val | Arg | Gln | Ala | Pro | Gly | Lys | Gly | Leu | Glu | Trp | Val | Ser | Thr |
| | | | 180 | | | | | 185 | | | | | 190 | | |
| Ile | Ser | Ser | Gly | Gly | Ser | Tyr | Thr | Ser | Tyr | Pro | Asp | Ser | Val | Lys | Gly |
| | | | 195 | | | | | 200 | | | | | 205 | | |
| Arg | Phe | Thr | Ile | Ser | Arg | Asp | Asn | Ser | Lys | Asn | Thr | Leu | Tyr | Leu | Gln |
| | 210 | | | | | 215 | | | | | 220 | | | | |
| Met | Asn | Ser | Leu | Arg | Ala | Glu | Asp | Thr | Ala | Val | Tyr | Tyr | Cys | Ala | Lys |
| 225 | | | | | 230 | | | | | 235 | | | | | 240 |
| Gln | Asp | Tyr | Ala | Met | Asn | Tyr | Trp | Gly | Gln | Gly | Thr | Leu | Val | Thr | Val |
| | | | | 245 | | | | | 250 | | | | | 255 | |
| Ser | Ser | Asp | Gln | Glu | Pro | Lys | Ser | Ser | Asp | Lys | Thr | His | Thr | Cys | Pro |
| | | | 260 | | | | | 265 | | | | | 270 | | |
| Pro | Cys | Pro | Ala | Pro | Glu | Ala | Ala | Gly | Ala | Pro | Ser | Val | Phe | Leu | Phe |
| | | | 275 | | | | | 280 | | | | | 285 | | |
| Pro | Pro | Lys | Pro | Lys | Asp | Thr | Leu | Met | Ile | Ser | Arg | Thr | Pro | Glu | Val |
| | | | 290 | | | | | 295 | | | | | 300 | | |
| Thr | Cys | Val | Val | Val | Asp | Val | Ser | His | Glu | Asp | Pro | Glu | Val | Lys | Phe |
| 305 | | | | | 310 | | | | | 315 | | | | | 320 |
| Asn | Trp | Tyr | Val | Asp | Gly | Val | Glu | Val | His | Asn | Ala | Lys | Thr | Lys | Pro |
| | | | | 325 | | | | | 330 | | | | | 335 | |
| Arg | Glu | Glu | Gln | Tyr | Asn | Ser | Thr | Tyr | Arg | Val | Val | Ser | Val | Leu | Thr |
| | | | 340 | | | | | 345 | | | | | 350 | | |
| Val | Leu | His | Gln | Asp | Trp | Leu | Asn | Gly | Lys | Glu | Tyr | Lys | Cys | Lys | Val |
| | | | 355 | | | | | 360 | | | | | 365 | | |
| Ser | Asn | Lys | Ala | Leu | Pro | Ala | Pro | Ile | Glu | Lys | Thr | Ile | Ser | Lys | Ala |
| | 370 | | | | | 375 | | | | | 380 | | | | |

```
Lys Gly Gln Pro Arg Glu Pro Gln Val Tyr Thr Leu Pro Pro Ser Arg
385                 390                 395                 400

Glu Glu Met Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
        420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
        450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490

<210> SEQ ID NO 66
<211> LENGTH: 116
<212> TYPE: PRT
<213> ORGANISM: Artificial Sequence
<220> FEATURE:
<223> OTHER INFORMATION: Human with mouse CDRs.

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Leu Val
            100                 105                 110

Thr Val Ser Ser
        115

<210> SEQ ID NO 67
<211> LENGTH: 107
<212> TYPE: PRT
<213> ORGANISM: Artificial Sequence
<220> FEATURE:
<223> OTHER INFORMATION: Human with mouse CDRs.

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln His Tyr Ser Thr Pro Trp
                    85                  90                  95

Thr Phe Gly Gly Gly Thr Lys Val Glu Ile Lys
                100                 105

<210> SEQ ID NO 68
<211> LENGTH: 116
<212> TYPE: PRT
<213> ORGANISM: Artificial Sequence
<220> FEATURE:
<223> OTHER INFORMATION: Human with mouse CDRs.

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Leu Val
            100                 105                 110

Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: Human with mouse CDRs.

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ala
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gly Gly Thr Lys Val Glu Ile Lys
                100                 105

<210> SEQ ID NO 70
<211> LENGTH: 116
<212> TYPE: PRT
<213> ORGANISM: Artificial Sequence
<220> FEATURE:
```

<223> OTHER INFORMATION: Human with mouse CDRs.

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Phe Asp Tyr Trp Gly Gln Gly Thr Leu Val
            100                 105                 110

Thr Val Ser Ser
            115

<210> SEQ ID NO 71
<211> LENGTH: 107
<212> TYPE: PRT
<213> ORGANISM: Artificial Sequence
<220> FEATURE:
<223> OTHER INFORMATION: Human with mouse CDRs.

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gly Gly Thr Lys Val Glu Ile Lys
            100                 105

<210> SEQ ID NO 72
<211> LENGTH: 116
<212> TYPE: PRT
<213> ORGANISM: Artificial Sequence
<220> FEATURE:
<223> OTHER INFORMATION: Human with mouse CDRs.

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Ser Gly Ser Tyr Thr Ser Tyr Pro Asp Ser Val

```
                    50                  55                  60
Lys Gly Arg Phe Thr Ile Ser Arg Asp Asn Ser Lys Asn Thr Leu Tyr
 65                     70                  75                  80

Leu Gln Met Asn Ser Leu Arg Ala Glu Asp Thr Ala Val Tyr Tyr Cys
                 85                  90                  95

Ala Lys Gln Asp Tyr Ala Met Asn Tyr Trp Gly Gln Gly Thr Leu Val
            100                 105                 110

Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Human with mouse CDRs.

<400> SEQUENCE: 73

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Ala
             20                  25                  30

Leu Asn Trp Tyr Gln Gln Lys Pro Gly Lys Ala Pro Lys Leu Leu Ile
         35                  40                  45

Tyr Ser Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105
```